US007029857B1

(12) United States Patent
Bonini et al.

(10) Patent No.: US 7,029,857 B1
(45) Date of Patent: Apr. 18, 2006

(54) PROCESSES FOR OBTAINING COMPOUNDS EMPLOYING SNORF72 RECEPTORS

(75) Inventors: James A. Bonini, Oakland, NJ (US); Gabriel S. Lerman, Teaneck, NJ (US); Kristine L. Ogozalek, Rochelle Park, NJ (US); Yong Quan, Fords, NJ (US)

(73) Assignee: H. Lundbeck A/S, Valby-Copenhagen (DK)

( * ) Notice: Subject to any disclaimer, the term of this patent is extended or adjusted under 35 U.S.C. 154(b) by 731 days.

(21) Appl. No.: 09/609,146

(22) Filed: Jun. 30, 2000

Related U.S. Application Data

(63) Continuation-in-part of application No. 09/558,099, filed on Apr. 25, 2000, now abandoned, which is a continuation-in-part of application No. 09/466,435, filed on Dec. 17, 1999, now abandoned.

(51) Int. Cl.
*G01N 33/53* (2006.01)
*C12N 5/10* (2006.01)

(52) U.S. Cl. ..................... 435/7.1; 435/7.2; 435/325; 435/348; 435/357; 435/361; 435/356; 435/365; 435/369; 435/354; 435/320.1; 530/356; 536/23.5

(58) Field of Classification Search ................ 530/350; 435/368, 365, 361, 7.1, 7.2
See application file for complete search history.

(56) References Cited

U.S. PATENT DOCUMENTS

| | | | | |
|---|---|---|---|---|
| 5,194,596 A | * | 3/1993 | Tischer et al. | 530/399 |
| 5,350,836 A | * | 9/1994 | Kopchick et al. | 530/399 |
| 6,383,761 B1 | * | 5/2002 | Conklin et al. | 435/7.21 |
| 6,461,836 B1 | * | 10/2002 | Elshourbagy et al. | 435/69.1 |

FOREIGN PATENT DOCUMENTS

| | | |
|---|---|---|
| WO | 9955732 | 11/1999 |
| WO | 0002919 | 1/2000 |
| WO | 0022131 | 4/2000 |
| WO | WO 00/22131 * | 4/2000 |
| WO | WO 00/22131 A1 * | 4/2000 |
| WO | 0031258 | 6/2000 |
| WO | WO0031258 | 6/2000 |
| WO | 0125269 | 4/2001 |

OTHER PUBLICATIONS

Vukicevic et al., 1996, PNAS USA 93:9021-9026.*
Derwent Database Accession No. Y44641 (published Apr. 18, 2000).
Derwent Database Accession No. Z49707 (published Apr. 18, 2000).
Derwent Database Accession No. Z49706 (published Apr. 18, 2000).
Derwent Database Accession No. Y44642 (published Apr. 18, 2000).
Derwent Database Accession No. Z33297 (published Feb. 21, 2000).
Derwent Database Accession No. Y52992 (published Feb. 21, 2000).
HTG Database Accession No. AC017104 (published Dec. 10, 1999).
HTG Database Accession No. AC008571 (published Aug. 3, 1999).
GSS Database Accession No. AQ019411 (published Jun. 9, 1998).
GSS Database Accession No. AQ015065 (published Jun. 9, 1998).
SwissProtPlus Database Accession No. O43664 (published Jun. 1, 1998).
SwissProtPlus Database Accession No. O55040 (published Jun. 1, 1998).
GenEMBL Database Accession No. AF044600 (published Feb. 12, 1998).
GenEMBL Database Accession No. AF044601 (published Feb. 12, 1998).
GenEMBL Database Accession No. AF044602 (published Feb. 12, 1998).
Expressed Sequence Tags Database Accession No. AA562357 (published Aug. 19, 1997).
Expressed Sequence Tags Database Accession No. N45474 (published Feb. 16, 1996).
Expressed Sequence Tags Database Accession No. H11359 (published Jun. 28, 1995).

(Continued)

*Primary Examiner*—Eileen B. O'Hara
(74) *Attorney, Agent, or Firm*—Stephen B. Kalinchak

(57) ABSTRACT

This invention provides isolated nucleic acids encoding mammalian SNORF62 and SNORF72 receptors, purified mammalian SNORF62 and SNORF72 receptors, vectors comprising nucleic acid encoding mammalian SNORF62 and SNORF72 receptors, cells comprising such vectors, antibodies directed to mammalian SNORF62 and SNORF72 receptors, nucleic acid probes useful for detecting nucleic acid encoding mammalian SNORF62 and SNORF72 receptors, antisense oligonucleotides complementary to unique sequences of nucleic acid encoding mammalian SNORF62 and SNORF72 receptors, transgenic, nonhuman animals which express DNA encoding normal or mutant mammalian SNORF62 and SNORF72 receptors, methods of isolating mammalian SNORF62 and SNORF72 receptors, methods of treating an abnormality that is linked to the activity of the mammalian SNORF62 and SNORF72 receptors, as well as methods of determining binding of compounds to mammalian SNORF62 and SNORF72 receptors, methods of identifying agonists and antagonists of SNORF62 and SNORF72 receptors, and agonists and antagonists so identified. This invention also provides methods of treating an abnormality that is linked to the activity of a mammalian NMU receptor, as well as methods of determining binding of compounds to mammalian NMU receptors, methods of identifying agonists and antagonists of NMU receptors, and agonists and antagonists so identified.

25 Claims, 38 Drawing Sheets

OTHER PUBLICATIONS

Expressed Sequence Tags Database Accession No. R13353 (published Apr. 13, 1995).
Expressed Sequence Tags Database Accession No. R13890 (published Apr. 13, 1995).
Tan, C.P., et al. *Genomics* (1998) 52(2), 223-229.
Fujii, R., et al., *J. Biol. Chem.*, Apr. 26, 2000.
Szekeres, P.G., et al., *J. Biol. Chem.*, May 12, 2000.
Fujii, R., et al., "Identification of Neuromedin U as the Cognate Ligand of the Orphan G Protein-Coupled Receptor FM-3", Jul. 14, 2000, J. Biol. Chem., 275(28): 21068-21074.
Hosoya, M., et al., "Identification and Functional Characterization of a Novel Subtype of Neuromedin U Receptor", Jul. 7, 2000, (e pub ahead of print).
Howard, A., et al., Identification of receptors for neuromedin U and its role in feeding, Jul. 6, 2000, Nature, 406:70-74.
Szekeres, P., et al., "Neuromedin U Is a Potent Agonist at the Orphan G Protein-coupled Receptor FM3", Jul. 7, 2000, J. Biol. Chem., 275(27): 20247-20250.
Skolnick, J. and J.S. Fetrow, "From genes to protein structure and function: novel applications of computational approaches in the genomic era", Trends in Biotechnology 18(1): 34-39 (2000).
GenEMBL Database Accession No. AC008571 (published Aug. 4, 1999) (Exhibit 1).
GenEMBL Database Accession No. HS474279 (published Feb. 17, 1996) (Exhibit 2).
GenEMBL Database Accession No. O55040 (published Jun. 1, 1998) (Exhibit 3).
GenEMBL Database Accession No. AAY71296 (published Nov. 2, 2000) (Exhibit 4).
GenEMBL Database Accession No. AAB02830 (published Aug. 22, 2000) (Exhibit 5).

* cited by examiner

FIGURE 1A

```
  1 GAGGGTGGAAGCCGGGTCTCCGCGGCCCGCATGACTCCTCTGCCTCAATTG   60
 61 CTCTGTCCCCTGGAGACCTGTACCCAGGGGTGCAAGGAACCCCATGGCTTGCAATGG  120
121 CAGTGCGGCCAGGGGCACTTTGACCCTGAGGACTTGAACCTGACGAGGCACTGAG  180
181 ACTCAAGTACCTGGGCGCCCCAGCAGACAGAGCTGTTCATGCCCACATACCT  240
241 GCTGATCTTCGTGGTGGGGCTGTGTGGGCAATGGGCTGACCTGTCTGGTCATCCTGCGCCA  300
301 CAAGGCCATGCGCACGCCTACCAACTACTACCTCTTCAGCCTGGCCGTGTCGGACCTGCT  360
361 GGTGCTGCTGGTGGGCCCTGCTGGAGCTCTATGAGATGTGGCACAACTACCCCTTCCT  420
421 GCTGGGCCGTTGGTGGCTGCTATTTCCGCACGCTACTGTTTGAGATGGTCTGCTGGCCTC  480
481 AGTGCTCAACGTCACTGCCCTGAGCGTGGAACGCTATGTGGCCGTGTGGTGCACCACTCCA  540
541 GGCCAGGTCCATGGTGACGCGGCCCATGTGCGCCGAGTGCTTGGGCCGTCTGGGGTCT  600
601 TGCCATGCTCTGCTCCCTGCCCAACACCAGCCTGCACGGCATCCGGCAGCTGACGTGCC  660
661 CTGCCCGGGGCCCAGTGCCCAGACTCAGCTGTTTGCATGCTGTCCGCCCACGGGCCCTCTA  720
```

FIGURE 1B

```
 721  CAACATGGTAGTGCAGACCACCGCGTGCTCTTCTTCTGCCTGCCCATGGCCATCATGAG   780
 781  CGTGCTCTACCTGCTCATTGGGCTGCGCGGGAGAGGCTGTGCTCATGCAGGA           840
 841  GGCCAAGGGGCAGGGCTCTGCAGCAGCCAGGTCCAGATACACCTGCAGGCTCCAGCAGCA   900
 901  CGATCGGGGGCCCGAGACAAGTGACCAAGAGATGCTGTGTTTGTCCCTGTCGTGTTTGGCAT  960
 961  CTGCTGGGCCCCGTTCCACGCCGTCATGTGGAGCGTCGTGTCACAGTGGACAGA         1020
1021  TGGCCTGCACCTGGCCTTCCAGCACGTGCACGTCATCTTCTTCTACCTGGG            1080
1081  CTCGGGCGGCCAACCCCGTGCTCTATAGCCTCATGTCCCAGCCGCTTCCAGAGACCTTCCA  1140
1141  GGAGGCCCTGTGCCTGCCATGCCTCAGACCCGCCACAGCTCCCACAG               1200
1201  CCTCAGCAGGATGACCAGGCAGCACCCTGTGTGATGTGGGCTCCCTGGGCAGCTGGGT    1260
1261  CCACCCCCTGGCTGGGAACGATGCCCAGAGGCGCAGCAAGAGACCGATCCATCCTGA     1318
```

```
1    AGGGGAGGCTCAGGCCTTGGATTTAATGTCAGGGATGAAAAACTTCAGAATGCTTCCT     60
61   GGATCTACCAGCAGAAACTAGAAGATCCATTCCAGAAACACCTGAACAGCACCGAGGAGT   120
121  ATCTGGCCTTCCTCTGCGGACCTCGGCGCAGCCACTTCTTCCCCGTGTCTGTGGTGT      180
181  ATGTGCCAATTTTGTGGTGGGGTCATTGGCAATGTCCTGGTGTGCCTGGTGATTCTGC     240
241  AGCACCAGGCTATGAAGACGCCCACCAACTACCTCTTCAGCCTGGCGGTCTCTGACC      300
301  TCCTGGTCCTGCTCCTTGGAATGCCCCTGGAGGTCTATGAGATGTGGCCAACTACCCTT    360
361  TCTTGTTCGGGCCCGTGGGCTGCTACTTCAAGACGCCCTCTTTGAGACCGTGTGCTTCG    420
421  CCTCCATCCTCAGCATCACCACCGGCTGAGCGCTACGTGGCCATCCTACACCCGT        480
481  TCCGCGGCCAAACTGCAGAGCACCGGGCCCGCCCTCAGGATCCTCGGCATCGTCTGGG     540
541  GCTTCTCCGTGCTCTTCTCCCTGCCCAACACCAGCATCCATGGCATCAAGTTCCACTACT  600
601  TCCCCAATGGGTCCCTGGTCCCAGTTCGGCCACCTGTACGGTCATCAAGCCCATGTGGA   660
661  TCTACAATTTCATCATCCAGTTCACCCTCCTATTCTACCTCCTCCCCATGACTGTCA     720
```

FIGURE 3B

```
721   TCAGTGTCCTCTACTACCTCATGGCACTCAGACTAAAGAAAGACAAATCTCTTGAGGCAG   780
781   ATGAAGGGAATGCAAATATTCAAAGACCCTGCAGAAATCAGTCAACAAGATGCTGTTTG   840
841   TCTTGGTCTTAGTGTTTGCTATCTGTTGGGCCCCGTTCCACATTGACCGACTCTTCTTCA   900
901   GCTTTGTGGAGGAGTGGAGTGAATCCCTGGCTGTCTGTGTTCAACCTCGTCCATGTGGTGT   960
961   CAGGTGTCTCTTCTTCTACCTGAGCTCAGCTGTCAACCCCATTATCTATAACCTACTGTCTC  1020
1021  GCCGCTTCCAGGCAGCATTCCAGAGAATGTGATCTCTCTTCTTTCCACAAACAGTGGCACTCCC  1080
1081  AGCATGACCCACAGTTGCCACCTGCCCCAGCGGAACATCTTCCTGACAGAATGCCACTTTG  1140
1141  TGGAGCTGACCGAAGATATAGGTCCCCAATTCCCCATGTCAGTCATCCATGCACAACTCTC  1200
1201  ACCTCCCAACAGCCCTCTAGTGAACAGATGTCAAGAACAAACTATCAAAGCTTCCACT  1260
1261  TTAACAAAACCTGAATTCTTTCAGAGCTGACTCTCCTC                        1298
```

```
  1 MTPLCLNCSVLPGDLYPGGARNPMACNGSAARGHFDP..EDLNLTDEALR  48
                                  ||  .  || |:| |
  1 ................MSGMEKLQNASWIYQQKLEDPFQKHLNSTEEYLA  34

49 LKYLGPQQTELFMPICATYLLIFVVGAVGNGLTCLVILRHKAMRTPTNYY  98
    ||...     |:|:    |. ||||| :|| | |||||.|.||:|||||
 35 F.LCGPRRSHFFLPVSVVYVPIFVVGVIGNVLVCLVILQHQAMKTPTNYY  83

99 LFSLAVSDLLVLLVGLPLELYEMWHNYPFLLGVGGCYFRTLLFEMVCLAS 148
    |||||||||||||.|:|||.|||| ||||| |  ||||:| ||| || ||
 84 LFSLAVSDLLVLLLGMPLEVYEMWRNYPFLFGPVGCYFKTALFETVCFAS 133

149 VLNVTALSVERYVAVVHPLQARSMVTRAHVRRVLGAVWGLAMLCSLPNTS 198
    :|.:| .||||||:.|| .|:    ||   |:|| ||| ..| ||||||
134 ILSITTVSVERYVAILHPFRAKLQSTRRRALRILGIVWGFSVLFSLPNTS 183

199 LHGIRQLHVPCRGPVPDSAVCMLVRPRALYNMVVQTTALLFFCLPMAIMS 248
    :|||:  : |    || || | .::| :|| ::| |. ||: ||| :.|
184 IHGIKFHYFPNGSLVPGSATCTVIKPMWIYNFIIQVTSFLFYLLPMTVIS 233

249 VLYLLIGLRLRRERLLLMQEAKGRGSAAARSRYTCRLQQHDRGRRQVTKM 298
    ||| |. |||::::  |     |    |   | . |     |: | ||
234 VLYYLMALRLKKDKSLEADEGN......ANIQRPC........RKSVNKM 269

299 LFVLVVVFGICWAPFHADRVMWSVVSQWTDGLHLAFQHVHVISGIFFYLG 348
    |||||.|| ||||||| |. :| | :|.: |     |||:||:||||
270 LFVLVLVFAICWAPFHIDRLFFSFVEEWSESLAAVFNLVHVVSGVFFYLS 319

349 SAANPVLYSLMSSRFRETFQEAL.CLGACCH.....RLRPRHSSHSLSRM 392
    || ||::|.|:| ||. ||  :         |    .| |  . |.
320 SAVNPIIYNLLSRRFQAAFQNVISSFHKQWHSQHDPQLPPAQRNIFLTEC 369

393 TTGSTLCDVGSLGSWVHPLAGNDGPEAQQETDPS............ 426
    |:|     :  .   ||       |
370 HFVELTEDIGPQFPCQSSMHNSHLPTALSSEQMSRTNYQSFHFNKT 415
```

FIGURE 14A

```
1    GTTGTGGATTTTAAGCTCAGTAATGGGAAAACTTGAAAATGCTTCCTGGATCCACGATCC    60
61   TCTCATGAAGTACTTGAACAGCACAGAGGAGTACTGGCCCACCTGTGTGGACCCAAGCG    120
121  CAGTGACCCTATCCCCTTCCGGTGTGTCTGTGCCTATGGCGCTGATCTTCCTGGTGGGGTAAT  180
181  GGGCAATCTTCTGGTGTGCATGGTGATTGTCCGACACATCAGACTTTGAAGACACCCACCAA  240
241  CTACTATCTCTTCAGCTTGGCCAGTCTCAGATCTGCTGGTCCTGCTCTTGGGCCTGTGTCGG  300
301  GGAAATCTACGAGATGTGGCACAATTACCCTTTCCTGTTCGGGCCTGTGGGATGCTACTT   360
361  CAAGACAGCCCTCTTCGAGACTGTGTGCTTTGCCTTCCATTCTCAGTGTCACCACGGTTAG  420
421  CGTAGAGCGCTATGTGGCCATTGTCCGAGCCAAGCTGGAGAGCACGCGGCG            480
481  ACGGGCCCTCAGGATCCTCAGCTCTGGAGCTTCTCTGTGTCTTTTCTTTGCCCAA        540
541  TACCAGCATCCATGGCATCAAGTTCCAGCACTTTCCCAACGGGTCCTCCGTACCTGGCTC    600
601  AGCCACCTGCACAGTCACCAAACCCATGTGGGTGTATAACTTGATCATCCAAGCTACCAG   660
661  CTTCCTCTTCTACATCCCTCCCAATGACCCTCATCAGCGTCCCTACTACCTCATGGGGCT   720
```

FIGURE 14B

```
 721   CAGGCTGAAGAGAGATGAATCCCTTGAGGCGAACAAAGTGGCTGTGAATATTCACAGACC    780
 781   CTCTAGAAAGTCAGTCACCAAGATGCTGTGTTTGTCTTGGTCCTCCTGTGTTTGCCATCTGCTG    840
 841   GACCCCCTTCCATGTGGACCGGCTCTTCTTCAGCTTTGTGGAAGAGTGGACAGAGTCCCT    900
 901   GGCTGCTGTGTTCAACCTCCATCCATGTGGTATCAGGTGTCTTCTTTTATCTGAGCTCCGC    960
 961   GGTCAACCCCATTATCTATAACCTCCTGTCTCGGGCGCTTCCGGGGCCTTTCGAAATGT    1020
1021   TGTCTCCCCTACCTGCAAATGGTGCCATCCCCGGCATCGGCCACAGGACCTCCAGCCCA    1080
1081   GAAGATCATCTTCTTGACAGAATGTCACCTCGTGAGCTGACAGAGGATGCAGGCCCCCA    1140
1141   GTTCCCTGGTCAGTCATCCATCCACACCAACCTTACCACGGCCCCCCTGTGCAGGAGA    1200
1201   GGTACCATAAAAGGAGTGGTCAGAAGGCCTC    1231
```

```
SNORF72_RAT     ~~~~~~~~~~  ~~~~~~~~~~  ~~~~~~~~~M  GKLENASWIH  ....DPLMK   YLNSTEEYLA
SNORF72_HUMAN   ~~~~~~~~~~  ~~~~~~~~~~  ~~~~~MSGM   EKLQNASWIY  QQKLEDPFQK  HLNSTEEYLA
SNORF62_HUMAN   MTPLCLNCSV  LPGDLYPGGA  RNPMACNGSA  ARGHFDP..E  DLNLTDEALR

SNORF72_RAT     H.LCGPKRSD  LSLPVSVAYA  LIFLVGVMGN  LLVCMVIVRH  QTLKTPTNYY
SNORF72_HUMAN   F.LCGPRRSH  FFLPVSVVYV  PIFVVGVIGN  VLVCLVILQH  QAMKTPTNYY
SNORF62_HUMAN   LKYLGPQQTE  LFMPICATYL  LIFVVGAVGN  GLTCLVILRH  KAMRTPTNYY

SNORF72_RAT     LFSLAVSDLL  VLLLGMPLEI  YEMWHNYPFL  FGPVGCYFKT  ALFETVCFAS
SNORF72_HUMAN   LFSLAVSDLL  VLLLGMPLEV  YEMWRNYPFL  FGPVGCYFKT  ALFETVCFAS
SNORF62_HUMAN   LFSLAVSDLL  VLLVGLPLEL  YEMWHNYPFL  LGVGGCYFRT  LLFEMVCLAS

SNORF72_RAT     ILSVTTVSVE  RYVAIVHPFR  AKLESTRRRA  LRILSLVWSF  SVVFSLPNTS
SNORF72_HUMAN   ILSITTVSVE  RYVAILHPFR  AKLQSTRRRA  LRILGIVWGF  SVLFSLPNTS
SNORF62_HUMAN   VLNVTALSVE  RYVAVVHPLQ  ARSMVTRAHV  RRVLGAVWGL  AMLCSLPNTS

SNORF72_RAT     IHGIKFQHFP  NGSSVPGSAT  CTVTKPMWVY  NLIIQATSFL  FYILPMTLIS
SNORF72_HUMAN   IHGIKFHYFP  NGSLVPGSAT  CTVIKPMWIY  NFIIQVTSFL  FYLLPMTVIS
SNORF62_HUMAN   LHGIRQLHVP  CRGPVPDSAV  CMLVRPRALY  NMVVQTTALL  FFCLPMAIMS
```

FIGURE 16B

```
SNORF72_RAT     VLYYLMGLRRL  KRDESL...E  A...NKVAVN  IHRPS.....  ...RKSVTKM
SNORF72_HUMAN   VLYYLMALRL   KKDKSL...E  A...DEGNAN  IQRPC.....  ...RKSVNKM
SNORF62_HUMAN   VLYLLIGLRL   RRERLLLMQE  AKGRGSAAAR  SRYTCRLQQH  DRGRRQVTKM

SNORF72_RAT     LFVLVLVFAI   CWTPFHVDRL  FFSFVEEWTE  SLAAVFNLIH  VVSGVFFYLS
SNORF72_HUMAN   LFVLVLVFAI   CWAPFHIDRL  FFSFVEEWSE  SLAAVFNLVH  VVSGVFFYLS
SNORF62_HUMAN   LFVLVVVFGI   CWAPFHADRV  MWSVVSQWTD  GLHLAFQHVH  VISGIFFYLG

SNORF72_RAT     SAVNPIIYNL   LSRRFRAAFR  NV..VSPTCK  WCHPRHRPQG  PPAQKIIFLT
SNORF72_HUMAN   SAVNPIIYNL   LSRRFQAAFQ  NV..ISSFHK  QWHSQHDPQL  PPAQRNIFLT
SNORF62_HUMAN   SAANPVLYSL   MSSRFRETFQ  EALCLGACCH  RLRPRHSSH.  SLSRMTTGST

SNORF72_RAT     ECHLVELTED   AGPQFPGQSS  IHNTNLTTAP  CAGEVP~~~~  ~~~~~~~~~~
SNORF72_HUMAN   ECHFVELTED   IGPQFPCQSS  MHNSHLPTAL  SSEQMSRTNY  QSFHFNKT~~
SNORF62_HUMAN   LCDVGSLGSW   VHPLAGNDGP  EAQQETDPS~  ~~~~~~~~~~  ~~~~~~~~~~
```

FIGURE 17A

```
   1  CACCATCTCGGTTTAAGATAAAGATATGGAGCTCTCCCCAAATGCTTCAACGGGCCTCTT   60
  61  GTCCTGCAATGACAGTGAGTTCAAGGAGCACTTTGACCCTTGAGGACCTGAACCTTACTCA  120
 121  TGAGGACCTGAGGCTGAAGTACTTGGGCCACAGCAGGTAAAACAATTTTTGCCCATCTG   180
 181  TGTCACGTACCTGTTGATCTTCGTAGTGGGCACTCTCTGGGCAACGGGTTGACCTGCACCGT  240
 241  CATCCTGCGCCAGAAGGCAATGCACACGCCCACCAACTTCTACCTCTTCAGTCTCTGCGGT  300
 301  GTCCGATTTGCTGGTCTCCTGGTGCCCCTGAACTTTATGAGATGCAGCACAA  360
 361  TTACCCATTCCAGCTGGTGCAGGTGGCTGTTACTTCCGGATACTGCTTTTGGAGACTGT  420
 421  CTGCCCTGGCTTCAGTGCTCAATGTCACAGCCCTAAGTGTGGAGCGTTATGTGGCCGTGGT  480
 481  GCACCCACTCCAAGCCAAGTCTGTGATGACACGGACCCATGTGCGCCATGTTGGGAGC  540
 541  CATCTGGGTCTTCGCTATTCTCTTCTGCCCAACACCAGCTTACATGGCCTCAGTCC  600
 601  ACTCTATGTACCCTGCCGGTGCCCGGGGCCCGGTGCCCGATTCAGTTACGTGTACGCTGGTGCGTCC  660
 661  CCAGTTCTTCTACAAGTTGGTAATACAGACGACCATACTGCTCTTCTGTCTGCCCAT  720
```

FIGURE 17B

```
721   GGTCACCATCAGTGTGCTGTACCTGCTCATTGGGCTGAGGCTGCGGAGGGAGAGGATGTT    780
781   GCTCCAAGAGGAGGTCAAGGGCAGGATATCTGCAGCAGCCAGGCCTCCCACAGAAG        840
841   TATTCAGCTTCGAGATAGGGAACGCAGAGTGACCAAGATGCTAATTGCTCTGGTTAT       900
901   AGTATTTGGCACCTGCTGGGTTCCATTGCTGACCGTCTCATGTGGAGTATGGTGTC        960
961   CCATTGGACTGACGGCCTGCGCCTTCCAGTCTGTGCACCTTGCTTCTGGTGTCTT        1020
1021  CTTGTACCTCGGCTCAGGGCTAACCCGGAGCTCTACAACCTCATGTCCACTCGCTTCCG    1080
1081  AGAGTCCTTCCGGGAAACCCTGGGCCTGTGCATCGCCACCAACCGCG                1140
1141  TCACGACTCCCATAGCCACCTTAGGTTGACCAGTCAGCACCCTGTGACAGGAACAG      1200
1201  CAGGGATGTACCCCTGGCTGAGAACAGGATCCAGGGTGTGAGCAAGAGACAGACCCTCC    1260
1261  TGAATAAAATCCTGTGGCCTCACCCACAGGGC                              1292
```

```
  1 GGGACAGCAGCACGTTAGACCCAAGTCTTCATGGACTTCCTCTCTCAGTGTCATTTTTCTCA   60
 61 TCTGTAAAATGGGATTGTGTCCAGAAAAGGAGACATTCTCAGCTTCGGCTCTCCCCAA      120
121 ATGCTTCAAACGGGCCCTCTTGTCCTGCAATGACAGTGAGTTCAAGGAGCACTTTGACCTTG  180
181 AGGACCTGAACCTTACTCATGAGGACCTGAGGCTGAAGTACTTGGGGCCACAGCAGGTAA    240
241 AACAATTTTTGCCCATCTGTGTCACGTACCTGTTGATCTTCGTAGTGGGCACTCTGGGCA    300
301 ACGGGTTGACCTGCACCGTCATCCTGCGCCAGAAGGCAATGCACGCCCACCAACTTCT      360
361 ACCTCTTCAGTCTCGCGGTGTCCGATTTGCTGGTGCTCCTGGTGCTTGCCCCTGGAAC      420
421 TTTATGAGATGCAGCACAATTACCCATTCCAGCTGGGTGCAGGTGGCTGTGTTACTTCCGGA 480
481 TACTGCTTTTGGAGACTGTCTGCTTCAGTGCTTCAATGTCACAGCCCTAAGTGTGG       540
541 AGCGTTATGTGGCCGTGGTGCACCACTCCAAGCCAAGTCTGTGATGACACGGACCCATG    600
601 TGCGCCGCATGTGTGGGAGCCATCTGGGTCTTCGCTATTCTCTCTGCCCAACACCA       660
661 GCTTACATGGCCCTCAGTCCACTCTATGTACCCCTGCCGGGGGCCGGTGCCCGATTCAGTTA 720
```

FIGURE 19B

```
 721  CGTGTACGCTGGTGCGTCCCCAGTTCTTCTACAAGTTGGTAATACAGACGACCATACTGC   780
 781  TCTTCTCTGTCTGCCCATGGTCACCATCAGTGTGCTGTACCTGCTCATTGGGCTGAGGC    840
 841  TGCGGAGGGAGAGGATGTTGCTCCAAGAGGAGGTCAAGGGCCAGGATATCTGCAGCAGCCA  900
 901  GGCAGGCCTCCCACAGAAGTATTCAGCTTCGAGATAGGGAACGCAGACAGGTGACCAAGA   960
 961  TGCTAATTGCTCTGGTTATAGTATTTGGCACCTGCTGGTTCCATTCCATGCTGACCGTC   1020
1021  TCATGTGGAGTATGGTGTCCCATTGACTGACGGCCTGCGCCTTCCAGTCTGTGC        1080
1081  ACCTTGCTTCTGGTGTCTTCTTGTACCTCGGCTAACCCGGAGCTCTACAACC           1140
1141  TCATGTCCACTCGCTTCCGAGAGTCCCTTCCGGGAAACCCTGGGACACGGTGCT        1200
1201  GTCATCGCCACCAACCGGTCACGACTCCCATAGCCACCTTAGGTTGACCACAGTCAGCA   1260
1261  CCCTGTGTGACAGGAACAGCAGGATGTACCCCTGGCTGAGAACAGGGATCCAGGGTGTG   1320
1321  AGCAAGAGAGACAGACCCCTCCTGAATAAAATCCTGTGGCCCTCACCCACAGGGC       1371
```

```
Rat SNORF62a  ~~~~~~~~~~  ~~~~~~~~~~  ~~~~~MELS  PNASTGLLSC  NDSEFKEHFD
Rat SNORF62b  MDFLSQCHFF  LICKMGLLSR  KRRHSQLRLS  PNASTGLLSC  NDSEFKEHFD
Hum SNORF62   ~~~~~~~~~~  ~~~~MTPLCL  NCSVLPGDLY  PGGARNPMAC  NGSAARGHFD

Rat SNORF62a  LEDLNLTHED  LRLKYLGPQQ  VKQFLPICVT  YLLIFVVGTL  GNGLTCTVIL
Rat SNORF62b  LEDLNLTHED  LRLKYLGPQQ  VKQFLPICVT  YLLIFVVGTL  GNGLTCTVIL
Hum SNORF62   PEDLNLTDEA  LRLKYLGPQQ  TELFMPICAT  YLLIFVVGAV  GNGLTCLVIL

Rat SNORF62a  RQKAMHTPTN  FYLFSLAVSD  LLVLLVGLPL  ELYEMQHNYP  FQLGAGGCYF
Rat SNORF62b  RQKAMHTPTN  FYLFSLAVSD  LLVLLVGLPL  ELYEMQHNYP  FQLGAGGCYF
Hum SNORF62   RHKAMRTPTN  YYLFSLAVSD  LLVLLVGLPL  ELYEMWHNYP  FLLGVGGCYF

Rat SNORF62a  RILLLETVCL  ASVLNVTALS  VERYVAVVHP  LQAKSVMTRT  HVRRMLGAIW
Rat SNORF62b  RILLLETVCL  ASVLNVTALS  VERYVAVVHP  LQAKSVMTRT  HVRRMLGAIW
Hum SNORF62   RTLLFEMVCL  ASVLNVTALS  VERYVAVVHP  LQARSMVTRA  HVRRVLGAVW
```

FIGURE 21B

```
Rat  SNORF62a   VFAILFSLPN TSLHGLSPLY VPCRGPVPDS VTCTLVRPQF FYKLVIQTTI
Rat  SNORF62b   VFAILFSLPN TSLHGLSPLY VPCRGPVPDS VTCTLVRPQF FYKLVIQTTI
Hum  SNORF62    GLAMLCSLPN TSLHGIRQLH VPCRGPVPDS AVCMLVRPRA LYNMVQTTA

Rat  SNORF62a   LLFFCLPMVT ISVLYLLIGL RLRRERMLLQ EEVKGRISAA ARQASHRSIQ
Rat  SNORF62b   LLFFCLPMVT ISVLYLLIGL RLRRERMLLQ EEVKGRISAA ARQASHRSIQ
Hum  SNORF62    LLFFCLPMAI MSVLYLLIGL RLRRERLLLM QEAKGRGSAA ARSRYTCRLQ

Rat  SNORF62a   LRDRERRQVT KMLIALVIVF GTCWVPFHAD RLMWSMVSHW TDGLRLAFQS
Rat  SNORF62b   LRDRERRQVT KMLIALVIVF GTCWVPFHAD RLMWSMVSHW TDGLRLAFQS
Hum  SNORF62    QHDRGRRQVT KMLFVLVVVF GICWAPFHAD RVMWSVVSQW TDGLHLAFQH

Rat  SNORF62a   VHLASGVFLY LGSAANPELY NLMSTRFRES FRETLGLGTR CCHRHQPRHD
Rat  SNORF62b   VHLASGVFLY LGSAANPELY NLMSTRFRES FRETLGLGTR CCHRHQPRHD
Hum  SNORF62    VHVISGIFFY LGSAANPVLY SLMSSRFRET FQEALCLGA. CCHRLRPRHS
```

FIGURE 21C

```
Rat  SNORF62a  SHSHLRLTTV  STLCDRNSRD  V....PLAENR  DPGCEQETDP  PE
Rat  SNORF62b  SHSHLRLTTV  STLCDRNSRD  V....PLAENR  DPGCEQETDP  PE
Hum  SNORF62   SHSLSRMTTG  STLCDVGSLG  SWVHPLAGND   GPEAQQETDP  S~
```

PROCESSES FOR OBTAINING COMPOUNDS EMPLOYING SNORF72 RECEPTORS

This application is a continuation-in-part of U.S. Ser. No. 09/558,099, filed Apr. 25, 2000, now abandoned, which is a continuation-in-part of U.S. Ser. No. 09/466,435, filed Dec. 17, 1999, now abandoned, the contents of which are hereby incorporated by reference into the subject application.

BACKGROUND OF THE INVENTION

Throughout this application various publications are referred to by partial citations within parenthesis. Full citations for these publications may be found at the end of the specification immediately preceding the claims. The disclosures of these publications, in their entireties, are hereby incorporated by reference into this application in order to more fully describe the state of the art to which the invention pertains.

Neuroregulators comprise a diverse group of natural products that subserve or modulate communication in the nervous system. They include, but are not limited to, neuropeptides, amino acids, biogenic amines, lipids and lipid metabolites, and other metabolic byproducts. Many of these neuroregulator substances interact with specific cell surface receptors which transduce signals from the outside to the inside of the cell. G-protein coupled receptors (GPCRs) represent a major class of cell surface receptors with which many neurotransmitters interact to mediate their effects. GPCRs are characterized by seven membrane-spanning domains and are coupled to their effectors via G-proteins linking receptor activation with intracellular biochemical sequelae such as stimulation of adenylyl cyclase. This application describes the identification of two GPCRs, SNORF62 and SNORF72, as receptors for neuromedin U (NMU) neuropeptides.

Neuropeptides are synthesized and released from neurons to mediate their effects on cells within the nervous system or on peripheral targets. NMU-25 and NMU-8 are bioactive peptides originally isolated from porcine spinal cord (Minamino, N. et al. 1985a and 1985b). NMU-8 corresponds to the C-terminus of porcine NMU-25 preceded by Arg-Arg residues and may therefore be generated by enzymatic cleavage. NMU homologues have been identified in many species including human (25 amino acids) and rat (23 amino acids).

The amino acid sequence for human NMU-25 is as follows:
F R V D E E F Q S P F A S Q S R G Y F L F R P R N—NH$_2$ (SEQ ID NO: 5).

The amino acid sequence for porcine NMU-25 is as follows:
F K V D E E F Q G P I V S Q N R R Y F L F R P R N—NH$_2$ (SEQ ID NO: 6).

The amino acid sequence for rat NMU-23 is as follows: Y K V N E-Y Q G P-V A P S G G F F L F R P R N—NH$_2$ (SEQ ID NO: 7)(—indicates gaps in rat NMU-23 sequence to demonstrate optimum alignment).

The amino acid sequence for NMU-8 is Y F L F R P R N—NH$_2$ (SEQ ID NO: 8). All of the preceding sequences were taken from Nandha and Bloom 1993 and Austin, et al. 1995.

Interestingly, the 8 carboxy-terminal residues of human NMU-25 are identical to those in porcine, rabbit and guinea pig NMU and differ only by one residue from the C-terminus of frog, rat, dog and chicken NMU (Austin et al. 1995). C-terminal NMU peptides (8–9 amino acids) have also been identified in guinea pig, chicken and dog tissue extracts (Minamino et al. 1985a and 1985b, Domin et al. 1989, O'Harte et al. 1991). Indeed, the region of rat NMU-23 critical for smooth muscle contractile activity was found to reside between residues 17–22 (C-terminal region) (Hashimoto et al. 1991, Sakura et al. 1991). However, other groups have demonstrated the necessity of the amidated C-terminal asparagine (Asn23) for activity as well (Nandha and Bloom 1993). Full length NMU is approximately 3-fold more potent than NMU-8 in smooth muscle contraction assays suggesting that the N-terminal region of the peptide also contributes to the activity (Nandha and Bloom, 1993). Several residues in the middle region of the peptide are conserved between species including Glu5, Gln8 and Pro10 supporting the functional importance of this region of the peptide (Nandha and Bloom, 1993). The C-terminus of NMU shares some homology with rat pancreatic polypeptide (PP): Leu-X-Arg-Pro-Arg-X-amide and contains a terminal asparaginamide also present in vasoactive intestinal polypeptide (VIP) (Nandha and Bloom 1993). However, the structure of NMU is unrelated to the other neuromedin peptides isolated by Minamino et al. (1985a,b).

A profound effect of NMU has been observed in rats on the in vivo release of stress-related modulators from the anterior pituitary and adrenal glands (reviewed in Malendowicz and Markowska 1994). Following a single subcutaneous injection of NMU-8 (6 μg/100 g body weight), adrenocorticotropic hormone (ACTH) blood concentrations are elevated transiently (3–12 hours) and plasma corticosterone levels remain elevated for 24 hours (Malendowicz et al., 1993). In addition, the stress-evoked rise in corticosterone was absent in rats treated for 6 days with NMU-8 (Malendowicz et al. 1994a). Since corticosterone exerts both mineralocorticoid and glucocorticoid effects, regulation of its release by NMU ligands would be expected to modulate fluid homeostasis, ionic balance and metabolism. Although the mechanisms that mediate these effects remain unclear, identification of NMU-like immunoreactivity in nerve fibers in the rat hypothalamic paraventricular and supraoptic nuclei suggest a potential role for NMU in the hypothalamic regulation of pituitary function (Steel et al. 1988).

The corticosterone releasing effects of NMU may be mediated in part by direct effects on the adrenal gland. In rat adrenal gland slices, NMU-8 markedly increased basal corticosterone and pregnenolone steroid secretion (Malendowicz et al. 1994a and 1994b). These effects require the presence of adrenal medulla suggesting that NMU-8 acts on medullary chromaffin cells which may stimulate cells of the cortex through a paracrine mechanism. On the other hand, rat NMU-23 directly decreased basal corticosterone secretion from isolated rat inner adrenocortical cells (in the absence of medullary cells) while NMU-8 was without effect (Malendowicz and Nussdorfer 1993). This discrepancy between NMU-23 and NMU-8 effects on adrenal cortical cells suggests that the NMU receptor in these cells differs from that responsible for smooth muscle contraction. Repeated NMU-8 administration also decreased adrenal weight and the number of cells in the zona reticularis, further suggesting a stimulatory role for NMU on adrenal gland (Malendowicz et al. 1994a). NMU ligands may therefore be useful for directly regulating secretion from the adrenal gland.

Although NMU-like immunoreactivity has not been demonstrated within the adrenal gland or circulating in plasma, corticotrophs within the anterior lobe of rat and human pituitary gland contain high levels of NMU-like immunoreactivity (Steel et al. 1988) suggesting a possible hormonal role for NMU. Co-release of NMU with other bioactive peptides is likely to occur since NMU was observed by electron microscopy to be present in the same secretory granules as ACTH and galanin (Cimini et al. 1993).

Furthermore, both ACTH and NMU are present in human pituitary corticotropinomas as well as in ACTH expressing tumors from a variety of other tissue sources (Steel et al. 1988). Supporting a potential hormonal role of NMU, is the identification of a small population of NMU positive parafollicular C-cells in rat thyroid gland (Domin et al. 1990 and Lo et al. 1992).

Activities of this peptide also include a hypertensive effect when given intravenously to rats at a high dose (1 nmole; Gardiner et al. 1990). However, at a lower dose (0.1 nmole), NMU caused potent constrictor effects on the superior mesenteric vascular bed reducing mesenteric blood flow without changing systemic blood pressure. The NMU-induced reduction in mesenteric blood flow was also demonstrated in dog (Sumi et al. 1987). In addition, a slight increase in blood flow to the pancreas was measured in these experiments. Such actions suggest the involvement of NMU in the regulation of blood flow to the digestive tract and subsequent effects on digestion.

NMU was originally isolated based on its potent uterine contractile activity in vitro and has contractile activity on other smooth muscle preparations including chicken crop (Minamino, N. et al. 1985a, 1985b). Isolated muscle strips from the dome of the human urinary bladder were also contracted by NMU (Maggi et al. 1990) suggesting a role for this peptide in urinary control. NMU-like immunoreactivity has been identified in high levels in the rat genito-urinary systems including vas deferens, prostate, fallopian tube, urethra, vagina, ovary and uterus (reviewed in Nandha and Bloom 1993). Smooth muscle contractile or other hormonal effects of NMU in these tissues may regulate urinary control and/or reproductive functions.

Along with many other neuropeptides, NMU is present in nerves throughout the gastrointestinal tract (reviewed in Nandha and Bloom 1993). NMU stimulates contraction of isolated longitudinal muscle of human ileum (Maggi et al. 1990) and rat stomach circular muscle (Benito-Orfila et al. 1991) suggesting a role for NMU in gastric emptying and intestinal motility. Interestingly, porcine jejunum (Brown and Quito 1988) and guinea pig small intestine (Minamino et al. 1985b) are not contracted by NMU indicating species differences in gut regulation by this peptide. However, ion transport is modulated by NMU-8 in isolated porcine jejunal mucosa (Brown and Quito 1988). NMU-like immunoreactivity in the intestine has been localized to both the submucosal and myenteric ganglion cells (Ballesta et al. 1988) consistent with the observed effects on contractility, blood flow and absorptive/secretory functions (Ballesta et al. 1988).

Although higher concentrations of NMU are found in the periphery than in the central nervous system (CNS), immunocytochemical analysis demonstrated the presence of NMU in nerve fibers in many CNS regions with concentrations in discrete functional systems (Honzawa et al. 1987, Ballesta et al. 1988 and reviewed in Domin et al. 1987). For example, NMU-like immunoreactivity was identified in all of the cranial nuclei associated with somato-motor function (Ballesta et al. 1988). Several structures associated with sensory processing are also rich in NMU containing fibers including spinal cord (dorsal horn>ventral horn), trigeminal sensory nuclei, vestibular nuclei and other nuclei associated with descending spinal pathways (Honzawa et al. 1987). This localization suggests a role for NMU in perception and processing of sensory stimuli including pain.

Three cerebellar nuclei (nucleus medialis, interpostitus and lateralis) also demonstrated NMU-like immunoreactivity, consistent with the potential importance of NMU in sensory processing. Neuronal cell bodies containing NMU-like immunoreactivity have been identified in the arcuate nucleus of the hypothalamus, an area identified as important for the regulation of food intake and neuroendocrine control.

Relatively high levels of NMU-like immunoreactivity were also detected in the nucleus accumbens (Domin et al. 1987), an area where dopaminergic transmission is involved in reward and reinforcement of learned behaviors. The presence of NMU in another area important in dopaminergic transmission, the substantia nigra, (Domin et al. 1987) suggests a role for NMU in the modulation of dopaminergic actions in movement control as well. NMU-like immunoreactivity is also found in the hippocampus, amygdala and other portions of the limbic system suggesting a role for NMU ligands in affective disorders, psychosis and cognition.

G-protein coupled receptors (GPCR's) activated by this peptide and related analogues were postulated to exist based on binding of [$^{125}$I]rat NMU in rat uterus membranes (Nandha K. A. et al. 1993). The binding is saturable and of high affinity (Kd=0.35 nM, maximal binding capacity (Bmax)=580 fmol/mg protein). This affinity corresponds to the EC50 of contractile activity in this tissue, 0.2 nM, consistent with the involvement of this binding site in NMU-induced uterine contraction. The GTP analogue, GTPγS, inhibited binding of [$^{125}$I]rat NMU-23 suggesting that the binding site is a GPCR. In addition, chemical cross-linking identified the binding protein as having an apparent Mr of 48,500 which is consistent with the expected size of a GPCR protein.

Nandha et al. (1994) also identified [$^{125}$I]rat NMU-23 binding sites in rat uterus tissue slices and in the indusium griseum by autoradiography.

SUMMARY OF THE INVENTION

This invention provides an isolated nucleic acid encoding a mammalian SNORF62 receptor.

This invention also provides an isolated nucleic acid encoding a mammalian SNORF72 receptor.

This invention further provides a purified mammalian SNORF62 receptor protein.

This invention still further provides a purified mammalian SNORF72 receptor protein.

Furthermore, this invention provides a nucleic acid probe comprising at least 15 nucleotides, which probe specifically hybridizes with a nucleic acid encoding a mammalian SNORF62 receptor, wherein the probe has a sequence complementary to a unique sequence present within one of the two strands of the nucleic acid encoding the human SNORF62 receptor contained in plasmid pEXJ.T3T7-hS-NORF62-f (Patent Deposit Designation No. PTA-1042).

This invention further provides a nucleic acid probe comprising at least 15 nucleotides, which probe specifically hybridizes with a nucleic acid encoding a mammalian SNORF72 receptor, wherein the probe has a sequence complementary to a unique sequence present within one of the two strands of the nucleic acid encoding the human SNORF72 receptor contained in plasmid pEXJ.T3T7-hS-NORF72-f (Patent Deposit Designation No. PTA-1446).

This invention further provides a nucleic acid probe comprising at least 15 nucleotides, which probe specifically hybridizes with a nucleic acid encoding a mammalian SNORF72 receptor, wherein the probe has a sequence complementary to a unique sequence present within one of the two strands of the nucleic acid encoding the rat SNORF72 receptor contained in plasmid pEXJ.BS-rS-NORF72-f (Patent Deposit Designation No. PTA-1927).

This invention provides a nucleic acid probe comprising at least 15 nucleotides, which probe specifically hybridizes with a nucleic acid encoding a mammalian SNORF62 receptor, wherein the probe has a sequence complementary to a unique sequence present within (a) the nucleic acid sequence shown in FIGS. 1A–1B (SEQ ID NO: 1) or (b) the reverse complement thereof.

This invention also provides a nucleic acid probe comprising at least 15 nucleotides, which probe specifically hybridizes with a nucleic acid encoding a mammalian SNORF72 receptor, wherein the probe has a sequence complementary to a unique sequence present within (a) the nucleic acid sequence shown in FIGS. 3A–3B (SEQ ID NO: 3) or (b) the reverse complement thereof.

This invention also provides a nucleic acid probe comprising at least 15 nucleotides, which probe specifically hybridizes with a nucleic acid encoding a mammalian SNORF72 receptor, wherein the probe has a sequence complementary to a unique sequence present within (a) the nucleic acid sequence shown in FIGS. 15A–15B (SEQ ID NO: 25) or (b) the reverse complement thereof.

This invention further provides a transgenic, nonhuman mammal comprising a homologous recombination knockout of the native mammalian SNORF62 receptor.

This invention still further provides a transgenic, nonhuman mammal comprising a homologous recombination knockout of the native mammalian SNORF72 receptor.

This invention additionally provides a process for identifying a chemical compound which specifically binds to a mammalian SNORF62 receptor which comprises contacting cells containing DNA encoding, and expressing on their cell surface, the mammalian SNORF62 receptor, wherein such cells do not normally express the mammalian SNORF62 receptor, with the compound under conditions suitable for binding, and detecting specific binding of the chemical compound to the mammalian SNORF62 receptor.

Furthermore, this invention provides a process for identifying a chemical compound which specifically binds to a mammalian SNORF62 receptor which comprises contacting a membrane preparation from cells containing DNA encoding, and expressing on their cell surface, the mammalian SNORF62 receptor, wherein such cells do not normally express the mammalian SNORF62 receptor, with the compound under conditions suitable for binding, and detecting specific binding of the chemical compound to the mammalian SNORF62 receptor.

This invention further provides a process for identifying a chemical compound which specifically binds to a mammalian SNORF72 receptor which comprises contacting cells containing DNA encoding, and expressing on their cell surface, the mammalian SNORF72 receptor, wherein such cells do not normally express the mammalian SNORF72 receptor, with the compound under conditions suitable for binding, and detecting specific binding of the chemical compound to the mammalian SNORF72 receptor.

This invention provides a process for identifying a chemical compound which specifically binds to a mammalian SNORF72 receptor which comprises contacting a membrane preparation from cells containing DNA encoding, and expressing on their cell surface, the mammalian SNORF72 receptor, wherein such cells do not normally express the mammalian SNORF72 receptor, with the compound under conditions suitable for binding, and detecting specific binding of the chemical compound to the mammalian SNORF72 receptor.

Moreover, this invention provides a process involving competitive binding for identifying a chemical compound which specifically binds to a mammalian NMU receptor which comprises separately contacting cells expressing on their cell surface the mammalian NMU receptor, wherein such cells do not normally express the mammalian NMU receptor, with both the chemical compound and a second chemical compound known to bind to the receptor, and with only the second chemical compound, under conditions suitable for binding of such compounds to the receptor, and detecting specific binding of the chemical compound to the mammalian NMU receptor, a decrease in the binding of the second chemical compound to the mammalian NMU receptor in the presence of the chemical compound being tested indicating that such chemical compound binds to the mammalian NMU receptor.

This invention also provides a process involving competitive binding for identifying a chemical compound which specifically binds to a mammalian NMU receptor which comprises separately contacting a membrane preparation from cells expressing on their cell surface the mammalian NMU receptor, wherein such cells do not normally express the mammalian NMU receptor, with both the chemical compound and a second chemical compound known to bind to the receptor, and with only the second chemical compound, under conditions suitable for binding of such compounds to the receptor, and detecting specific binding of the chemical compound to the mammalian NMU receptor, a decrease in the binding of the second chemical compound to the mammalian NMU receptor in the presence of the chemical compound being tested indicating that such chemical compound binds to the mammalian NMU receptor.

This invention further provides a method of screening a plurality of chemical compounds not known to bind to a mammalian NMU receptor to identify a compound which specifically binds to the mammalian NMU receptor, which comprises (a) contacting cells transfected with, and expressing, DNA encoding the mammalian NMU receptor with a compound known to bind specifically to the mammalian NMU receptor; (b) contacting the cells of step (a) with the plurality of compounds not known to bind specifically to the mammalian NMU receptor, under conditions permitting binding of compounds known to bind to the mammalian NMU receptor; (c) determining whether the binding of the compound known to bind to the mammalian NMU receptor is reduced in the presence of the plurality of compounds, relative to the binding of the compound in the absence of the plurality of compounds; and if so (d) separately determining the binding to the mammalian NMU receptor of each compound included in the plurality of compounds, so as to thereby identify any compound included therein which specifically binds to the mammalian NMU receptor.

This invention still further provides a method of screening a plurality of chemical compounds not known to bind to a mammalian NMU receptor to identify a compound which specifically binds to the mammalian NMU receptor, which comprises (a) contacting a membrane preparation from cells transfected with, and expressing, DNA encoding the mammalian NMU receptor with the plurality of compounds not known to bind specifically to the mammalian NMU receptor under conditions permitting binding of compounds known to bind to the mammalian NMU receptor; (b) determining whether the binding of a compound known to bind to the mammalian NMU receptor is reduced in the presence of the plurality of compounds, relative to the binding of the compound in the absence of the plurality of compounds; and if so (c) separately determining the binding to the mammalian NMU receptor of each compound included in the plurality of compounds, so as to thereby identify any compound included therein which specifically binds to the mammalian NMU receptor.

Furthermore, this invention provides a method for diagnosing a predisposition to a disorder associated with the activity of a specific mammalian allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a mammalian SNORF62 receptor and labeled with a detectable marker; (e) detecting labeled bands which have hybridized to the DNA encoding a mammalian SNORF62 receptor of claim 1 to create a unique band pattern specific to the DNA of subjects suffering from the disorder; (f) repeating steps (a)–(e) with DNA obtained for diagnosis from subjects not yet suffering from the disorder; and (g) comparing the unique band pattern specific to the DNA of subjects suffering from the disorder from step (e) with the band pattern from step (f) for subjects not yet suffering from the disorder so as to determine whether the patterns are the same or different and thereby diagnose predisposition to the disorder if the patterns are the same.

This invention provides a method for diagnosing a predisposition to a disorder associated with the activity of a specific mammalian allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a mammalian SNORF72 receptor and labeled with a detectable marker; (e) detecting labeled bands which have hybridized to the DNA encoding a mammalian SNORF72 receptor of claim 2 to create a unique band pattern specific to the DNA of subjects suffering from the disorder; (f) repeating steps (a)–(e) with DNA obtained for diagnosis from subjects not yet suffering from the disorder; and (g) comparing the unique band pattern specific to the DNA of subjects suffering from the disorder from step (e) with the band pattern from step (f) for subjects not yet suffering from the disorder so as to determine whether the patterns are the same or different and thereby diagnose predisposition to the disorder if the patterns are the same.

This invention also provides a process for determining whether a chemical compound is a mammalian SNORF62 receptor agonist which comprises contacting cells transfected with and expressing DNA encoding the mammalian SNORF62 receptor with the compound under conditions permitting the activation of the mammalian SNORF62 receptor, and detecting any increase in mammalian SNORF62 receptor activity, so as to thereby determine whether the compound is a mammalian SNORF62 receptor agonist.

This invention further provides a process for determining whether a chemical compound is a mammalian SNORF62 receptor antagonist which comprises contacting cells transfected with and expressing DNA encoding the mammalian SNORF62 receptor with the compound in the presence of a known mammalian SNORF62 receptor agonist, under conditions permitting the activation of the mammalian SNORF62 receptor, and detecting any decrease in mammalian SNORF62 receptor activity, so as to thereby determine whether the compound is a mammalian SNORF62 receptor antagonist.

This invention still further provides a process for determining whether a chemical compound is a mammalian SNORF72 receptor agonist which comprises contacting cells transfected with and expressing DNA encoding the mammalian SNORF72 receptor with the compound under conditions permitting the activation of the mammalian SNORF72 receptor, and detecting any increase in mammalian SNORF72 receptor activity, so as to thereby determine whether the compound is a mammalian SNORF72 receptor agonist.

This invention additionally provides a process for determining whether a chemical compound is a mammalian SNORF72 receptor antagonist which comprises contacting cells transfected with and expressing DNA encoding the mammalian SNORF72 receptor with the compound in the presence of a known mammalian SNORF72 receptor agonist, under conditions permitting the activation of the mammalian SNORF72 receptor, and detecting any decrease in mammalian SNORF72 receptor activity, so as to thereby determine whether the compound is a mammalian SNORF72 receptor antagonist.

Moreover, this invention provides a process for determining whether a chemical compound specifically binds to and activates a mammalian SNORF62 receptor, which comprises contacting cells producing a second messenger response and expressing on their cell surface the mammalian SNORF62 receptor, wherein such cells do not normally express the mammalian SNORF62 receptor, with the chemical compound under conditions suitable for activation of the mammalian SNORF62 receptor, and measuring the second messenger response in the presence and in the absence of the chemical compound, a change in the second messenger response in the presence of the chemical compound indicating that the compound activates the mammalian SNORF62 receptor.

This invention also provides a process for determining whether a chemical compound specifically binds to and activates a mammalian SNORF72 receptor, which comprises contacting cells producing a second messenger response and expressing on their cell surface the mammalian SNORF72 receptor, wherein such cells do not normally express the mammalian SNORF72 receptor, with the chemical compound under conditions suitable for activation of the mammalian SNORF72 receptor, and measuring the second messenger response in the presence and in the absence of the chemical compound, a change in the second messenger response in the presence of the chemical compound indicating that the compound activates the mammalian SNORF72 receptor.

This invention further provides a process for determining whether a chemical compound specifically binds to and inhibits activation of a mammalian NMU receptor, which comprises separately contacting cells producing a second messenger response and expressing on their cell surface the mammalian NMU receptor, wherein such cells do not normally express the mammalian NMU receptor, with both the chemical compound and a second chemical compound known to activate the mammalian NMU receptor, and with only the second chemical compound, under conditions suitable for activation of the mammalian NMU receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the mammalian NMU receptor.

This invention provides a method of screening a plurality of chemical compounds not known to activate a mammalian SNORF62 receptor to identify a compound which activates the mammalian SNORF62 receptor which comprises: (a) contacting cells transfected with and expressing the mammalian SNORF62 receptor with the plurality of compounds not known to activate the mammalian SNORF62 receptor, under conditions permitting activation of the mammalian SNORF62 receptor; (b) determining whether the activity of the mammalian SNORF62 receptor is increased in the presence of one or more of the compounds; and if so (c) separately determining whether the activation of the mammalian SNORF62 receptor is increased by any compound included in the plurality of compounds, so as to thereby identify each compound which activates the mammalian SNORF62 receptor.

This invention also provides a method of screening a plurality of chemical compounds not known to activate a mammalian SNORF72 receptor to identify a compound which activates the mammalian SNORF72 receptor which comprises: (a) contacting cells transfected with and expressing the mammalian SNORF72 receptor with the plurality of compounds not known to activate the mammalian SNORF72 receptor, under conditions permitting activation of the mammalian SNORF72 receptor; (b) determining whether the activity of the mammalian SNORF72 receptor is increased in the presence of one or more of the compounds; and if so (c) separately determining whether the activation of the mammalian SNORF72 receptor is increased by any compound included in the plurality of compounds, so as to thereby identify each compound which activates the mammalian SNORF72 receptor.

This invention further provides a method of screening a plurality of chemical compounds not known to inhibit the activation of a mammalian NMU receptor to identify a compound which inhibits the activation of the mammalian NMU receptor, which comprises: (a) contacting cells transfected with and expressing the mammalian NMU receptor with the plurality of compounds in the presence of a known mammalian NMU receptor agonist, under conditions permitting activation of the mammalian NMU receptor; (b) determining whether the extent or amount of activation of the mammalian NMU receptor is reduced in the presence of one or more of the compounds, relative to the extent or amount of activation of the mammalian NMU receptor in the absence of such one or more compounds; and if so (c) separately determining whether each such compound inhibits activation of the mammalian NMU receptor for each compound included in the plurality of compounds, so as to thereby identify any compound included in such plurality of compounds which inhibits the activation of the mammalian NMU receptor.

This invention still further provides a method of screening a plurality of chemical compounds not known to inhibit the activation of a mammalian SNORF72 receptor to identify a compound which inhibits the activation of the mammalian SNORF72 receptor, which comprises: (a) contacting cells transfected with and expressing the mammalian SNORF72 receptor with the plurality of compounds in the presence of a known mammalian SNORF72 receptor agonist, under conditions permitting activation of the mammalian SNORF72 receptor; (b) determining whether the extent or amount of activation of the mammalian SNORF72 receptor is reduced in the presence of one or more of the compounds, relative to the extent or amount of activation of the mammalian SNORF72 receptor in the absence of such one or more compounds; and if so (c) separately determining whether each such compound inhibits activation of the mammalian SNORF72 receptor for each compound included in the plurality of compounds, so as to thereby identify any compound included in such plurality of compounds which inhibits the activation of the mammalian SNORF72 receptor.

This invention additionally provides a method of treating an abnormality in a subject wherein the abnormality is alleviated by increasing the activity of a mammalian SNORF62 receptor which comprises administering to the subject a compound which is a mammalian SNORF62 receptor agonist in an amount effective to treat the abnormality.

This invention also provides a method of treating an abnormality in a subject wherein the abnormality is alleviated by increasing the activity of a mammalian SNORF72 receptor which comprises administering to the subject a compound which is a mammalian SNORF72 receptor agonist in an amount effective to treat the abnormality.

This invention further provides a method of treating an abnormality in a subject wherein the abnormality is alleviated by decreasing the activity of a mammalian SNORF62 receptor which comprises administering to the subject a compound which is a mammalian SNORF62 receptor antagonist in an amount effective to treat the abnormality.

This invention still further provides a method of treating ! an abnormality in a subject wherein the abnormality is alleviated by decreasing the activity of a mammalian SNORF72 receptor which comprises administering to the subject a compound which is a mammalian SNORF72 receptor antagonist in an amount effective to treat the abnormality.

BRIEF DESCRIPTION OF THE FIGURES

FIGS. 1A–1B

Nucleotide sequence including sequence encoding a human SNORF62 receptor (SEQ ID NO: 1). Putative open reading frames including the longest and shortest open reading frames are indicated by underlining two start (ATG) codons (at positions 38–40 and 107–109) and the stop codon (at positions 1316–1318). In addition, partial 5' and 3' untranslated sequences are shown.

FIGS. 2A–2B

Deduced amino acid sequence (SEQ ID NO: 2) of the human SNORF62 receptor encoded by the longest open reading frame indicated in the nucleotide sequence shown in FIGS. 1A–1B (SEQ ID NO: 1). The seven putative transmembrane (TM) regions are underlined.

FIGS. 3A–3B

Nucleotide sequence including sequence encoding a human SNORF72 receptor (SEQ ID NO: 3). Putative open reading frames including the longest and shortest open reading frames are indicated by underlining two start (ATG) codons (at positions 27–29 and 36–38) and the stop codon (at positions 1272–1274). In addition, partial 5' and 3' untranslated sequences are shown.

FIGS. 4A–4B

Deduced amino acid sequence (SEQ ID NO: 4) of the human SNORF72 receptor encoded by the longest open reading frame indicated in the nucleotide sequence shown in FIGS. 3A–3B (SEQ ID NO: 3). The seven putative transmembrane (TM) regions are underlined.

FIG. 5

Pairwise GAP comparison (Wisconsin Package, Genetics Computer Group, Madison, Wis.) of the amino acid sequences of SNORF62(upper sequence) and SNORF72 (lower sequence). (|) Indicates identical residues, and (:) or (.) indicate varying degrees of conservation between residues.

FIG. 6

Concentration-dependent stimulation of intracellular $Ca^{2+}$ release by human NMU-25 in DNA vector (Mock)- and SNORF62-transfected COS-7 cells. The data presented are representative of 7 experiments performed in duplicate.

FIG. 7

Concentration-dependent stimulation of intracellular $Ca^{2+}$ release by human NMU-25 in SNORF72-transfected COS-7 cells.

The data presented are representative of 2 experiments performed in duplicate.

FIG. 8

Stimulation of intracellular $Ca^{2+}$ release by NMU and related peptides (300 nM) in SNORF72-transfected COS-7 cells. The data presented are representative of 2 experiments performed in duplicate.

Figure 9A:
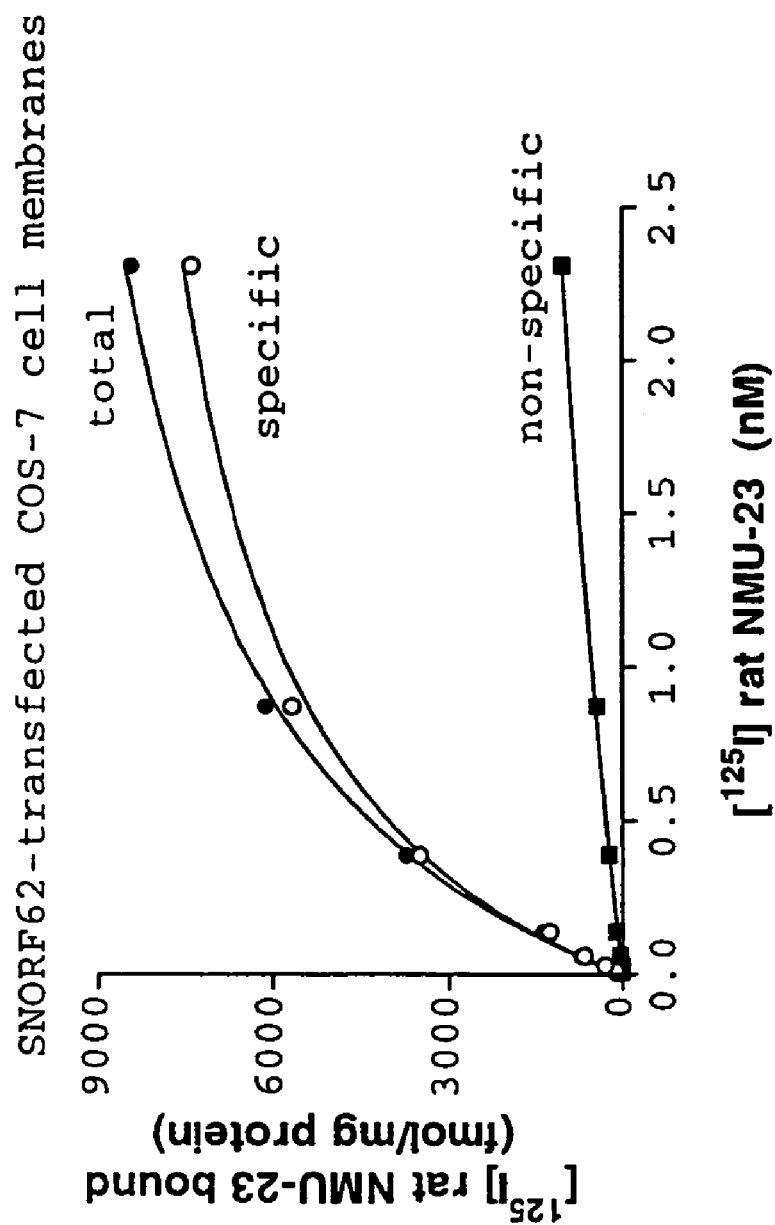
Figure 9B:
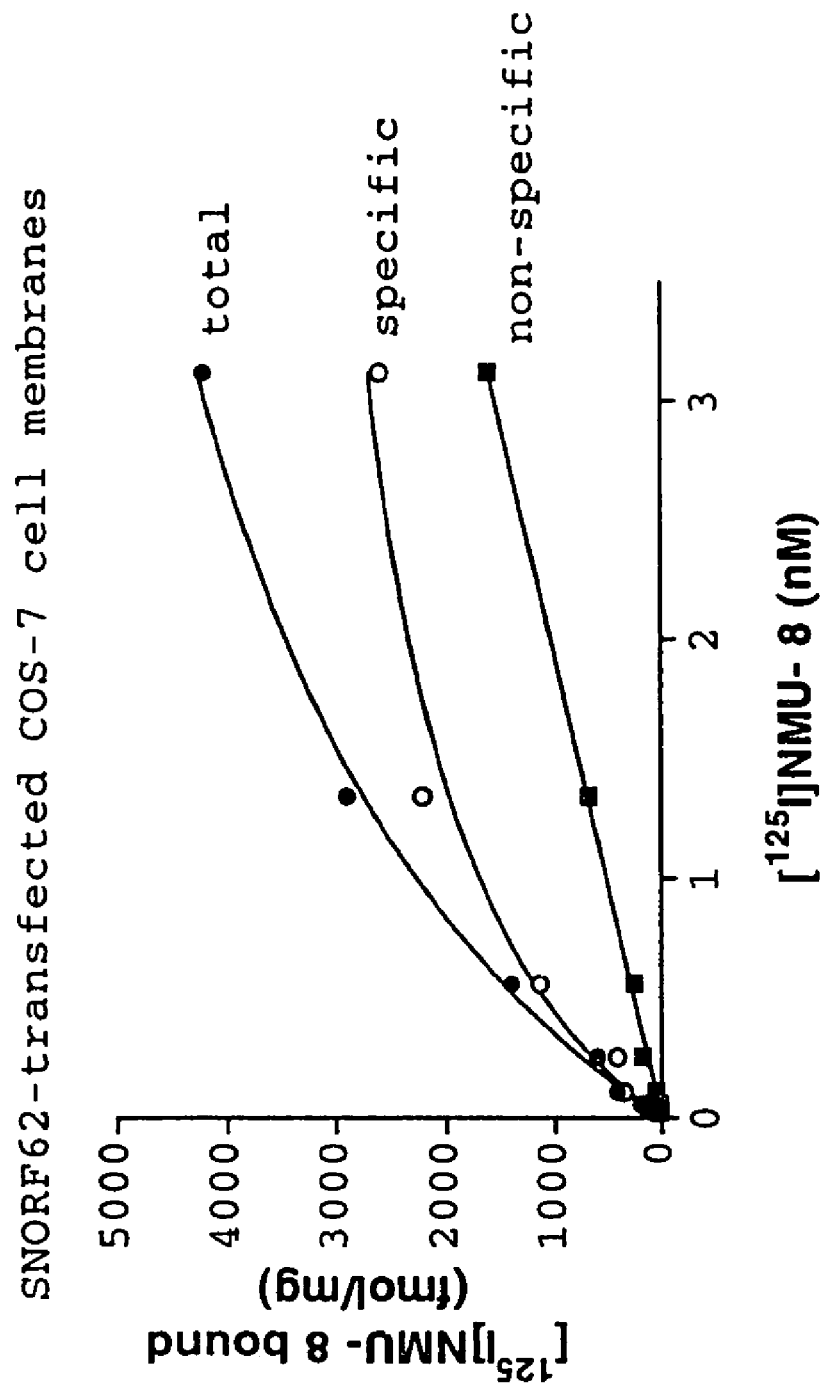

FIGS. 9A and 9B Saturation binding of [$^{125}$I]rat NMU-23 and [$^{125}$I]NMU-8 to SNORF62. COS-7 cells were transiently transfected with SNORF62 and membranes were prepared as described in Materials and Methods. Membranes (5–20 μg protein) were incubated at 4° C. with increasing concentrations of [$^{125}$I]rat NMU-23 (FIG. 9A) or [$^{125}$I]NMU-8 (FIG. 9B) (0.01–3 nM) for 60 minutes. Non-specific binding was determined in the presence of 100 nM rat NMU-23. Results are representative of 2 experiments performed in duplicate.

FIG. 10

Displacement of [$^{125}$I]-rat NMU-23 binding in SNORF62-transfected COS-7 membranes. Membranes were incubated with [$^{125}$I]-rat NMU-23 (0.05–0.1 nM) in the presence of the indicated peptides as described in Materials and Methods. Results presented are representative of 2 experiments.

Figure 11A:
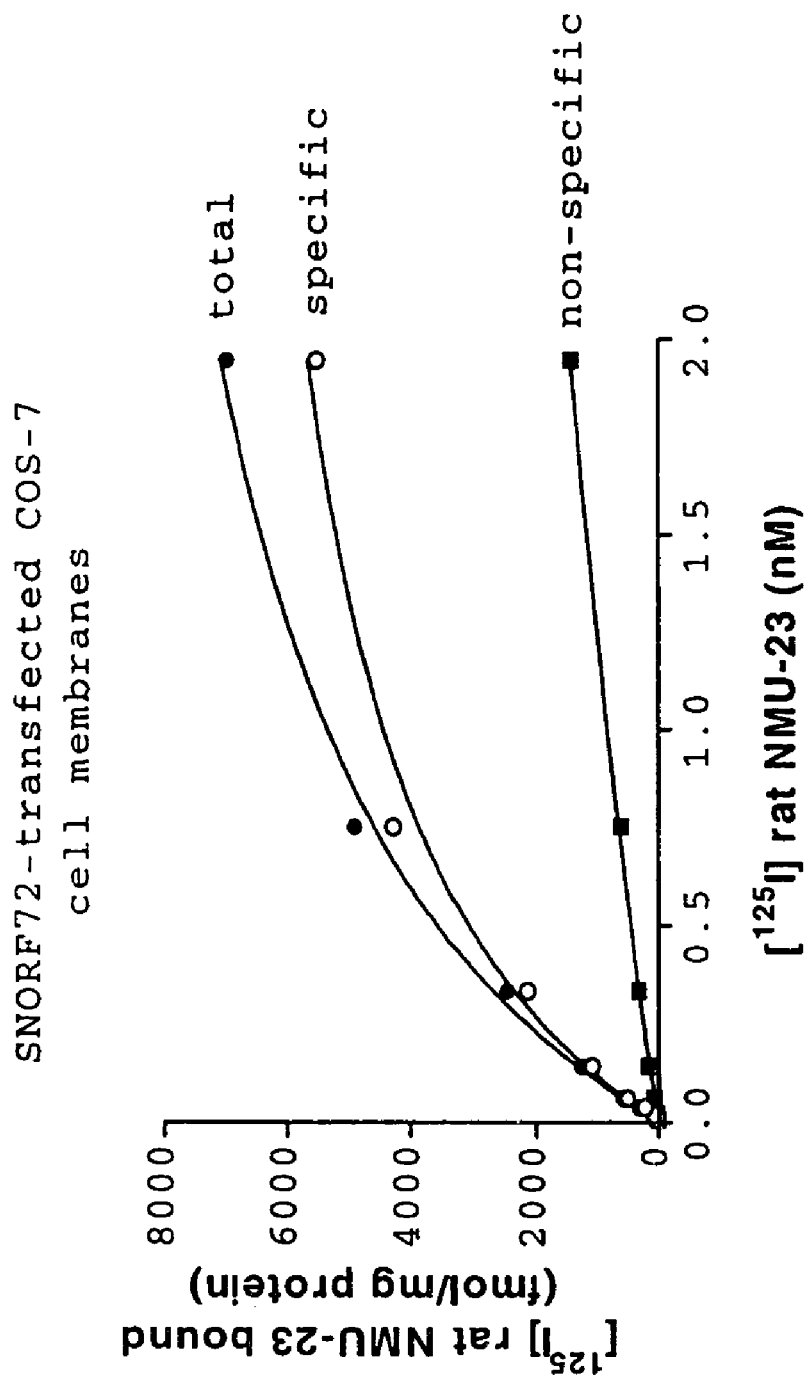
Figure 11B:
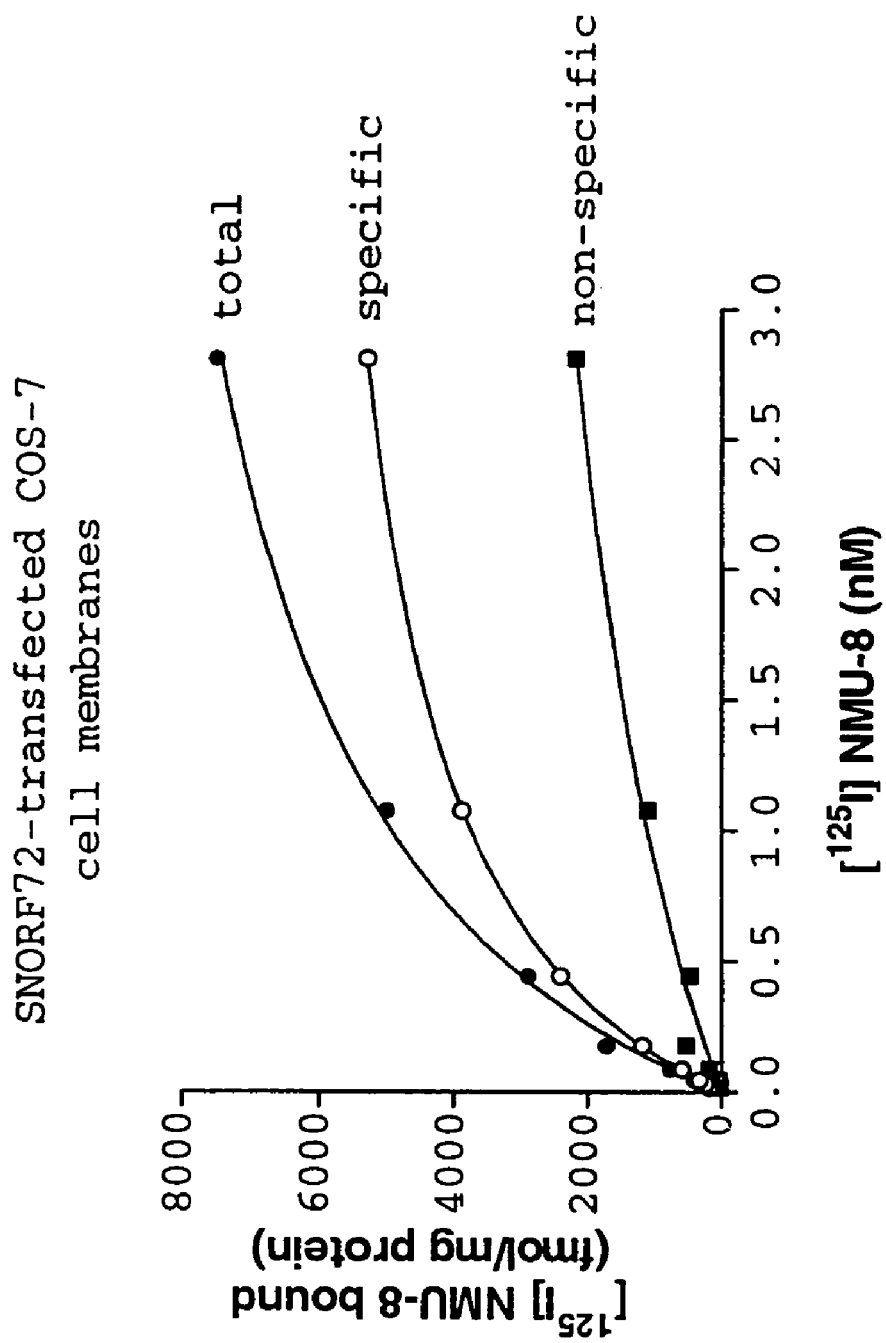

FIGS. 11A and 11B

Saturation binding of [$^{125}$I]rat NMU-23 and [$^{125}$I]NMU-8 to SNORF72. COS-7 cells were transiently transfected with SNORF72 and membranes were prepared as described in Materials and Methods. Membranes (5–20 μg protein) were incubated at 4° C. with increasing concentrations of [$^{125}$I]rat NMU-23 (FIG. 11A) or [$^{125}$I]NMU-8 (FIG. 11B) (0.01–2.8 nM) for 60 minutes. Non-specific binding was determined in the presence of 100 nM rat NMU-23. Results presented are representative of 2 experiments performed in duplicate.

FIG. 12

Displacement of [$^{125}$I]rat NMU-23 binding in SNORF72-transfected COS-7 membranes. Membranes were incubated with [$^{125}$I]rat NMU-23 (0.05–0.1 nM) in the presence of the indicated peptides as described in Materials and Methods. Results are representative of 2 experiments performed in duplicate.

FIG. 13

Representative traces of human NMU-25-induced calcium-activated chloride currents in Xenopus laevis oocytes.

The traces labeled SNORF62 were recorded from oocytes injected with mRNA encoding SNORF62.

FIGS. 14A–14B

Nucleotide sequence including sequence encoding a rat SNORF72 receptor (SEQ ID NO: 24). Putative open reading frames including the longest and shortest open reading frames are indicated by underlining two start (ATG) codons (at positions 23–25 and 65–67) and the stop codon (at positions 1208–1210). In addition, partial 5' and 3' untranslated sequences are shown.

FIGS. 15A–15B

Deduced amino acid sequence (SEQ ID NO: 25) of the rat SNORF72 receptor encoded by the longest open reading frame indicated in the nucleotide sequence shown in FIGS. 14A–14B (SEQ ID NO: 24). The seven putative transmembrane (TM) regions are underlined.

FIGS. 16A–16B

Amino acid sequence comparison of rat SNORF72 (SEQ ID NO: 25) with human SNORF72 (SEQ ID NO: 4) and human SNORF62 (SEQ ID NO: 2). The multiple sequence alignment was generated using Pileup (Wisconsin Package Version 10.0, Genetics Computer Group (GCG), Madison, Wisc.).

FIGS. 17A and 17B

Nucleotide sequence including sequence encoding a rat SNORF62a receptor (SEQ ID NO: 26). Putative open reading frames are indicated by underlining the start (ATG) codon (at positions 26–28) and the stop codon (at positions 1265–1267). In addition, partial 5' and 3' untranslated sequences are shown.

Figure 18A:
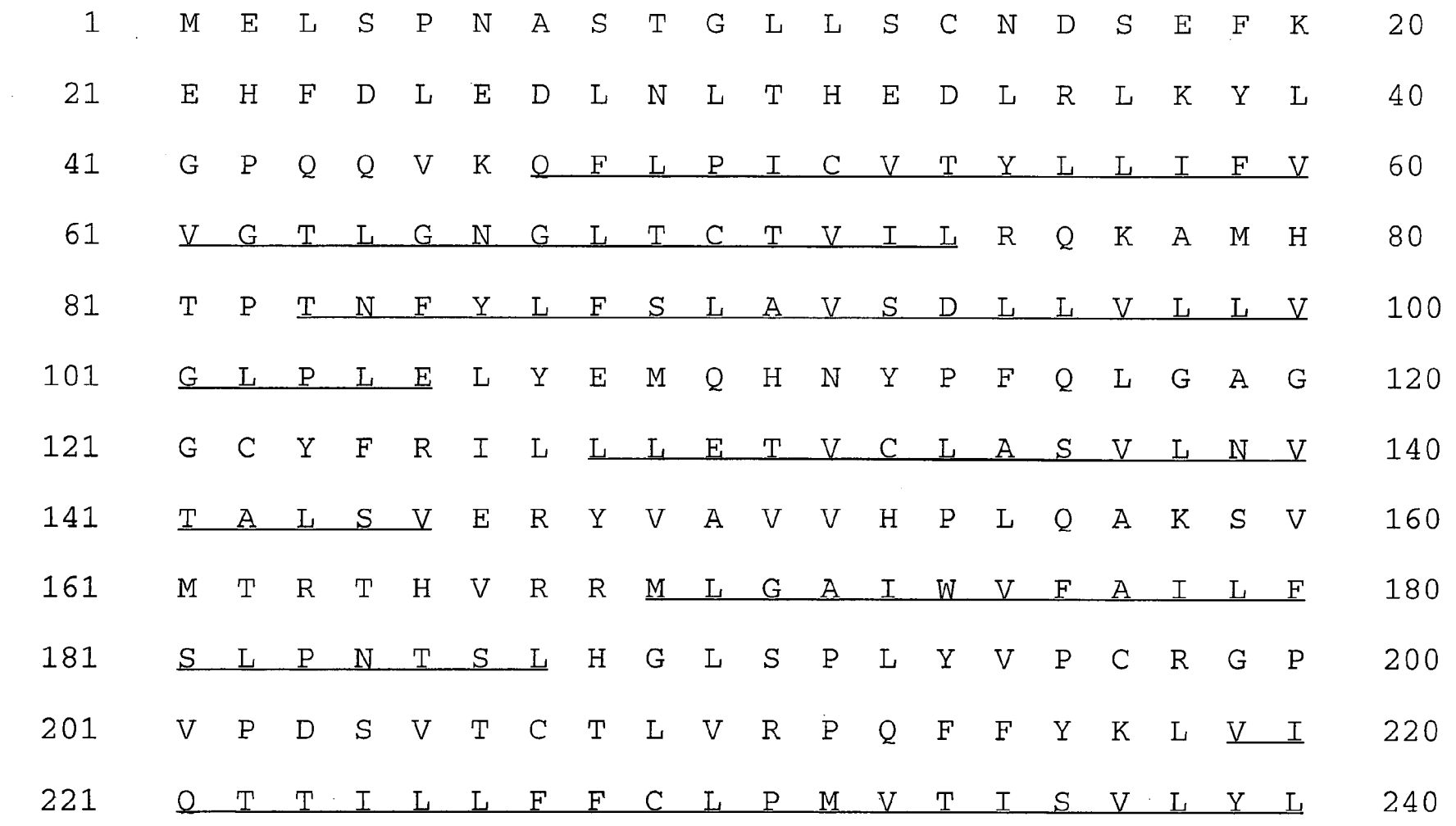
Figure 18B:
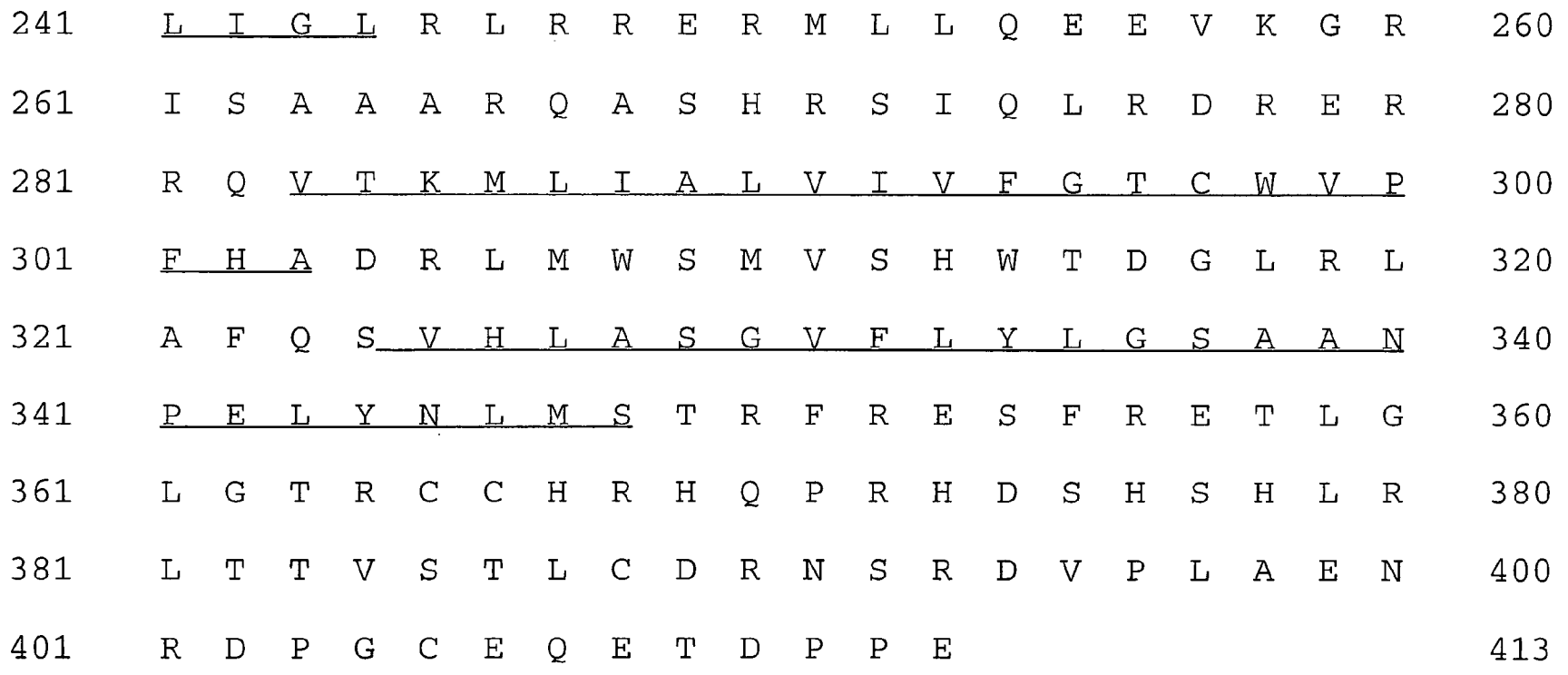

FIGS. 18A and 18B

Deduced amino acid sequence (SEQ ID NO: 27) of the rat SNORF62a receptor encoded by the longest open reading frame indicated in the nucleotide sequence shown in FIGS. 17A–17B (SEQ ID NO: 26). The seven putative transmembrane (TM) regions are underlined.

FIGS. 19A and 19B

Nucleotide sequence including sequence encoding a rat SNORF62b receptor (SEQ ID NO: 28). Putative open reading frames including the longest and shortest open reading frames are indicated by underlining two start (ATG) codons (at positions 27–29 and 69–71) and the stop codon (at position 1344–1346). In addition, partial 5' and 3' untranslated sequences are shown.

Figure 20A:
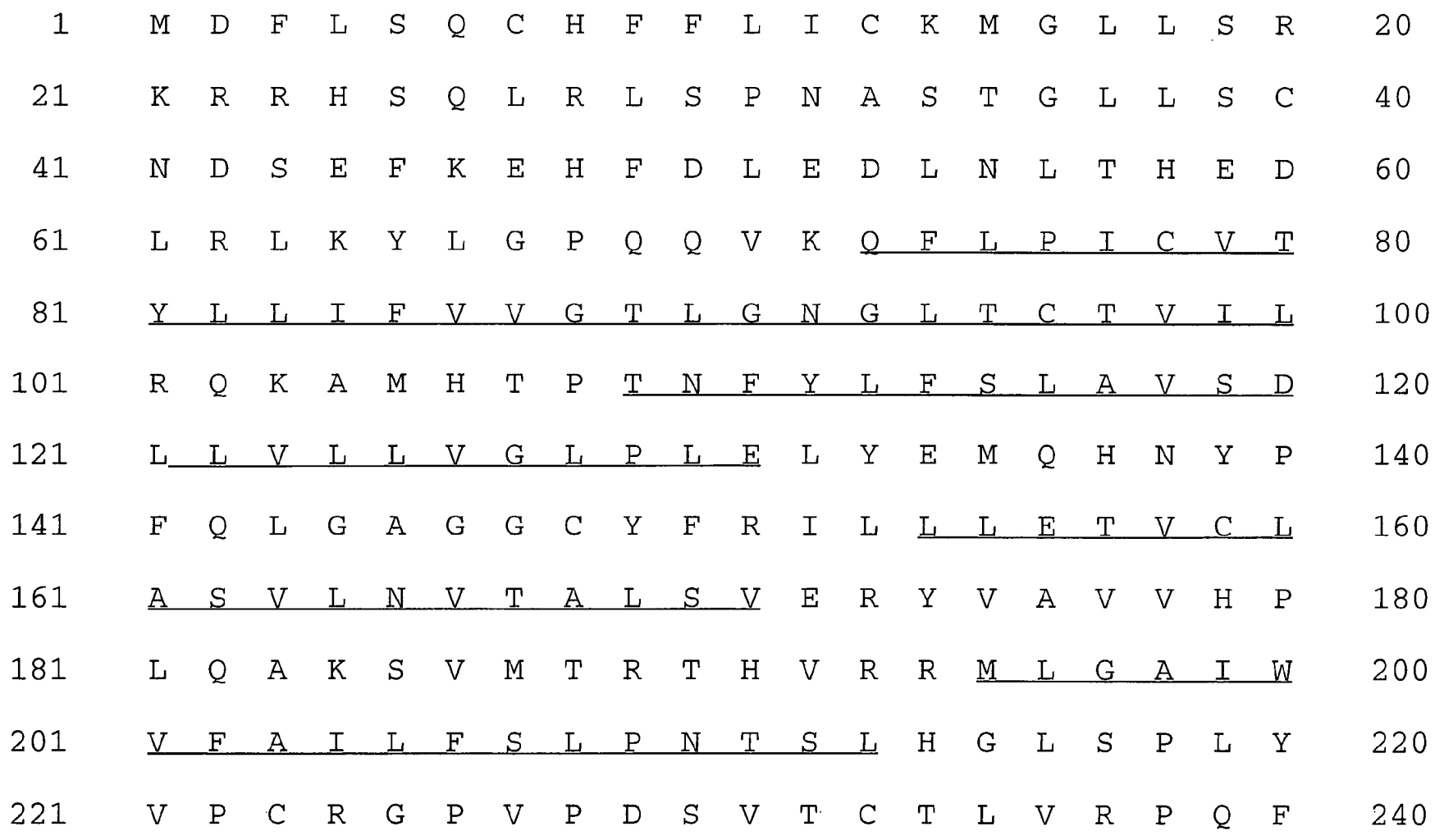
Figure 20B:
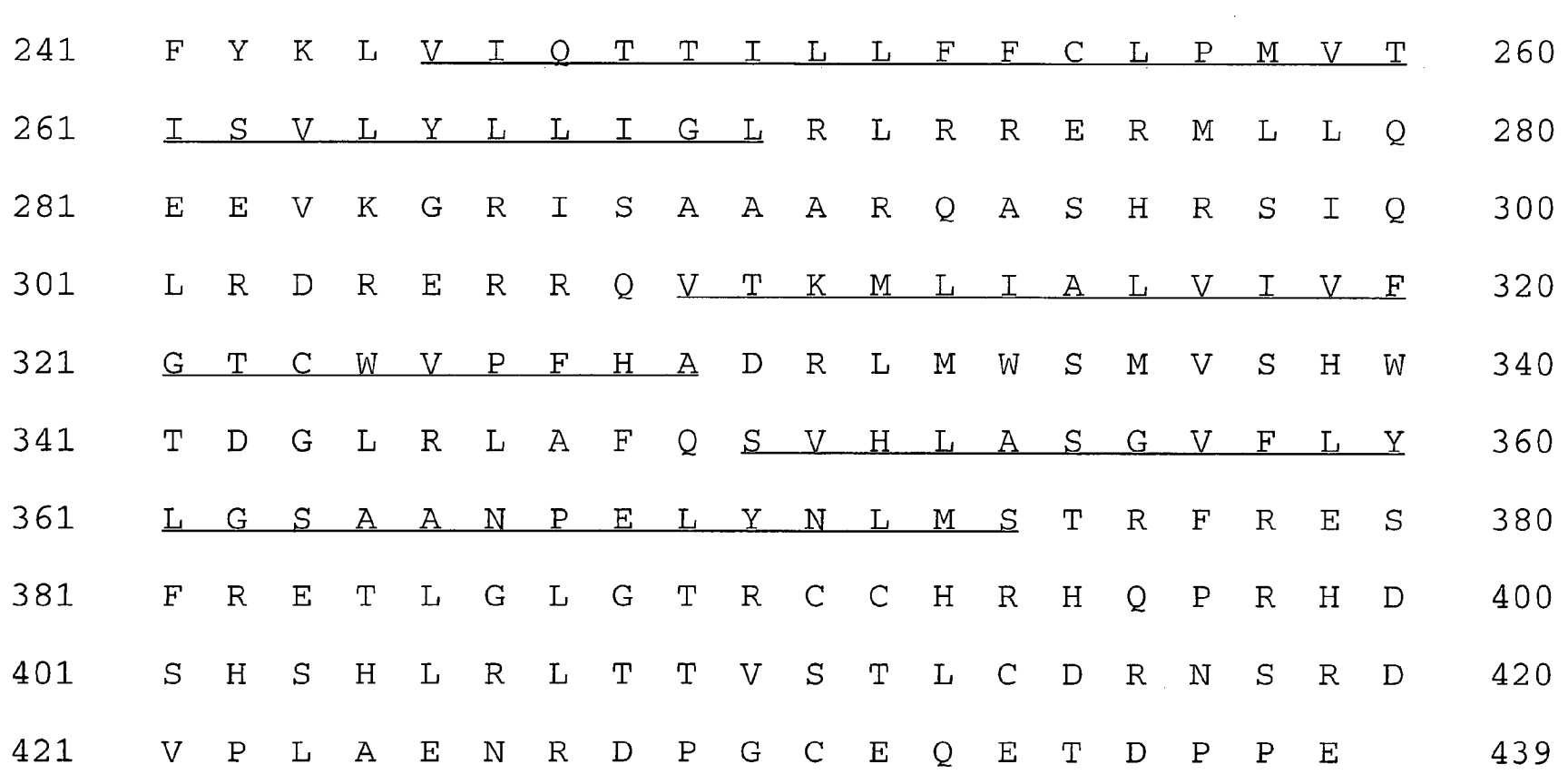

FIGS. 20A and 20B

Deduced amino acid sequence of the rat SNORF62b receptor (SEQ ID NO: 29) encoded by the longest open reading frame indicated in the nucleotide sequence shown in FIGS. 19A–19B. The seven putative transmembrane (TM) regions are underlined.

FIGS. 21A–21C

Amino acid sequence comparison of rat SNORF62a (SEQ ID NO: 27), rat SNORF62b (SEQ ID NO: 29) and human SNORF62 (SEQ ID NO: 2). The multiple sequence alignment was generated using Pileup (Wisconsin Package Version 10.0, Genetics Computer Group (GCG), Madison, Wisc.).

FIG. 22

Stimulation of intracellular $Ca^{2+}$ release by NMU-8 and rat NMU-23 at 100 nM in rat SNORF72-transfected COS-7 cells. The data represent the average± SEM for an experiment performed in quadruplicate.

FIG. 23

Concentration-dependent stimulation of inositol phosphate (IP) second messenger release by human NMU-25 in SNORF62-transfected and mock-transfected Cos-7 cells. The data presented are representative of 3 experiments performed in triplicate.

DETAILED DESCRIPTION OF THE INVENTION

This invention provides a recombinant nucleic acid comprising a nucleic acid encoding a mammalian SNORF62 receptor, wherein the mammalian receptor-encoding nucleic acid hybridizes under high stringency conditions to a nucleic acid encoding a human SNORF62 receptor and having a sequence identical to the sequence of the human SNORF62 receptor-encoding nucleic acid contained in plasmid pEXJ.T3T7-hSNORF62-f (Patent Deposit Designation No. PTA-1042).

This invention further provides a recombinant nucleic acid comprising a nucleic acid encoding a human SNORF62 receptor, wherein the human SNORF62 receptor comprises an amino acid sequence identical to the sequence of the human SNORF62 receptor encoded by the longest open reading frame indicated in FIGS. 1A–1B (SEQ ID NO: 1).

The plasmid pEXJ.T3T7-hSNORF62-f was deposited on Dec. 8, 1999, with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure and was accorded Patent Deposit Designation No. PTA-1042.

This invention further provides a recombinant nucleic acid comprising a nucleic acid encoding a mammalian SNORF72 receptor, wherein the mammalian receptor-encoding nucleic acid hybridizes under high stringency conditions to a nucleic acid encoding a human SNORF72 receptor and having a sequence identical to the sequence of the human SNORF72 receptor-encoding nucleic acid contained in plasmid pEXJ.T3T7-hSNORF72-f (Patent Deposit Designation No. PTA- 1446).

This invention further provides a recombinant nucleic acid comprising a nucleic acid encoding a human SNORF72 receptor, wherein the human SNORF72 receptor comprises an amino acid sequence identical to the sequence of the human SNORF72 receptor encoded by the longest open reading frame indicated in FIGS. 3A–3B (SEQ ID NO: 3).

The plasmid pEXJ.T3T7-hSNORF72-f was deposited on Mar. 2, 2000, with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure and was accorded Patent Deposit Designation No. PTA-1446.

The plasmid pEXJ.BS-rSNORF72-f was deposited on May 26, 2000, with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure and was accorded Patent Deposit Designation No. PTA-1927.

This invention also contemplates recombinant nucleic acids which comprise nucleic acids encoding naturally occurring allelic variants of the mammalian SNORF62 and mammalian SNORF72 receptors described above.

Hybridization methods are well known to those of skill in the art. For purposes of this invention, hybridization under high stringency conditions means hybridization performed at 40° C. in a hybridization buffer containing 50% formamide, 5×SSC, 7 mM Tris, 1× Denhardt's, 25 µg/ml salmon sperm DNA; wash at 50° C. in 0.1×SSC, 0.1% SDS.

Throughout this application, the following standard abbreviations are used to indicate specific nucleotide bases:
A=adenine
G=guanine
C=cytosine
T=thymine
M=adenine or cytosine
R=adenine or guanine
W=adenine or thymine
S=cytosine or guanine
Y=cytosine or thymine
K=guanine or thymine
V=adenine, cytosine, or guanine (not thymine)
H=adenine, cytosine, or thymine (not cytosine)
B=cytosine, guanine, or thymine (not adenine)
N=adenine, cytosine, guanine, or thymine (or other modified base such as inosine)
I=inosine Furthermore, the term "agonist" is used throughout this application to indicate any peptide or non-peptidyl compound which increases the activity of any of the polypeptides of the subject invention. The term "antagonist" is used throughout this application to indicate any peptide or non-peptidyl compound which decreases the activity of any of the polypeptides of the subject invention.

Furthermore, as used herein, the phrase "pharmaceutically acceptable carrier" means any of the standard pharmaceutically acceptable carriers. Examples include, but are not limited to, phosphate buffered saline, physiological saline, water, and emulsions, such as oil/water emulsions.

It is possible that the mammalian SNORF62 receptor gene and the mammalian SNORF72 receptor gene contain introns and furthermore, the possibility exists that additional introns could exist in coding or non-coding regions. In addition, spliced form(s) of mRNA may encode additional amino acids either upstream of the currently defined starting methionine or within the coding region. Further, the existence and use of alternative exons is possible, whereby the mRNA may encode different amino acids within the region comprising the exon. In addition, single amino acid substitutions may arise via the mechanism of RNA editing such that the amino acid sequence of the expressed protein is different than that encoded by the original gene. (Burns, et al., 1996; Chu, et al., 1996). Such variants may exhibit pharmacologic properties differing from the polypeptide encoded by the original gene.

This invention provides splice variants of the mammalian SNORF62 and SNORF72 receptors disclosed herein. This invention further provides for alternate translation initiation sites and alternately spliced or edited variants of nucleic acids encoding the mammalian SNORF62 and SNORF72 receptors of this invention.

The nucleic acids of the subject invention also include nucleic acid analogs of the human SNORF62 receptor gene, wherein the human SNORF62 receptor gene comprises the nucleic acid sequence shown in FIGS. 1A–1B (SEQ ID NO: 1) or contained in plasmid pEXJ.T3T7-hSNORF62-f (Patent Deposit Designation No. PTA-1042). Nucleic acid analogs of the human SNORF62 receptor genes differ from the human SNORF62 receptor genes described herein in terms of the identity or location of one or more nucleic acid bases (deletion analogs containing less than all of the nucleic acid bases shown in FIGS. 1A–1B or contained in plasmid pEXJ.T3T7-hSNORF62-f, substitution analogs wherein one or more nucleic acid bases shown in FIGS. 1A–1B or contained in plasmid pEXJ.T3T7-hSNORF62-f (Patent Deposit Designation No. PTA-1042), are replaced by other nucleic acid bases, and addition analogs, wherein one or more nucleic acid bases are added to a terminal or medial portion of the nucleic acid sequence) and which encode proteins which share some or all of the properties of the proteins encoded by the nucleic acid sequences shown in FIGS. 1A–1B or contained in plasmid pEXJ.T3T7-hS-NORF62-f (Patent Deposit Designation No. PTA-1042). In one embodiment of the present invention, the nucleic acid analog encodes a protein which has an amino acid sequence identical to that shown in FIGS. 2A–2B or encoded by the nucleic acid sequence contained in plasmid pEXJ.T3T7-hSNORF62-f (Patent Deposit Designation No. PTA-1042). In another embodiment, the nucleic acid analog encodes a protein having an amino acid sequence which differs from the amino acid sequences shown in FIGS. 2A–2B or encoded by the nucleic acid contained in plasmid pEXJ.T3T7-hSNORF62-f (Patent Deposit Designation No. PTA-1042). In a further embodiment, the protein encoded by the nucleic acid analog has a function which is the same as the function of the receptor proteins having the amino acid sequence shown in FIGS. 2A–2B. In another embodiment, the function of the protein encoded by the nucleic acid analog differs from the function of the receptor protein having the amino acid sequence shown in FIGS. 2A–2B. In another embodiment, the variation in the nucleic acid sequence occurs within the transmembrane (TM) region of the protein. In a further embodiment, the variation in the nucleic acid sequence occurs outside of the TM region.

The nucleic acids of the subject invention also include nucleic acid analogs of the rat SNORF62a and rat SNORF62b receptor genes, wherein the rat SNORF62a receptor gene comprises the nucleic acid sequence shown in FIGS. 17A–17B (SEQ ID NO: 26) and the rat SNORF62b receptor gene comprises the nucleic acid sequence shown in FIGS. 19A–19B (SEQ ID NO: 28). Nucleic acid analogs of the rat SNORF62a and rat SNORF62b receptor genes differ from the rat SNORF62a and rat SNORF62b receptor genes described herein in terms of the identity or location of one or more nucleic acid bases (deletion analogs containing less than all of the nucleic acid bases shown in FIGS. 17A–17B or FIGS. 19A–19B, substitution analogs wherein one or more nucleic acid bases shown in FIGS. 17A–17B or FIGS. 19A–19B, are replaced by other nucleic acid bases, and addition analogs, wherein one or more nucleic acid bases are added to a terminal or medial portion of the nucleic acid sequence) and which encode proteins which share some or all of the properties of the proteins encoded by the nucleic acid sequences shown in FIGS. 17A–17B or FIGS. 19A–19B. In one embodiment of the present invention, the nucleic acid analog encodes a protein which has an amino acid sequence identical to that shown in FIGS. 18A–18B or FIGS. 20A–20B. In another embodiment, the nucleic acid analog encodes a protein having an amino acid sequence which differs from the amino acid sequences shown in FIGS. 18A–18B or FIGS. 20A–20B. In a further embodiment, the protein encoded by the nucleic acid analog has a function which is the same as the function of the receptor proteins having the amino acid sequence shown in FIGS. 18A–18B or FIGS. 20A–20B. In another embodiment, the function of the protein encoded by the nucleic acid analog differs from the function of the receptor protein having the amino acid sequence shown in FIGS. 18A–18B or FIGS. 20A–20B. In another embodiment, the variation in the nucleic acid sequence occurs within the transmembrane (TM) region of the protein. In a further embodiment, the variation in the nucleic acid sequence occurs outside of the TM region.

The nucleic acids of the subject invention also include nucleic acid analogs of the human SNORF72 receptor gene, wherein the human SNORF72 receptor gene comprises the nucleic acid sequence shown in FIGS. 3A–3B (SEQ ID NO: 3) or contained in plasmid pEXJ.T3T7-hSNORF72-f (Patent Deposit Designation No. PTA-1446). Nucleic acid analogs of the human SNORF72 receptor gene differ from the human SNORF72 receptor gene described herein in terms of the identity or location of one or more nucleic acid bases (deletion analogs containing less than all of the nucleic acid bases shown in FIGS. 3A–3B or contained in plasmid pEXJ.T3T7-hSNORF72-f (Patent Deposit Designation No. PTA-1446), substitution analogs wherein one or more nucleic acid bases shown in FIGS. 3A–3B or contained in plasmid pEXJ.T3T7-hSNORF72-f (Patent Deposit Designation No. PTA-1446), are replaced by other nucleic acid bases, and addition analogs, wherein one or more nucleic acid bases are added to a terminal or medial portion of the nucleic acid sequence) and which encode proteins which share some or all of the properties of the proteins encoded by the nucleic acid sequences shown in FIGS. 3A–3B or contained in plasmid pEXJ.T3T7-hSNORF72-f (Patent Deposit Designation No. PTA-1446). In one embodiment of the present invention, the nucleic acid analog encodes a protein which has an amino acid sequence identical to that shown in FIGS. 4A–4B or encoded by the nucleic acid sequence contained in plasmid pEXJ.T3T7-hSNORF72-f (Patent Deposit Designation No. PTA-1446). In another embodiment, the nucleic acid analog encodes a protein having an amino acid sequence which differs from the amino acid sequences shown in FIGS. 4A–4B or encoded by the nucleic acid contained in plasmid pEXJ.T3T7-hSNORF72-f (Patent Deposit Designation No. PTA-1446). In a further embodiment, the protein encoded by the nucleic acid analog has a function which is the same as the function of the receptor proteins having the amino acid sequence shown in FIGS. 4A–4B. In another embodiment, the function of the protein encoded by the nucleic acid analog differs from the function of the receptor protein having the amino acid sequence shown in FIGS. 4A–4B. In another embodiment, the variation in the nucleic acid sequence occurs within the transmembrane (TM) region of the protein. In a further embodiment, the variation in the nucleic acid sequence occurs outside of the TM region.

The nucleic acids of the subject invention also include nucleic acid analogs of the rat SNORF72 receptor gene, wherein the rat SNORF72 receptor gene comprises the nucleic acid sequence shown in FIGS. 14A–14B (SEQ ID NO: 24) or contained in plasmid pEXJ.BS-rSNORF72-f (Patent Deposit Designation No. PTA-1927). Nucleic acid analogs of the rat SNORF72 receptor gene differ from the rat SNORF72 receptor gene described herein in terms of the identity or location of one or more nucleic acid bases (deletion analogs containing less than all of the nucleic acid bases shown in FIGS. 14A–14B or contained in plasmid pEXJ.BS-rSNORF72-f (Patent Deposit Designation No. PTA-1927), substitution analogs wherein one or more nucleic acid bases shown in FIGS. 14A–14B or contained in plasmid pEXJ.BS-rSNORF72-f (Patent Deposit Designation No. PTA-1927), are replaced by other nucleic acid bases, and addition analogs, wherein one or more nucleic acid bases are added to a terminal or medial portion of the nucleic acid sequence) and which encode proteins which share some or all of the properties of the proteins encoded by the nucleic acid sequences shown in FIGS. 14A–14B or contained in plasmid pEXJ.BS-rSNORF72-f (Patent Deposit Designation No. PTA-1927). In one embodiment of the present invention, the nucleic acid analog encodes a protein which has an amino acid sequence identical to that shown in FIGS. 15A–15B or encoded by the nucleic acid sequence contained in plasmid pEXJ.BS-rSNORF72-f (Patent Deposit Designation No. PTA-1927). In another embodiment, the nucleic acid analog encodes a protein having an amino acid sequence which differs from the amino acid sequences shown in FIGS. 15A–15B or encoded by the nucleic acid contained in plasmid pEXJ.BS-rSNORF72-f (Patent Deposit Designation No. PTA-1927). In a further embodiment, the protein encoded by the nucleic acid analog has a function which is the same as the function of the receptor proteins having the amino acid sequence shown in FIGS. 15A–15B. In another embodiment, the function of the protein encoded by the nucleic acid analog differs from the function of the receptor protein having the amino acid sequence shown in FIGS. 15A–15B. In another embodiment, the variation in the nucleic acid sequence occurs within the transmembrane (TM) region of the protein. In a further embodiment, the variation in the nucleic acid sequence occurs outside of the TM region.

This invention provides the above-described isolated nucleic acid, wherein the nucleic acid is DNA. In an embodiment, the DNA is cDNA. In another embodiment, the DNA is genomic DNA. In still another embodiment, the nucleic acid is RNA.

Methods for production and manipulation of nucleic acid molecules are well known in the art.

This invention further provides nucleic acid which is degenerate with respect to the DNA encoding any of the polypeptides described herein. In an embodiment, the nucleic acid comprises a nucleotide sequence which is degenerate with respect to the nucleotide sequence shown in FIGS. 1A–1B (SEQ ID NO: 1) or the nucleotide sequence contained in the plasmid pEXJ.T3T7-hSNORF62-f (Patent Deposit Designation No. PTA-1042), that is, a nucleotide sequence which is translated into the same amino acid sequence. In another embodiment, the nucleic acid comprises a nucleotide sequence which is degenerate with respect to the nucleotide sequence shown in FIGS. 3A–3B (SEQ ID NO: 3) or the nucleotide sequence contained in the plasmid pEXJ.T3T7-hSNORF72-f (Patent Deposit Designation No. PTA-1446), that is, a nucleotide sequence which is translated into the same amino acid sequence. In a further embodiment, the nucleic acid comprises a nucleotide sequence which is degenerate with respect to the nucleotide sequence shown in FIGS. 14A–14B (SEQ ID NO: 24) or the nucleotide sequence contained in the plasmid pEXJ.BS-rSNORF72-f (Patent Deposit Designation No. PTA-1927), that is, a nucleotide sequence which is translated into the same amino acid sequence. In another embodiment, the nucleic acid comprises a nucleotide sequence which is degenerate with respect to the nucleotide sequence shown in FIGS. 17A–17B (SEQ ID NO: 26), that is, a nucleotide sequence which is translated into the same amino acid sequence. In yet another embodiment, the nucleic acid comprises a nucleotide sequence which is degenerate with respect to the nucleotide sequence shown in FIGS. 19A–19B (SEQ ID NO: 28) that is, a nucleotide sequence which is translated into the same amino acid sequence.

This invention also encompasses DNAs and cDNAs which encode amino acid sequences which differ from those of the polypeptides of this invention, but which should not produce phenotypic changes.

Alternately, this invention also encompasses DNAs, cDNAs, and RNAs which hybridize to the DNA, cDNA, and RNA of the subject invention. Hybridization methods are well known to those of skill in the art.

The nucleic acids of the subject invention also include nucleic acid molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs wherein one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors. The creation of polypeptide analogs is well known to those of skill in the art (Spurney, R. F. et al. (1997); Fong, T. M. et al. (1995); Underwood, D. J. et al. (1994); Graziano, M. P. et al. (1996); Guan X. M. et al. (1995)).

The modified polypeptides of this invention may be transfected into cells either transiently or stably using methods well-known in the art, examples of which are disclosed herein. This invention also provides for binding assays using the modified polypeptides, in which the polypeptide is expressed either transiently or in stable cell lines. This invention further provides a compound identified using a modified polypeptide in a binding assay such as the binding assays described herein.

The nucleic acids described and claimed herein are useful for the information which they provide concerning the amino acid sequence of the polypeptide and as products for the large scale synthesis of the polypeptides by a variety of recombinant techniques. The nucleic acid molecule is useful for generating new cloning and expression vectors, transformed and transfected prokaryotic and eukaryotic host cells, and new and useful methods for cultured growth of such host cells capable of expression of the polypeptide and related products.

This invention also provides an isolated nucleic acid encoding species homologs of the SNORF62 receptor encoded by the nucleic acid sequence shown in FIGS. 1A–1B (SEQ ID NO: 1) or encoded by the plasmid pEXJ.T3T7-hSNORF62-f (Patent Deposit Designation No. PTA-1042). In one embodiment, the nucleic acid encodes a mammalian SNORF62 receptor homolog which has substantially the same amino acid sequence as does the SNORF62 receptor encoded by the plasmid pEXJ.T3T7-hSNORF62-f (Patent Deposit Designation No. PTA-1042). In another embodiment, the nucleic acid encodes a mammalian SNORF62 receptor homolog which has above 75% amino acid identity to the SNORF62 receptor encoded by the plasmid pEXJ.T3T7-hSNORF62-f (Patent Deposit Designation No. PTA-1042); preferably above 85% amino acid identity to the SNORF62 receptor encoded by the plasmid pEXJ.T3T7-hSNORF62-f (Patent Deposit Designation No. PTA-1042); most preferably above 95% amino acid identity to the SNORF62 receptor encoded by the plasmid pEXJ.T3T7-hSNORF62-f (Patent Deposit Designation No. PTA-1042). In another embodiment, the mammalian SNORF62 receptor homolog has above 70% nucleic acid identity to the SNORF62 receptor gene contained in plasmid pEXJ.T3T7-hSNORF62-f (Patent Deposit Designation No. PTA-1042); preferably above 80% nucleic acid identity to the SNORF62 receptor gene contained in the plasmid pEXJ.T3T7-hSNORF62-f (Patent Deposit Designation No. PTA-1042); more preferably above 90% nucleic acid identity to the SNORF62 receptor gene contained in the plasmid pEXJ.T3T7-hSNORF62-f (Patent Deposit Designation No. PTA-1042). Examples of methods for isolating and purifying species homologs are described elsewhere (e.g., U.S. Pat. No. 5,602,024, WO94/14957, WO97/26853, WO98/15570).

This invention also provides an isolated nucleic acid encoding species homologs of the SNORF62 receptor encoded by the nucleic acid sequence shown in FIGS. 17A–17B (SEQ ID NO: 26) or FIGS. 19A–19B (SEQ ID NO: 28).

This invention also provides an isolated nucleic acid encoding species homologs of the SNORF72 receptors encoded by the nucleic acid sequence shown in FIGS. 3A–3B (SEQ ID NO: 3) or encoded by the plasmid pEXJ.T3T7-hSNORF72-f (Patent Deposit Designation No. PTA-1446). In one embodiment, the nucleic acid encodes a mammalian SNORF72 receptor homolog which has substantially the same amino acid sequence as does the SNORF72 receptor encoded by the plasmid pEXJ.T3T7-hSNORF72-f (Patent Deposit Designation No. PTA-1446). In another embodiment, the nucleic acid encodes a mammalian SNORF72 receptor homolog which has above 75% amino acid identity to the SNORF72 receptor encoded by the plasmid pEXJ.T3T7-hSNORF72-f (Patent Deposit Designation No. PTA-1446); preferably above 85% amino acid identity to the SNORF72 receptor encoded by the plasmid pEXJ.T3T7-hSNORF72-f (Patent Deposit Designation No. PTA-1446); most preferably above 95% amino acid identity to the SNORF72 receptor encoded by the plasmid pEXJ.T3T7-hSNORF72-f (Patent Deposit Designation No. PTA-1446). In another embodiment, the mammalian SNORF72 receptor homolog has above 70% nucleic acid identity to the SNORF72 receptor gene contained in plasmid pEXJ.T3T7-hSNORF72-f (Patent Deposit Designation No. PTA-1446); preferably above 80% nucleic acid identity to the SNORF72 receptor gene contained in the plasmid pEXJ.T3T7-hSNORF72-f (Patent Deposit Designation No. PTA-1446); more preferably above 90% nucleic acid identity to the SNORF72 receptor gene contained in the plasmid pEXJ.T3T7-hSNORF72-f (Patent Deposit Designation No. PTA-1446).

This invention also provides an isolated nucleic acid encoding species homologs of the SNORF72 receptors encoded by the nucleic acid sequence shown in FIGS. 14A–14B (SEQ ID NO:) or encoded by the plasmid pEXJ.BS-rSNORF72-f (Patent Deposit Designation No. PTA-1927). In one embodiment, the nucleic acid encodes a mammalian SNORF72 receptor homolog which has substantially the same amino acid sequence as does the SNORF72 receptor encoded by the plasmid pEXJ.BS-rS-NORF72-f (Patent Deposit Designation No. PTA-1927). In another embodiment, the nucleic acid encodes a mammalian SNORF72 receptor homolog which has above 75% amino acid identity to the SNORF72 receptor encoded by the plasmid pEXJ.BS-rSNORF72-f (Patent Deposit Designation No. PTA-1927); preferably above 85% amino acid identity to the SNORF72 receptor encoded by the plasmid pEXJ.BS-rSNORF72-f (Patent Deposit Designation No. PTA-1927); most preferably above 95% amino acid identity to the SNORF72 receptor encoded by the plasmid pEXJ.BS-rS-NORF72-f (Patent Deposit Designation No. PTA-1927). In another embodiment, the mammalian SNORF72 receptor homolog has above 70% nucleic acid identity to the SNORF72 receptor gene contained in plasmid pEXJ.BS-rSNORF72-f (Patent Deposit Designation No. PTA-1927); preferably above 80% nucleic acid identity to the SNORF72 receptor gene contained in the plasmid pEXJ.BS-rS-NORF72-f (Patent Deposit Designation No. PTA-1927); more preferably above 90% nucleic acid identity to the SNORF72 receptor gene contained in the plasmid pEXJ.BS-rSNORF72-f (Patent Deposit Designation No. PTA-1927).

This invention provides an isolated nucleic acid encoding a modified mammalian SNORF62 or SNORF72 receptor, which differs from a mammalian SNORF62 or SNORF72 receptor by having an amino acid(s) deletion, replacement, or addition in the third intracellular domain.

This invention provides an isolated nucleic acid encoding a mammalian NMU receptor. This invention provides an isolated nucleic acid encoding a mammalian SNORF62 receptor. This invention further provides an isolated nucleic acid encoding a mammalian SNORF72 receptor. In one embodiment, the nucleic acid is DNA. In another embodiment, the DNA is cDNA. In another embodiment, the DNA is genomic DNA. In another embodiment, the nucleic acid is RNA.

In one embodiment, the mammalian NMU receptor is a human NMU receptor. In a further embodiment, the human NMU receptor is a human SNORF62 receptor, a rat SNORF62a receptor, or a rat SNORF62b receptor. In another embodiment, the human SNORF62 receptor has an amino acid sequence identical to that encoded by the plasmid pEXJ.T3T7-hSNORF62-f (Patent Deposit Designation No. PTA-1042). In another embodiment, the human SNORF62 receptor has an amino acid sequence identical to the amino acid sequence shown in FIGS. 2A–2B (SEQ ID NO: 2). In another embodiment, the rat SNORF62a receptor has an amino acid sequence identical to the amino acid sequence shown in FIGS. 18A–18B (SEQ ID NO: 27). In another embodiment, the rat SNORF62b receptor has an amino acid sequence identical to the amino acid sequence shown in FIGS. 20A–20B (SEQ ID NO: 29).

In a further embodiment, the human NMU receptor is a human SNORF72 receptor or a rat SNORF72 receptor. In another embodiment, the human SNORF72 receptor has an amino acid sequence identical to that encoded by the plasmid pEXJ.T3T7-hSNORF72-f (Patent Deposit Designation No. PTA-1446). In another embodiment, the human SNORF72 receptor has an amino acid sequence identical to the amino acid sequence shown in FIGS. 4A–4B (SEQ ID NO: 4). In another embodiment, the rat SNORF72 receptor has an amino acid sequence identical to that encoded by the plasmid pEXJ.BS-rSNORF72-f (Patent Deposit Designation No. PTA-1927). In another embodiment, the rat SNORF72 receptor has an amino acid sequence identical to the amino acid sequence shown in FIGS. 15A–15B (SEQ ID NO: 25).

This invention provides a purified mammalian SNORF62 or SNORF72 receptor protein. In one embodiment, the SNORF62 receptor protein is a human SNORF62 receptor protein, a rat SNORF62a receptor protein, or a rat SNORF62b receptor protein. In another embodiment, the SNORF72 receptor protein is a human SNORF72 receptor protein or a rat SNORF72 receptor protein.

This invention provides a vector comprising the nucleic acid of this invention. This invention further provides a vector adapted for expression in a cell which comprises the regulatory elements necessary for expression of the nucleic acid in the cell operatively linked to the nucleic acid encoding the receptor so as to permit expression thereof, wherein the cell is a bacterial, amphibian, yeast, insect or mammalian cell. In one embodiment, the vector is a baculovirus. In another embodiment, the vector is a plasmid.

This invention provides a plasmid designated pEXJ.T3T7-hSNORF62-f (Patent Deposit Designation No. PTA-1042). This invention also provides a plasmid designated pEXJ.T3T7-hSNORF72-f (Patent Deposit Designation No. PTA-1446). This invention also provides a plasmid designated pEXJ.BS-rSNORF72-f (Patent Deposit Designation No. PTA-1927).

This invention further provides for any vector or plasmid which comprises modified untranslated sequences, which are beneficial for expression in desired host cells or for use in binding or functional assays. For example, a vector or plasmid with untranslated sequences of varying lengths may express differing amounts of the polypeptide depending upon the host cell used. In an embodiment, the vector or plasmid comprises the coding sequence of the polypeptide and the regulatory elements necessary for expression in the host cell.

This invention provides for a cell comprising the vector of this invention. In one embodiment, the cell is a non-mammalian cell. In one embodiment, the non-mammalian cell is a Xenopus oocyte cell or a Xenopus melanophore cell. In another embodiment, the cell is a mammalian cell. In another embodiment, the cell is a COS-7 cell, a 293 human embryonic kidney cell, a NIH-3T3 cell, a LM(tk−) cell, a mouse Y1 cell, or a CHO cell. In another embodiment, the cell is an insect cell. In another embodiment, the insect cell is an Sf9 cell, an Sf21 cell or a Trichoplusia ni 5B-4 cell.

This invention provides a membrane preparation isolated from the cell in accordance with this invention.

Furthermore, this invention provides for a nucleic acid probe comprising at least 15 nucleotides, which probe specifically hybridizes with a nucleic acid encoding a mammalian SNORF62 or SNORF72 receptor, wherein the probe has a sequence complementary to a unique sequence present within one of the two strands of the nucleic acid encoding the mammalian SNORF62 or SNORF72 receptor contained in plasmid pEXJ.T3T7-hSNORF62-f (Patent Deposit Designation No. PTA-1042), plasmid pEXJ.T3T7-hSNORF72-f (Patent Deposit Designation No. PTA-1446), or plasmid pEXJ.BS-rSNORF72-f (Patent Deposit Designation No. PTA-1927), respectively.

This invention further provides a nucleic acid probe comprising at least 15 nucleotides, which probe specifically hybridizes with a nucleic acid encoding a mammalian SNORF62 receptor, wherein the probe has a sequence complementary to a unique sequence present within (a) the nucleic acid sequence shown in FIGS. 1A–1B (SEQ ID NO: 1), (b) the nucleic acid sequence shown in FIGS. 17A–17B (SEQ ID NO: 26), (c) the nucleic acid sequence shown in FIGS. 19A–19B (SEQ ID NO: 28) or (d) the reverse complement to (a), (b) or (c). This invention further provides a nucleic acid probe comprising at least 15 nucleotides, which probe specifically hybridizes with a nucleic acid encoding a mammalian SNORF72 receptor, wherein the probe has a sequence complementary to a unique sequence present within (a) the nucleic acid sequence shown in FIGS. 3A–3B (SEQ ID NO: 3), (b) the nucleic acid sequence shown in FIGS. 14A–14B or (c) the reverse complement or (a) or (b). In one embodiment, the nucleic acid is DNA. In another embodiment, the nucleic acid is RNA.

As used herein, the phrase "specifically hybridizing" means the ability of a nucleic acid molecule to recognize a nucleic acid sequence complementary to its own and to form double-helical segments through hydrogen bonding between complementary base pairs.

The nucleic acids of this invention may be used as probes to obtain homologous nucleic acids from other species and to detect the existence of nucleic acids having complementary sequences in samples.

The nucleic acids may also be used to express the receptors they encode in transfected cells.

The use of a constitutively active receptor encoded by SNORF62 either occurring naturally without further modification or after appropriate point mutations, deletions or the like, allows screening for antagonists and in vivo use of such antagonists to attribute a role to receptor SNORF62 without prior knowledge of the endogenous ligand.

The use of a constitutively active receptor encoded by SNORF72 either occurring naturally without further modification or after appropriate point mutations, deletions or the like, allows screening for antagonists and in vivo use of such antagonists to attribute a role to receptor SNORF72 without prior knowledge of the endogenous ligand.

Use of the nucleic acids further enables elucidation of possible receptor diversity and of the existence of multiple subtypes within a family of receptors of which SNORF62 is a member.

Use of the nucleic acids further enables elucidation of possible receptor diversity and of the existence of multiple subtypes within a family of receptors of which SNORF72 is a member.

Finally, it is contemplated that the receptors of this invention will serve as a valuable tool for designing drugs for treating various pathophysiological conditions such as chronic and acute inflammation, arthritis, autoimmune diseases, transplant rejection, graft vs. host disease, bacterial, fungal, protozoan and viral infections, septicemia, AIDS, pain, psychotic and neurological disorders, including anxiety, depression, schizophrenia, dementia, mental retardation, memory loss, epilepsy, neuromotor disorders, locomotor disorders, respiratory disorders, asthma, eating/body weight disorders including obesity, bulimia, diabetes, anorexia, nausea, hypertension, hypotension, vascular and cardiovascular disorders, ischemia, stroke, cancers, ulcers, urinary retention, sexual/reproductive disorders, circadian rhythm disorders, renal disorders, bone diseases including osteoporosis, benign prostatic hypertrophy, gastrointestinal disorders, nasal congestion, dermatological disorders such as psoriasis, allergies, Parkinson's disease, Alzheimer's disease, acute heart failure, angina disorders, delirium, dyskinesias such as Huntington's disease or Gille's de la Tourette's syndrome, among others and diagnostic assays for such conditions. The receptors of this invention may also serve as a valuable tool for designing drugs for chemoprevention.

Methods of transfecting cells e.g. mammalian cells, with such nucleic acid to obtain cells in which the receptor is expressed on the surface of the cell are well known in the art. (See, for example, U.S. Pat. Nos. 5,053,337; 5,155,218; 5,360,735; 5,472,866; 5,476,782; 5,516,653; 5,545,549; 5,556,753; 5,595,880; 5,602,024; 5,639,652; 5,652,113; 5,661,024; 5,766,879; 5,786,155; and 5,786,157, the disclosures of which are hereby incorporated by reference in their entireties into this application.)

Such transfected cells may also be used to test compounds and screen compound libraries to obtain compounds which bind to the SNORF62 or SNORF72 receptor, as well as compounds which activate or inhibit activation of functional responses in such cells, and therefore are likely to do so in vivo. (See, for example, U.S. Pat. Nos. 5,053,337; 5,155, 218; 5,360,735; 5,472,866; 5,476,782; 5,516,653; 5,545, 549; 5,556,753; 5,595,880; 5,602,024; 5,639,652; 5,652, 113; 5,661,024; 5,766,879; 5,786,155; and 5,786,157, the disclosures of which are hereby incorporated by reference in their entireties into this application.)

This invention provides an antibody capable of binding to a mammalian SNORF62 receptor encoded by a nucleic acid encoding a mammalian SNORF62 receptor. This invention further provides an antibody capable of binding to a mammalian SNORF72 receptor encoded by a nucleic acid encoding a mammalian SNORF72 receptor. In an embodiment of the present invention, the mammalian SNORF62 receptor is a human SNORF62 receptor, a rat SNORF 62a receptor, or a rat SNORF62b receptor. In a further embodiment, the mammalian SNORF72 receptor is a human SNORF72 receptor or a rat SNORF72 receptor.

This invention also provides an agent capable of competitively inhibiting the binding of the antibody to a mammalian SNORF62 or SNORF72 receptor. In one embodiment, the antibody is a monoclonal antibody or antisera.

Methods of preparing and employing antisense oligonucleotides, antibodies, nucleic acid probes and transgenic animals directed to the SNORF62 and SNORF72 receptors are well known in the art. (See, for example, U.S. Pat. Nos. 5,053,337; 5,155,218; 5,360,735; 5,472,866; 5,476,782; 5,516,653; 5,545,549; 5,556,753; 5,595,880; 5,602,024; 5,639,652; 5,652,113; 5,661,024; 5,766,879; 5,786,155; and 5,786,157, the disclosures of which are hereby incorporated by reference in their entireties into this application.)

This invention provides for an antisense oligonucleotide having a sequence capable of specifically hybridizing to RNA encoding a mammalian SNORF62 or SNORF72 receptor, so as to prevent translation of such RNA. This invention further provides for an antisense oligonucleotide having a sequence capable of specifically hybridizing to genomic DNA encoding a mammalian SNORF62 or SNORF72 receptor, so as to prevent transcription of such genomic DNA. In one embodiment, the oligonucleotide comprises chemically modified nucleotides or nucleotide analogues.

This invention still further provides a pharmaceutical composition comprising (a) an amount of an oligonucleotide in accordance with this invention capable of passing through a cell membrane and effective to reduce expression of a mammalian SNORF62 or SNORF72 receptor and (b) a pharmaceutically acceptable carrier capable of passing through the cell membrane.

In one embodiment, the oligonucleotide is coupled to a substance which inactivates mRNA. In another embodiment, the substance which inactivates mRNA is a ribozyme. In another embodiment, the pharmaceutically acceptable carrier comprises a structure which binds to a mammalian SNORF62 or SNORF72 receptor on a cell capable of being taken up by the cells after binding to the structure. In another embodiment, the pharmaceutically acceptable carrier is capable of binding to a mammalian SNORF62 or SNORF72 receptor which is specific for a selected cell type.

This invention also provides a pharmaceutical composition which comprises an amount of an antibody in accordance with this invention effective to block binding of a ligand to a human SNORF62 receptor or a human SNORF72 receptor and a pharmaceutically acceptable carrier.

This invention further provides a transgenic, nonhuman mammal expressing DNA encoding a mammalian SNORF62 or SNORF72 receptor in accordance with this invention. This invention provides a transgenic, nonhuman mammal comprising a homologous recombination knockout of a native mammalian SNORF62 or SNORF72 receptor. This invention further provides a transgenic, nonhuman mammal whose genome comprises antisense DNA complementary to DNA encoding a mammalian SNORF62 or SNORF72 receptor in accordance with this invention so placed within such genome as to be transcribed into antisense mRNA which is complementary and hybridizes with mRNA encoding the mammalian SNORF62 or SNORF72 receptor so as to thereby reduce translation or such mRNA and expression of such receptor. In one embodiment, the DNA encoding the mammalian SNORF62 or SNORF72 receptor additionally comprises an inducible promoter. In another embodiment, the DNA encoding the mammalian SNORF62 or SNORF72 receptor additionally comprises tissue specific regulatory elements. In another embodiment, the transgenic, nonhuman mammal is a mouse.

This invention provides for a process for identifying a chemical compound which specifically binds to a mammalian SNORF62 receptor which comprises contacting cells containing DNA encoding, and expressing on their cell surface, the mammalian SNORF62 receptor, wherein such cells do not normally express the mammalian SNORF62 receptor, with the compound under conditions suitable for binding, and detecting specific binding of the chemical compound to the mammalian SNORF62 receptor.

This invention provides for a process for identifying a chemical compound which specifically binds to a mammalian SNORF72 receptor which comprises contacting cells containing DNA encoding, and expressing on their cell surface, the mammalian SNORF72 receptor, wherein such cells do not normally express the mammalian SNORF72 receptor, with the compound under conditions suitable for binding, and detecting specific binding of the chemical compound to the mammalian SNORF72 receptor.

This invention further provides for a process for identifying a chemical compound which specifically binds to a mammalian SNORF62 receptor which comprises contacting a membrane preparation from cells containing DNA encoding and expressing on their cell surface the mammalian SNORF62 receptor, wherein such cells do not normally express the mammalian SNORF62 receptor, with the compound under conditions suitable for binding, and detecting specific binding of the chemical compound to the mammalian SNORF62 receptor.

This invention further provides for a process for identifying a chemical compound which specifically binds to a mammalian SNORF72 receptor which comprises contacting a membrane preparation from cells containing DNA encoding and expressing on their cell surface the mammalian SNORF72 receptor, wherein such cells do not normally express the mammalian SNORF72 receptor, with the compound under conditions suitable for binding, and detecting specific binding of the chemical compound to the mammalian SNORF72 receptor.

In an embodiment, the mammalian SNORF62 receptor is a human SNORF62 receptor, a rat SNORF62a receptor, or a rat SNORF62b receptor. In another embodiment, the mammalian SNORF62 receptor has substantially the same amino acid sequence as the human SNORF62 receptor encoded by plasmid pEXJ.T3T7-hSNORF62-f (Patent Deposit Designation No. PTA-1042).

In a further embodiment, the mammalian SNORF72 receptor is a human SNORF72 receptor or a rat SNORF72 receptor. In another embodiment, the mammalian SNORF72 receptor has substantially the same amino acid sequence as the human SNORF72 receptor encoded by plasmid pEXJ.T3T7-hSNORF72-f (Patent Deposit Designation No. PTA-1446). In yet another embodiment, the mammalian SNORF72 receptor has substantially the same amino acid sequence as the rat SNORF72 receptor encoded by plasmid pEXJ.BS-rSNORF72-f (Patent Deposit Designation No. PTA-1927).

Figure 2A:
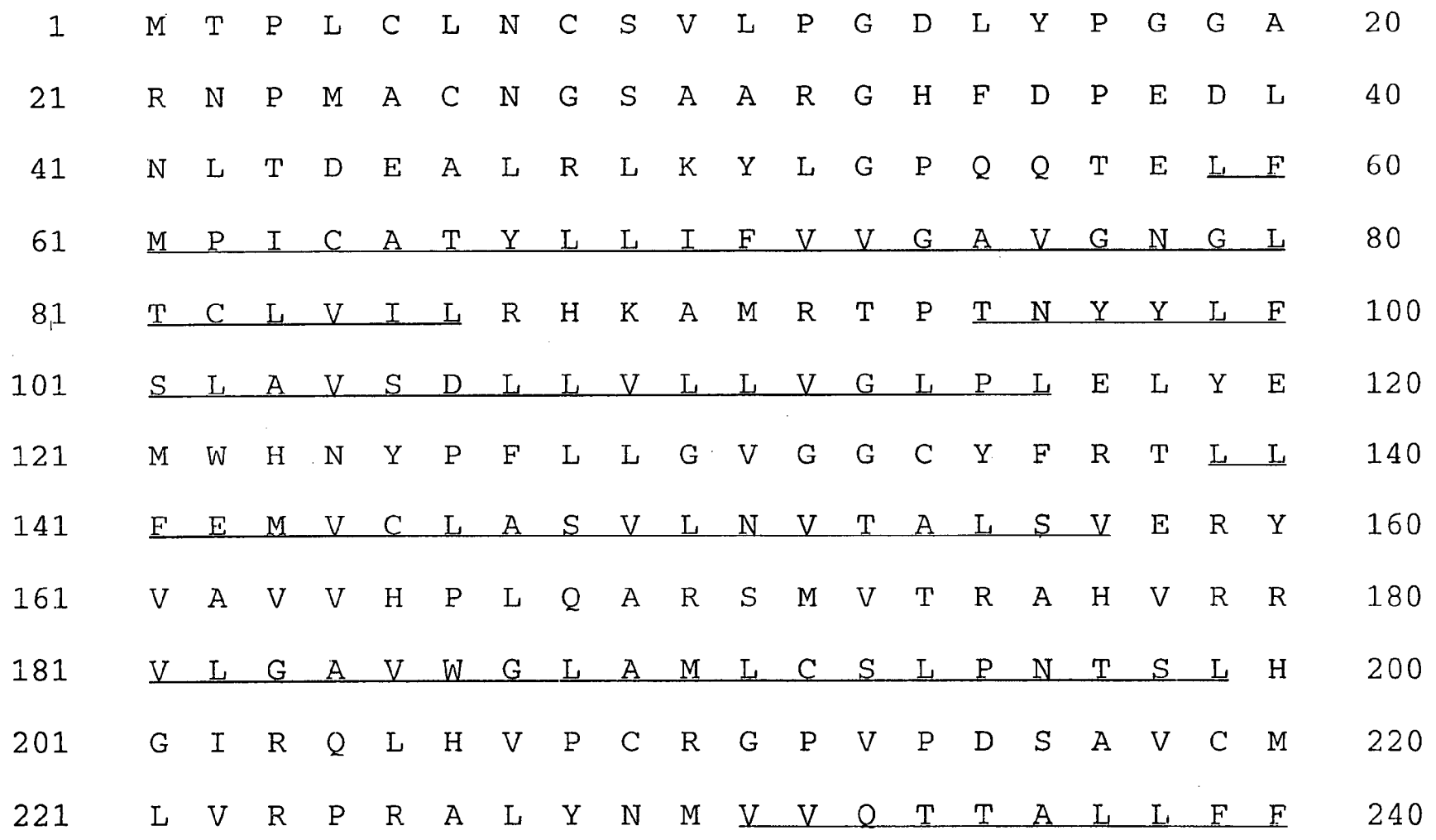
Figure 2B:
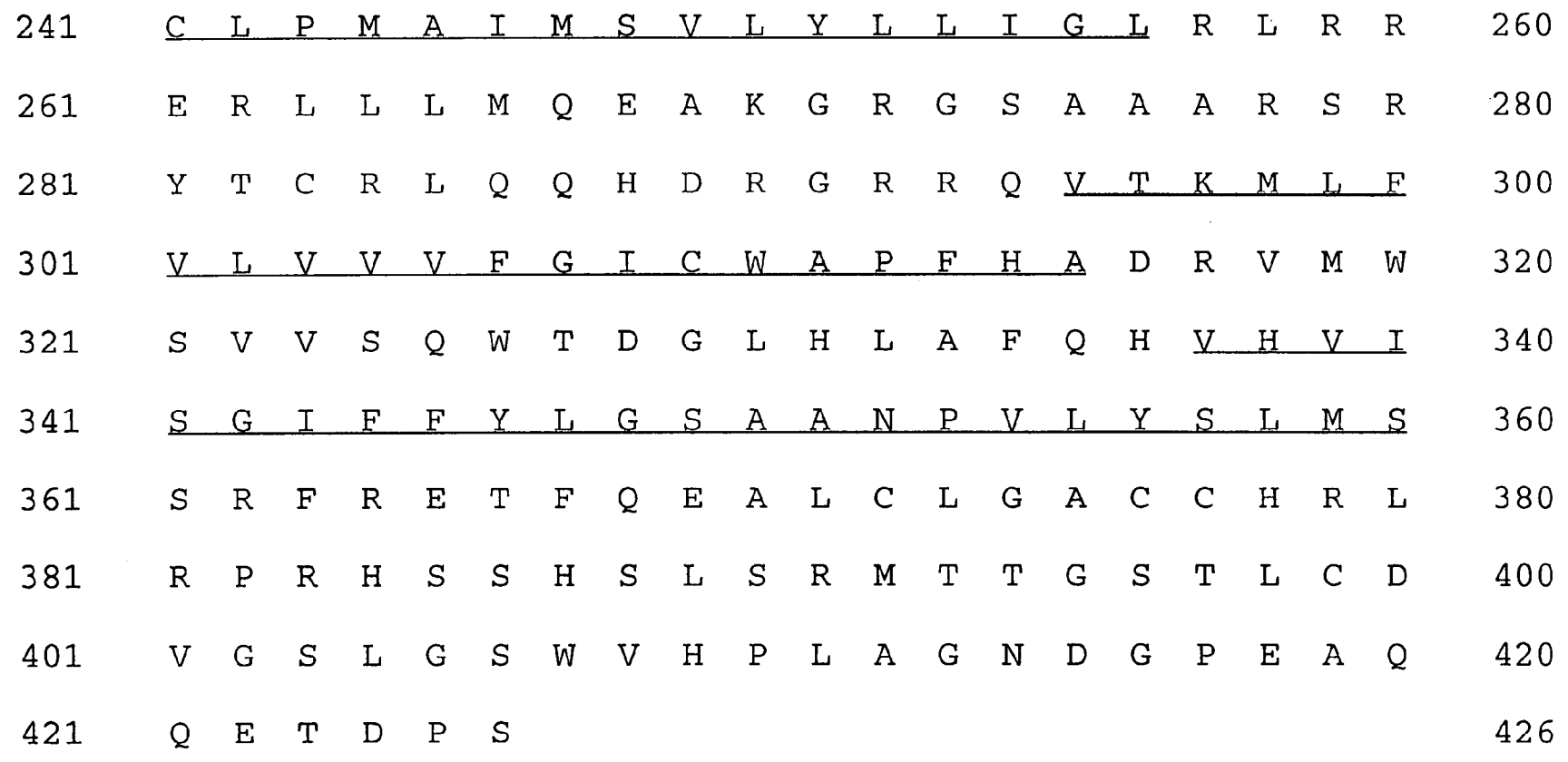
Figure 4A:
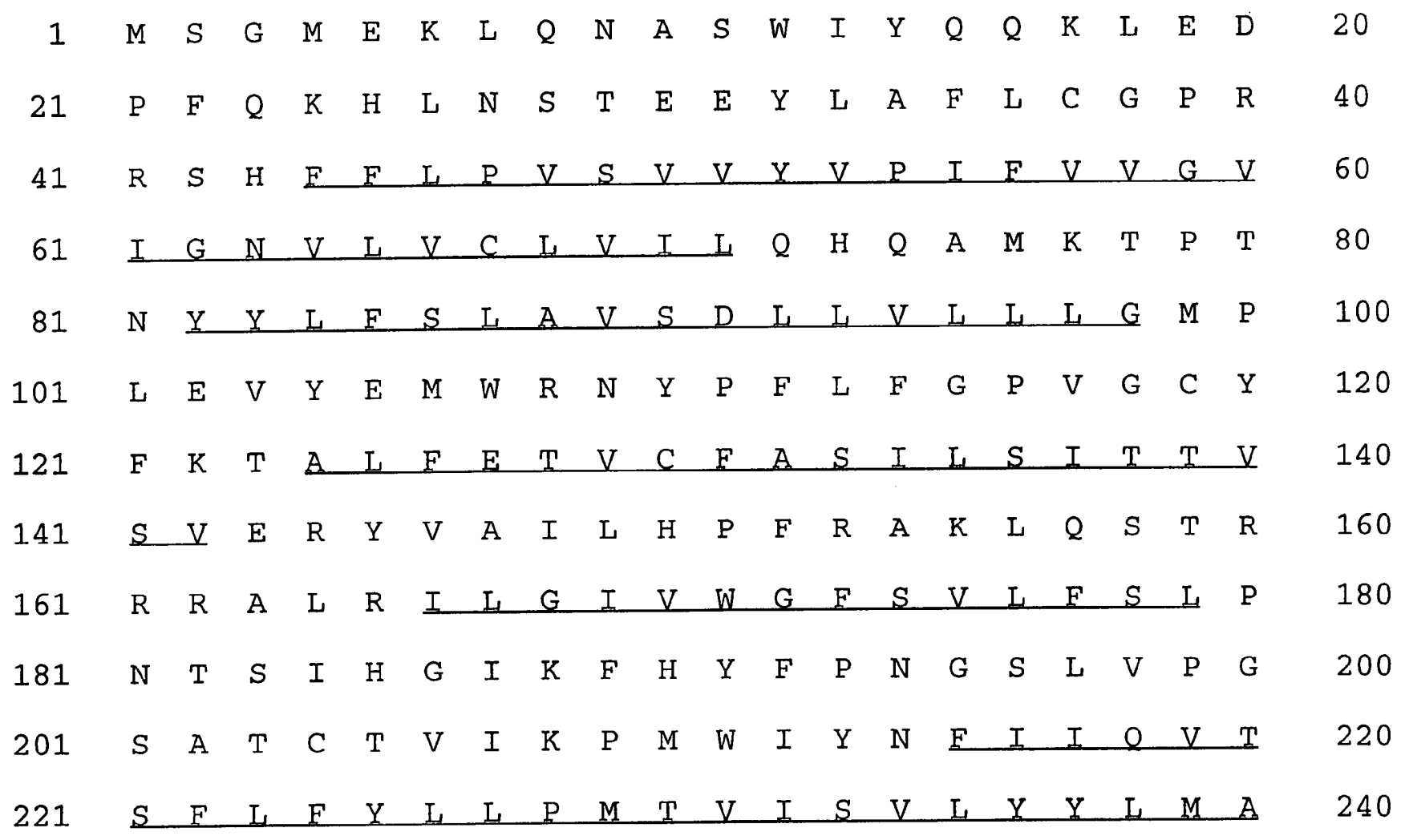
Figure 4B:
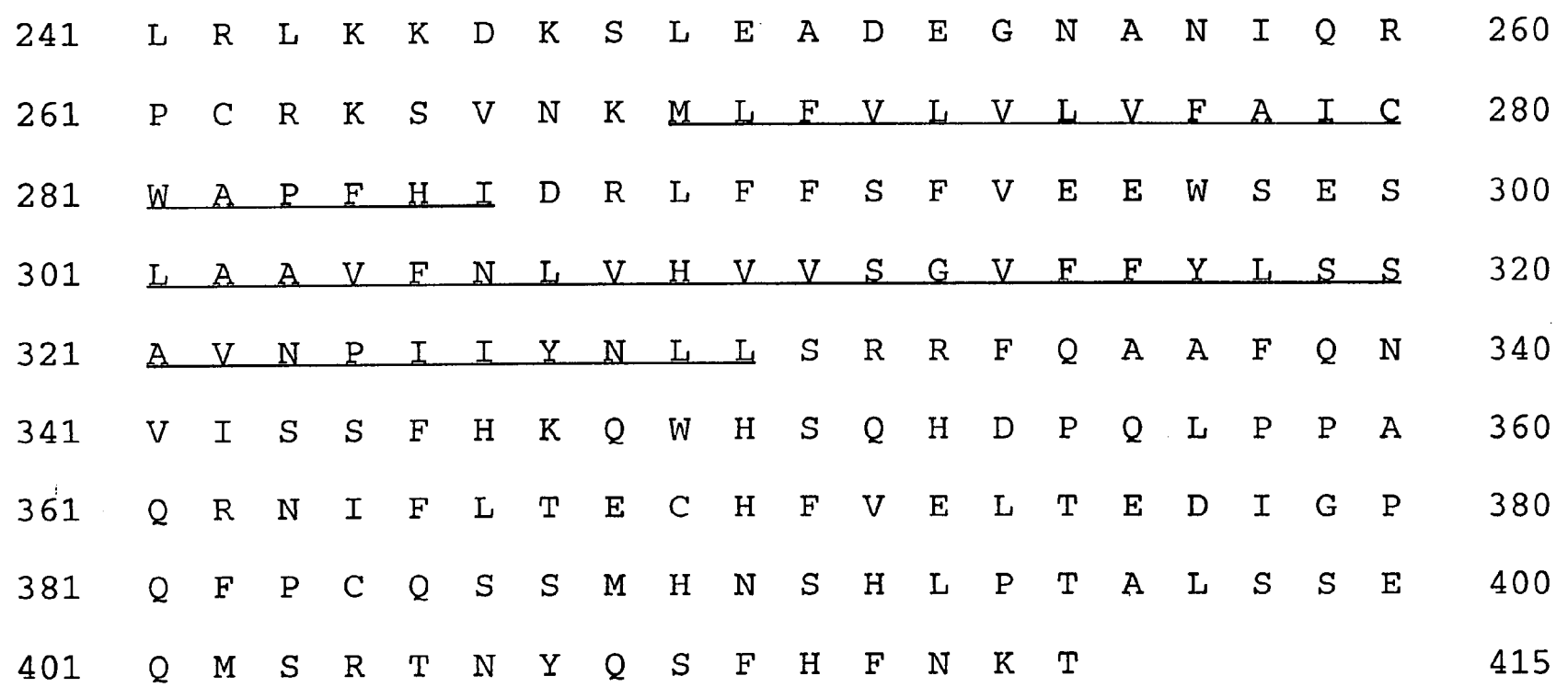
Figure 15A:
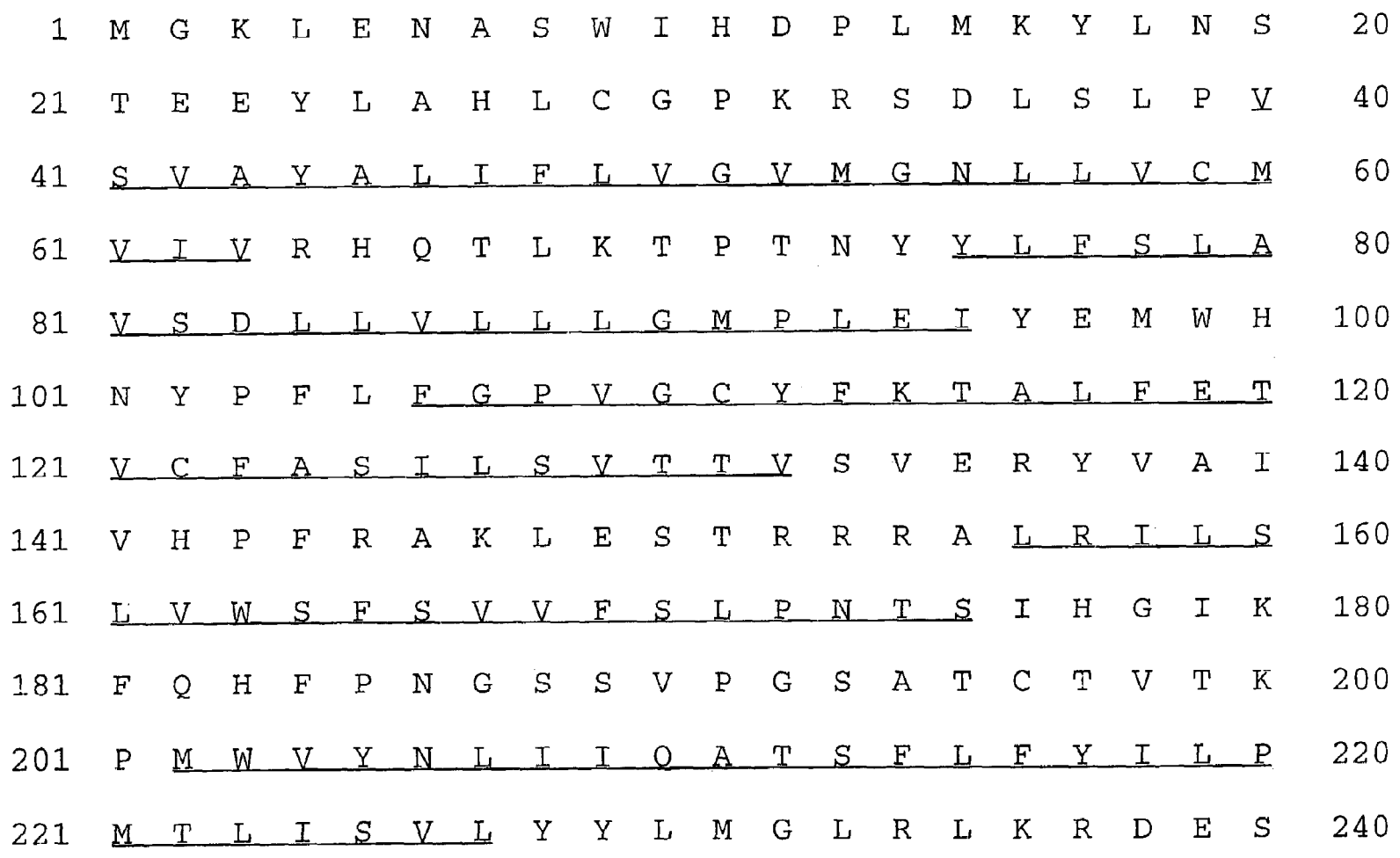
Figure 15B:
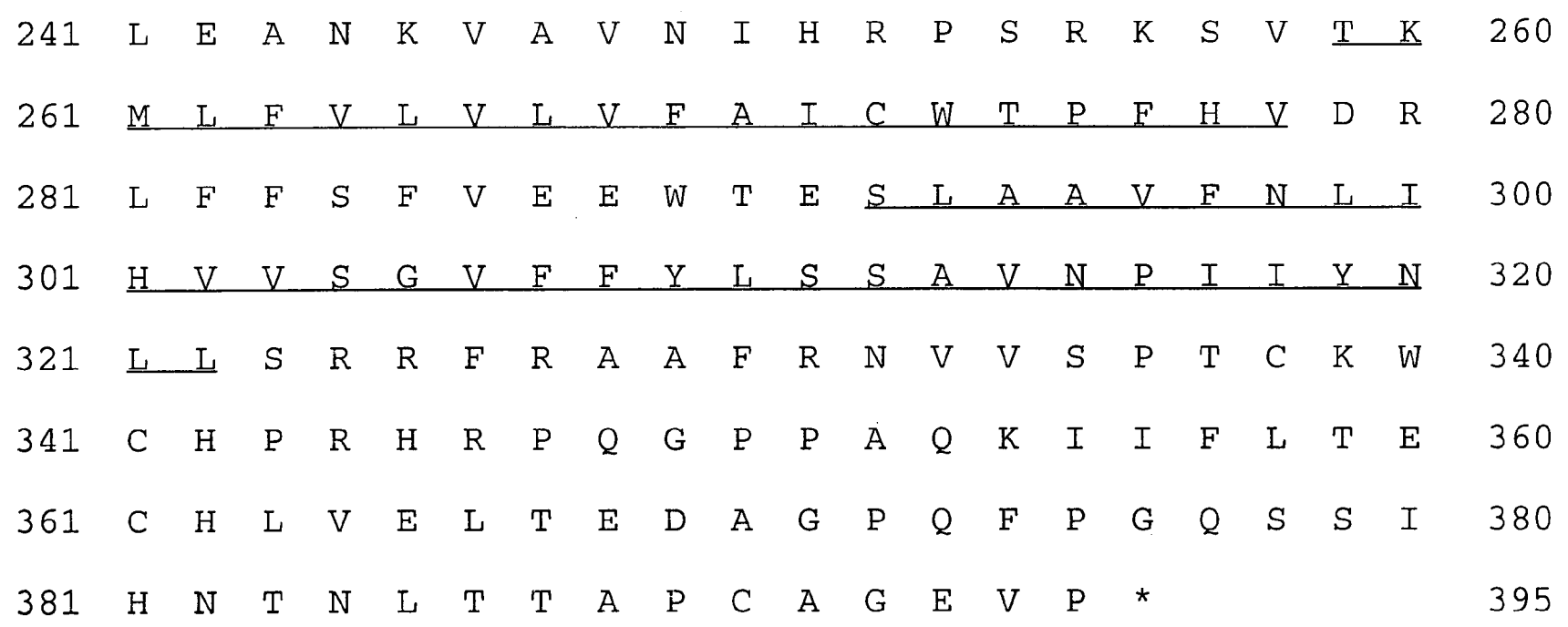

In another embodiment, the mammalian SNORF62 or SNORF72 receptor has substantially the same amino acid sequence as that shown in FIGS. 2A–2B (SEQ ID NO: 2), FIGS. 4A–4B (SEQ ID NO: 4), FIGS. 15A–15B (SEQ ID NO: 25), FIGS. 18A–18B (SEQ ID NO: 27), or FIGS. 20A–20B (SEQ ID NO: 29), respectively. In another embodiment, the mammalian SNORF62 or SNORF72 receptor has the amino acid sequence shown in FIGS. 2A–2B (SEQ ID NO: 2), FIGS. 4A–4B (SEQ ID NO: 4), FIGS. 15A–15B (SEQ ID NO: 25), FIGS. 18A–18B (SEQ ID NO: 27), or FIGS. 20A–20B (SEQ ID NO: 29), respectively.

In one embodiment, the compound is not previously known to bind to a mammalian SNORF62 or SNORF72 receptor. In one embodiment, the cell is an insect cell. In one embodiment, the cell is a mammalian cell. In another embodiment, the cell is normeuronal in origin. In another embodiment, the normeuronal cell is a COS-7 cell, 293 human embryonic kidney cell, a CHO cell, a NIH-3T3 cell, a mouse Y1 cell, or a LM(tk–) cell. In another embodiment, the compound is a compound not previously known to bind to a mammalian SNORF62 or SNORF72 receptor. This invention provides a compound identified by the preceding processes according to this invention.

This invention still further provides a process involving competitive binding for identifying a chemical compound which specifically binds to a mammalian NMU receptor which comprises separately contacting cells expressing on their cell surface the mammalian NMU receptor, wherein such cells do not normally express the mammalian NMU receptor, with both the chemical compound and a second chemical compound known to bind to the receptor, and with only the second chemical compound, under conditions suitable for binding of such compounds to the receptor, and detecting specific binding of the chemical compound to the mammalian NMU receptor, a decrease in the binding of the second chemical compound to the mammalian NMU receptor in the presence of the chemical compound being tested indicating that such chemical compound binds to the mammalian NMU receptor.

This invention provides a process involving competitive binding for identifying a chemical compound which specifically binds to a mammalian NMU receptor which comprises separately contacting a membrane preparation from cells expressing on their cell surface the mammalian NMU receptor, wherein such cells do not normally express the mammalian NMU receptor, with both the chemical compound and a second chemical compound known to bind to the receptor, and with only the second chemical compound, under conditions suitable for binding of such compounds to the receptor, and detecting specific binding of the chemical compound to the mammalian NMU receptor, a decrease in the binding of the second chemical compound to the mammalian NMU receptor in the presence of the chemical compound being tested indicating that such chemical compound binds to the mammalian NMU receptor.

In an embodiment of the present invention, the second chemical compound is an NMU peptide. Examples of NMU peptides include, but are not limited to, human NMU-25, human NMU-8, porcine NMU-8, porcine NMU-25, rat NMU-25 and any peptide comprising the carboxyl terminal seven amino acid residues of human NMU-8.

In one embodiment, the mammalian NMU receptor is a human SNORF62 receptor, a rat SNORF62a receptor or a rat SNORF62b receptor. In another embodiment, the mammalian NMU receptor is a human SNORF72 receptor or a rat SNORF72 receptor. In a further embodiment, the cell is an insect cell. In another embodiment, the cell is a mammalian cell. In another embodiment, the cell is normeuronal in origin. In another embodiment, the normeuronal cell is a COS-7 cell, 293 human embryonic kidney cell, a CHO cell, a NIH-3T3 cell, a mouse Y1 cell, or a LM(tk–) cell. In another embodiment, the compound is not previously known to bind to a mammalian NMU receptor. This invention provides for a compound identified by the preceding process according to this invention.

This invention provides for a method of screening a plurality of chemical compounds not known to bind to a mammalian NMU receptor to identify a compound which specifically binds to the mammalian NMU receptor, which comprises (a) contacting cells transfected with, and expressing, DNA encoding the mammalian NMU receptor with a compound known to bind specifically to the mammalian NMU receptor; (b) contacting the cells of step (a) with the plurality of compounds not known to bind specifically to the mammalian NMU receptor, under conditions permitting binding of compounds known to bind to the mammalian NMU receptor; (c) determining whether the binding of the compound known to bind to the mammalian NMU receptor is reduced in the presence of the plurality of compounds, relative to the binding of the compound in the absence of the plurality of compounds; and if so (d) separately determining the binding to the mammalian NMU receptor of each compound included in the plurality of compounds, so as to thereby identify any compound included therein which specifically binds to the mammalian NMU receptor.

This invention provides a method of screening a plurality of chemical compounds not known to bind to a mammalian NMU receptor to identify a compound which specifically binds to the mammalian NMU receptor, which comprises (a) contacting a membrane preparation from cells transfected with, and expressing, DNA encoding the mammalian NMU receptor with the plurality of compounds not known to bind specifically to the mammalian NMU receptor under conditions permitting binding of compounds known to bind to the mammalian NMU receptor; (b) determining whether the binding of a compound known to bind to the mammalian NMU receptor is reduced in the presence of the plurality of compounds, relative to the binding of the compound in the absence of the plurality of compounds; and if so (c) separately determining the binding to the mammalian NMU receptor of each compound included in the plurality of compounds, so as to thereby identify any compound included therein which specifically binds to the mammalian NMU receptor.

In one embodiment, the mammalian NMU receptor is a human SNORF62 receptor, a rat SNORF62a receptor or a rat SNORF62b receptor. In a further embodiment, the mammalian NMU receptor is a human SNORF72 receptor or a rat SNORF72 receptor. In another embodiment, the cell is a mammalian cell. In another embodiment, the mammalian cell is non-neuronal in origin. In a further embodiment, the non-neuronal cell is a COS-7 cell, a 293 human embryonic kidney cell, a LM(tk–) cell, a CHO cell, a mouse Y1 cell, or an NIH-3T3 cell.

This invention also provides a method of detecting expression of a mammalian SNORF62 or SNORF72 receptor by detecting the presence of mRNA coding for the mammalian SNORF62 or SNORF72 receptor which comprises obtaining total mRNA from the cell and contacting the mRNA so obtained with a nucleic acid probe according to this invention under hybridizing conditions, detecting the presence of mRNA hybridized to the probe, and thereby detecting the expression of the mammalian SNORF62 or SNORF72 receptor by the cell.

This invention further provides for a method of detecting the presence of a mammalian SNORF62 or SNORF72 receptor on the surface of a cell which comprises contacting the cell with an antibody according to this invention under conditions permitting binding of the antibody to the receptor, detecting the presence of the antibody bound to the cell, and thereby detecting the presence of the mammalian SNORF62 or SNORF72 receptor on the surface of the cell.

This invention still further provides a method of determining the physiological effects of varying levels of activity of a mammalian SNORF62 or SNORF72 receptor which comprises producing a transgenic, nonhuman mammal in accordance with this invention whose levels of mammalian SNORF62 or SNORF72 receptor activity are varied by use of an inducible promoter which regulates mammalian SNORF62 or SNORF72 receptor expression.

This invention additionally provides a method of determining the physiological effects of varying levels of activity of a mammalian SNORF62 or SNORF72 receptor which comprises producing a panel of transgenic, nonhuman mammals in accordance with this invention each expressing a different amount of a mammalian SNORF62 or SNORF72 receptor.

Moreover, this invention provides method for identifying an antagonist capable of alleviating an abnormality wherein the abnormality is alleviated by decreasing the activity of a mammalian SNORF62 or SNORF72 receptor comprising administering a compound to a transgenic, nonhuman mammal according to this invention, and determining whether the compound alleviates any physiological and/or behavioral abnormality displayed by the transgenic, nonhuman mammal as a result of overactivity of a mammalian SNORF62 or SNORF72 receptor, the alleviation of such an abnormality identifying the compound as an antagonist. In an embodiment, the mammalian SNORF62 receptor is a human SNORF62 receptor, a rat SNORF62a receptor or a rat SNORF62b receptor. In another embodiment, the mammalian SNORF72 receptor is a human SNORF72 receptor or a rat SNORF72 receptor.

The invention also provides an antagonist identified by the preceding method according to this invention. This invention further provides a composition, e.g. a pharmaceutical composition comprising an antagonist according to this invention and a carrier, e.g. a pharmaceutically acceptable carrier.

This invention provides a method of treating an abnormality in a subject wherein the abnormality is alleviated by decreasing the activity of a mammalian SNORF62 receptor which comprises administering to the subject an effective amount of the pharmaceutical composition according to this invention so as to thereby treat the abnormality.

This invention provides a method of treating an abnormality in a subject wherein the abnormality is alleviated by decreasing the activity of a mammalian SNORF72 receptor which comprises administering to the subject an effective amount of the pharmaceutical composition according to this invention so as to thereby treat the abnormality.

In addition, this invention provides a method for identifying an agonist capable of alleviating an abnormality in a subject wherein the abnormality is alleviated by increasing the activity of a mammalian SNORF62 or SNORF72 receptor comprising administering a compound to a transgenic, nonhuman mammal according to this invention, and determining whether the compound alleviates any physiological and/or behavioral abnormality displayed by the transgenic, nonhuman mammal, the alleviation of such an abnormality identifying the compound as an agonist. In an embodiment, the mammalian SNORF62 receptor is a human SNORF62 receptor, a rat SNORF62a receptor or a rat SNORF62b receptor. In a further embodiment, the mammalian SNORF72 receptor is a human SNORF72 receptor or a rat SNORF72 receptor. This invention provides an agonist identified by the preceding method according to this invention. This invention provides a composition, e.g. a pharmaceutical composition comprising an agonist identified by a method according to this invention and a carrier, e.g. a pharmaceutically acceptable carrier.

Moreover, this invention provides a method of treating an abnormality in a subject wherein the abnormality is alleviated by increasing the activity of a mammalian SNORF62 or SNORF72 receptor which comprises administering to the subject an effective amount of the pharmaceutical composition of this invention so as to thereby treat the abnormality.

Yet further, this invention provides a method for diagnosing a predisposition to a disorder associated with the activity of a specific mammalian allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a mammalian SNORF62 or SNORF72 receptor and labeled with a detectable marker; (e) detecting labeled bands which have hybridized to the DNA encoding a mammalian SNORF62 or SNORF72 receptor to create a unique-band pattern specific to the DNA of subjects suffering from the disorder; (f) repeating steps (a)–(e) with DNA obtained for diagnosis from subjects not yet suffering from the disorder; and (g) comparing the unique band pattern specific to the DNA of subjects suffering from the disorder from step (e) with the band pattern from step (f) for subjects not yet suffering from the disorder so as to determine whether the patterns are the same or different and thereby diagnose predisposition to the disorder if the patterns are the same.

In one embodiment, the disorder is a disorder associated with the activity of a specific mammalian allele is diagnosed.

This invention also provides a method of preparing a purified mammalian SNORF62 receptor according to this invention which comprises: (a) culturing cells which express the mammalian SNORF62 receptor; (b) recovering the mammalian SNORF62 receptor from the cells; and (c) purifying the mammalian SNORF62 receptor so recovered.

This invention also provides a method of preparing a purified mammalian SNORF72 receptor according to this invention which comprises: (a) culturing cells which express the mammalian SNORF72 receptor; (b) recovering the mammalian SNORF72 receptor from the cells; and (c) purifying the mammalian SNORF72 receptor so recovered.

This invention further provides a method of preparing a purified mammalian SNORF62 receptor according to this invention which comprises: (a) inserting a nucleic acid encoding the mammalian SNORF62 receptor into a suitable expression vector; (b) introducing the resulting vector into a suitable host cell; (c) placing the resulting host cell in suitable condition permitting the production of the mammalian SNORF62 receptor; (d) recovering the mammalian SNORF62 receptor so produced; and optionally (e) isolating and/or purifying the mammalian SNORF62 receptor so recovered.

This invention further provides a method of preparing a purified mammalian SNORF72 receptor according to this invention which comprises: (a) inserting a nucleic acid encoding the mammalian SNORF72 receptor into a suitable expression vector; (b) introducing the resulting vector into a suitable host cell; (c) placing the resulting host cell in suitable condition permitting the production of the mammalian SNORF72 receptor; (d) recovering the mammalian SNORF72 receptor so produced; and optionally (e) isolating and/or purifying the mammalian SNORF72 receptor so recovered.

Furthermore, this invention provides a process for determining whether a chemical compound is a mammalian SNORF62 receptor agonist which comprises contacting cells transfected with and expressing DNA encoding the mammalian SNORF62 receptor with the compound under conditions permitting the activation of the mammalian SNORF62 receptor, and detecting any increase in mammalian SNORF62 receptor activity, so as to thereby determine whether the compound is a mammalian SNORF62 receptor agonist.

Furthermore, this invention provides a process for determining whether a chemical compound is a mammalian NMU receptor agonist which comprises contacting cells transfected with and expressing DNA encoding the mammalian NMU receptor with the compound under conditions permitting the activation of the mammalian NMU receptor, and detecting any increase in mammalian NMU receptor activity, so as to thereby determine whether the compound is a mammalian NMU receptor agonist.

Furthermore, this invention provides a process for determining whether a chemical compound is a mammalian SNORF72 receptor agonist which comprises contacting cells transfected with and expressing DNA encoding the mammalian SNORF72 receptor with the compound under conditions permitting the activation of the mammalian SNORF72 receptor, and detecting any increase in mammalian SNORF72 receptor activity, so as to thereby determine whether the compound is a mammalian SNORF72 receptor agonist.

This invention also provides a process for determining whether a chemical compound is a mammalian NMU receptor antagonist which comprises contacting cells transfected with and expressing DNA encoding the mammalian NMU receptor with the compound in the presence of a known mammalian NMU receptor agonist, under conditions permitting the activation of the mammalian NMU receptor, and detecting any decrease in mammalian NMU receptor activity, so as to thereby determine whether the compound is a mammalian NMU receptor antagonist.

This invention also provides a process for determining whether a chemical compound is a mammalian SNORF62 receptor antagonist which comprises contacting cells transfected with and expressing DNA encoding the mammalian SNORF62 receptor with the compound in the presence of a known mammalian SNORF62 receptor agonist, under conditions permitting the activation of the mammalian SNORF62 receptor, and detecting any decrease in mammalian SNORF62 receptor activity, so as to thereby determine whether the compound is a mammalian SNORF62 receptor antagonist.

This invention also provides a process for determining whether a chemical compound is a mammalian SNORF72 receptor antagonist which comprises contacting cells transfected with and expressing DNA encoding the mammalian SNORF72 receptor with the compound in the presence of a known mammalian SNORF72 receptor agonist, under conditions permitting the activation of the mammalian SNORF72 receptor, and detecting any decrease in mammalian SNORF72 receptor activity, so as to thereby determine whether the compound is a mammalian SNORF72 receptor antagonist.

In an embodiment, the mammalian NMU receptor is a human SNORF62 receptor, a rat SNORF62a receptor or a rat SNORF62b receptor. In another embodiment, the mammalian NMU receptor is a human SNORF72 receptor or a rat SNORF72 receptor. In yet another embodiment, the mammalian SNORF62 receptor is a human SNORF62 receptor and the mammalian SNORF72 receptor is a human SNORF72 receptor.

This invention still further provides a composition, for example a pharmaceutical composition, which comprises an amount of a mammalian SNORF62 or SNORF72 receptor agonist determined by a process according to this invention effective to increase activity of a mammalian SNORF62 or SNORF72 receptor and a carrier, for example, a pharmaceutically acceptable carrier. In one embodiment, the mammalian SNORF62 or SNORF72 receptor agonist is not previously known.

Also, this invention provides a composition, for example a pharmaceutical composition, which comprises an amount of a mammalian NMU receptor antagonist determined by a process according to this invention effective to reduce activity of a mammalian NMU receptor and a carrier, for example, a pharmaceutically acceptable carrier. Also, this invention provides a composition, for example a pharmaceutical composition, which comprises an amount of a mammalian SNORF62 receptor antagonist determined by a process according to this invention effective to reduce activity of a mammalian SNORF62 receptor and a carrier, for example, a pharmaceutically acceptable carrier. Also, this invention provides a composition, for example a pharmaceutical composition, which comprises an amount of a mammalian SNORF72 receptor antagonist determined by a process according to this invention effective to reduce activity of a mammalian SNORF72 receptor and a carrier, for example, a pharmaceutically acceptable carrier.

In one embodiment, the mammalian NMU receptor antagonist is not previously known. In an embodiment, the mammalian NMU receptor antagonist is a mammalian SNORF62 receptor antagonist. In a further embodiment, the mammalian NMU receptor antagonist is a mammalian SNORF72 receptor antagonist.

This invention moreover provides a process for determining whether a chemical compound specifically binds to and activates a mammalian SNORF62 receptor, which comprises contacting cells producing a second messenger response and expressing on their cell surface the mammalian SNORF62 receptor, wherein such cells do not normally express the mammalian SNORF62 receptor, with the chemical compound under conditions suitable for activation of the mammalian SNORF62 receptor, and measuring the second messenger response in the presence and in the absence of the chemical compound, a change, e.g. an increase, in the second messenger response in the presence of the chemical compound indicating that the compound activates the mammalian SNORF62 receptor.

This invention moreover provides a process for determining whether a chemical compound specifically binds to and activates a mammalian SNORF72 receptor, which comprises contacting cells producing a second messenger response and expressing on their cell surface the mammalian SNORF72 receptor, wherein such cells do not normally express the mammalian SNORF72 receptor, with the chemical compound under conditions suitable for activation of the mammalian SNORF72 receptor, and measuring the second messenger response in the presence and in the absence of the chemical compound, a change, e.g. an increase, in the second messenger response in the presence of the chemical compound indicating that the compound activates the mammalian SNORF72 receptor.

In one embodiment, the second messenger response comprises chloride channel activation and the change in second messenger is an increase in the level of chloride current. In another embodiment, the second messenger response comprises change in intracellular calcium levels and the change in second messenger is an increase in the measure of intracellular calcium. In another embodiment, the second messenger response comprises release of inositol phosphate and the change in second messenger is an increase in the level of inositol phosphate. In another embodiment, the second messenger response comprises release of arachidonic acid and the change in second messenger is an increase in the level of arachidonic acid. In yet another embodiment, the second messenger response comprises GTPγS ligand binding and the change in second messenger is an increase in GTPγS ligand binding. In another embodiment, the second messenger response comprises activation of MAP kinase and the change in second messenger response is an increase in MAP kinase activation. In a further embodiment, the second messenger response comprises cAMP accumulation and the change in second messenger response is a reduction in cAMP accumulation.

This invention still further provides a process for determining whether a chemical compound specifically binds to and inhibits activation of a mammalian NMU receptor, which comprises separately contacting cells producing a second messenger response and expressing on their cell surface the mammalian NMU receptor, wherein such cells do not normally express the mammalian NMU receptor, with both the chemical compound and a second chemical compound known to activate the mammalian NMU receptor, and with only the second chemical compound, under conditions suitable for activation of the mammalian NMU receptor, and measuring the second messenger response in the presence of only the second chemical compound and in the presence of both the second chemical compound and the chemical compound, a smaller change, e.g. increase, in the second messenger response in the presence of both the chemical compound and the second chemical compound than in the presence of only the second chemical compound indicating that the chemical compound inhibits activation of the mammalian NMU receptor.

In an embodiment of the present invention, the second chemical compound is an NMU peptide. Examples of NMU peptides include, but are not limited to, human NMU-25, human NMU-8, porcine NMU-8, porcine NMU-25, rat NMU-25 and any peptide comprising the carboxyl terminal seven amino acid residues of human NMU-8.

In one embodiment, the second messenger response comprises chloride channel activation and the change in second messenger response is a smaller increase in the level of chloride current in the presence of both the chemical compound and the second chemical compound than in the presence of only the second chemical compound. In another embodiment, the second messenger response comprises change in intracellular calcium levels and the change in second messenger response is a smaller increase in the measure of intracellular calcium in the presence of both the chemical compound and the second chemical compound than in the presence of only the second chemical compound. In another embodiment, the second messenger response comprises release of inositol phosphate and the change in second messenger response is a smaller increase in the level of inositol phosphate in the presence of both the chemical compound and the second chemical compound than in the presence of only the second chemical compound.

In one embodiment, the second messenger response comprises activation of MAP kinase and the change in second messenger response is a smaller increase in the level of MAP kinase activation in the presence of both the chemical compound and the second chemical compound than in the presence of only the second chemical compound. In another embodiment, the second messenger response comprises change in cAMP levels and the change in second messenger response is a smaller change in the level of cAMP in the presence of both the chemical compound and the second chemical compound than in the presence of only the second chemical compound. In another embodiment, the second messenger response comprises release of arachidonic acid and the change in second messenger response is an increase in the level of arachidonic acid levels in the presence of both the chemical compound and the second chemical compound than in the presence of only the second chemical compound. In a further embodiment, the second messenger response comprises GTPγS ligand binding and the change in second messenger is a smaller increase in GTPγS ligand binding in the presence of both the chemical compound and the second chemical compound than in the presence of only the second chemical compound.

In one embodiment, the mammalian NMU receptor is a human SNORF62 receptor, a rat SNORF62a receptor or a rat SNORF62b receptor. In a further embodiment, the mammalian NMU receptor is a human SNORF72 receptor or a rat SNORF72 receptor. In another embodiment, the cell is an insect cell. In another embodiment, the cell is a mammalian cell.

In another embodiment, the mammalian cell is normeuronal in origin. In another embodiment, the normeuronal cell is a COS-7 cell, CHO cell, 293 human embryonic kidney cell, NIH-3T3 cell or LM(tk−) cell. In another embodiment, the compound is not previously known to bind to a mammalian NMU receptor.

Further, this invention provides a compound determined by a process according to this invention and a composition, for example, a pharmaceutical composition, which comprises an amount of a mammalian SNORF62, a mammalian SNORF72 or a mammalian NMU receptor agonist determined to be such by a process according to this invention effective to increase activity of a mammalian SNORF62, a mammalian SNORF72 or a mammalian NMU receptor and a carrier, for example, a pharmaceutically acceptable carrier. In one embodiment, the mammalian SNORF62, mammalian SNORF72 or mammalian NMU receptor agonist is not previously known.

This invention also provides a composition, for example, a pharmaceutical composition, which comprises an amount of a mammalian SNORF62, a mammalian SNORF72 or a mammalian NMU receptor antagonist determined to be such by a process according to this invention, effective to reduce activity of the mammalian SNORF62, the mammalian SNORF72 or the mammalian NMU receptor and a carrier, for example a pharmaceutically acceptable carrier. In one embodiment, the mammalian SNORF62, mammalian SNORF72 or mammalian NMU receptor antagonist is not previously known.

This invention yet further provides a method of screening a plurality of chemical compounds not known to activate a mammalian SNORF62 receptor to identify a compound which activates the mammalian SNORF62 receptor which comprises: (a) contacting cells transfected with and expressing the mammalian SNORF62 receptor with the plurality of compounds not known to activate the mammalian SNORF62 receptor, under conditions permitting activation of the mammalian SNORF62 receptor; (b) determining whether the activity of the mammalian SNORF62 receptor is increased in the presence of one or more of the compounds; and if so (c) separately determining whether the activation of the mammalian SNORF62 receptor is increased by any compound included in the plurality of compounds, so as to thereby identify each compound which activates the mammalian SNORF62 receptor.

This invention yet further provides a method of screening a plurality of chemical compounds not known to activate a mammalian SNORF72 receptor to identify a compound which activates the mammalian SNORF72 receptor which comprises: (a) contacting cells transfected with and expressing the mammalian SNORF72 receptor with the plurality of compounds not known to activate the mammalian SNORF72 receptor, under conditions permitting activation of the mammalian SNORF72 receptor; (b) determining whether the activity of the mammalian SNORF72 receptor is increased in the presence of one or more of the compounds; and if so (c) separately determining whether the activation of the mammalian SNORF72 receptor is increased by any compound included in the plurality of compounds, so as to thereby identify each compound which activates the mammalian SNORF72 receptor.

In an embodiment, the mammalian SNORF62 receptor is a human SNORF62 receptor, a rat SNORF62a receptor or a rat SNORF62b receptor. In a further embodiment, the mammalian SNORF72 receptor is a human SNORF72 receptor or a rat SNORF72 receptor.

This invention provides a method of screening a plurality of chemical compounds not known to inhibit the activation of a mammalian NMU receptor to identify a compound which inhibits the activation of the mammalian NMU receptor, which comprises: (a) contacting cells transfected with and expressing the mammalian NMU receptor with the plurality of compounds in the presence of a known mammalian NMU receptor agonist, under conditions permitting activation of the mammalian NMU receptor; (b) determining whether the extent or amount of activation of the mammalian NMU receptor is reduced in the presence of one or more of the compounds, relative to the extent or amount of activation of the mammalian NMU receptor in the absence of such one or more compounds; and if so (c) separately determining whether each such compound inhibits activation of the mammalian NMU receptor for each compound included in the plurality of compounds, so as to thereby identify any compound included in such plurality of compounds which inhibits the activation of the mammalian NMU receptor.

In one embodiment, the mammalian NMU receptor is a human SNORF62 receptor, a rat SNORF62a receptor or a rat SNORF62b receptor. In a further embodiment, the mammalian NMU receptor is a human SNORF72 receptor or a rat SNORF72 receptor. In another embodiment, wherein the cell is a mammalian cell. In another embodiment, the mammalian cell is non-neuronal in origin. In another embodiment, the non-neuronal cell is a COS-7 cell, a 293 human embryonic kidney cell, a LM(tk−) cell or an NIH-3T3 cell.

This invention also provides a composition, for example, a pharmaceutical composition, comprising a compound identified by a method according to this invention in an amount effective to increase mammalian NMU receptor activity and a carrier, for example, a pharmaceutically acceptable carrier.

This invention also provides a composition, for example, a pharmaceutical composition, comprising a compound identified by a method according to this invention in an amount effective to increase mammalian SNORF62 receptor activity and a carrier, for example, a pharmaceutically acceptable carrier.

This invention also provides a composition, for example, a pharmaceutical composition, comprising a compound identified by a method according to this invention in an amount effective to increase mammalian SNORF72 receptor activity and a carrier, for example, a pharmaceutically acceptable carrier.

This invention still further provides a composition, for example, a pharmaceutical composition, comprising a compound identified by a method according to this invention in an amount effective to decrease mammalian NMU receptor activity and a carrier, for example, a pharmaceutically acceptable carrier.

This invention still further provides a composition, for example, a pharmaceutical composition, comprising a compound identified by a method according to this invention in an amount effective to decrease mammalian SNORF62 receptor activity and a carrier, for example, a pharmaceutically acceptable carrier.

This invention still further provides a composition, for example, a pharmaceutical composition, comprising a compound identified by a method according to this invention in an amount effective to decrease mammalian SNORF72 receptor activity and a carrier, for example, a pharmaceutically acceptable carrier.

Furthermore, this invention provides a method of treating an abnormality in a subject wherein the abnormality is alleviated by increasing the activity of a mammalian SNORF62 receptor which comprises administering to the subject a compound which is a mammalian SNORF62 receptor agonist in an amount effective to treat the abnormality.

Furthermore, this invention provides a method of treating an abnormality in a subject wherein the abnormality is alleviated by increasing the activity of a mammalian SNORF72 receptor which comprises administering to the subject a compound which is a mammalian SNORF72 receptor agonist in an amount effective to treat the abnormality.

In one embodiment, the abnormality is a regulation of a steroid hormone disorder, an epinephrine release disorder, a gastrointestinal disorder, a cardiovascular disorder, an electrolyte balance disorder, hypertension, diabetes, a respiratory disorder, asthma, a reproductive function disorder, an immune disorder, an endocrine disorder, a musculoskeletal disorder, a neuroendocrine disorder, a cognitive disorder, a memory disorder, somatosensory and neurotransmission disorders, metabolic disorders, a motor coordination disorder, a sensory integration disorder, a motor integration disorder, a dopaminergic function disorder, an appetite disorder, such as anorexia or obesity, a sensory transmission disorder, drug addiction, an olfaction disorder, an autonomic nervous system disorder, pain, neuropsychiatric disorders, affective disorder, migraine, circadian disorders, visual disorders, urinary disorders, blood coagulation-related disorders, developmental disorders, or ischemia-reperfusion injury-related diseases.

In a further embodiment, the abnormality is Addison's disease, Cushing's disease or a stress-related disorder. In yet another embodiment, the compounds and/or compositions of the present invention may be used to prevent miscarriage, induce labor or treat dysmenorrhea.

This invention additionally provides a method of treating an abnormality in a subject wherein the abnormality is alleviated by decreasing the activity of a mammalian SNORF62 receptor which comprises administering to the subject a compound which is a mammalian SNORF62 receptor antagonist in an amount effective to treat the abnormality.

This invention additionally provides a method of treating an abnormality in a subject wherein the abnormality is alleviated by decreasing the activity of a mammalian SNORF72 receptor which comprises administering to the subject a compound which is a mammalian SNORF72 receptor antagonist in an amount effective to treat the abnormality.

In one embodiment, the abnormality is a regulation of a steroid hormone disorder, an epinephrine release disorder, a gastrointestinal disorder, a cardiovascular disorder, an electrolyte balance disorder, hypertension, diabetes, a respiratory disorder, asthma, a reproductive function disorder, an immune disorder, an endocrine disorder, a musculoskeletal disorder, a neuroendocrine disorder, a cognitive disorder, a memory disorder, somatosensory and neurotransmission disorders, metabolic disorders, a motor coordination disorder, a sensory integration disorder, a motor integration disorder, a dopaminergic function disorder, an appetite disorder, such as anorexia or obesity, a sensory transmission disorder, drug addiction, an olfaction disorder, an autonomic nervous system disorder, pain, neuropsychiatric disorders, affective disorder, migraine, circadian disorders, visual disorders, urinary disorders, blood coagulation-related disorders, developmental disorders, or ischemia-reperfusion injury-related diseases.

In one embodiment, the mammalian NMU receptor is a human SNORF62 receptor, a rat SNORF62a receptor or a rat SNORF62b receptor. In another embodiment, the mammalian NMU receptor is a human SNORF72 receptor or a rat SNORF72 receptor.

This invention also provides a process for making a composition of matter which specifically binds to a mammalian NMU receptor which comprises identifying a chemical compound using a process in accordance with this invention and then synthesizing the chemical compound or a novel structural and functional analog or homolog thereof.

This invention also provides a process for making a composition of matter which specifically binds to a mammalian SNORF62 receptor which comprises identifying a chemical compound using a process in accordance with this invention and then synthesizing the chemical compound or a novel structural and functional analog or homolog thereof.

This invention also provides a process for making a composition of matter which specifically binds to a mammalian SNORF72 receptor which comprises identifying a chemical compound using a process in accordance with this invention and then synthesizing the chemical compound or a novel structural and functional analog or homolog thereof.

This invention further provides a process for preparing a composition, for example a pharmaceutical composition which comprises admixing a carrier, for example, a pharmaceutically acceptable carrier, and a pharmaceutically effective amount of a chemical compound identified by a process in accordance with this invention or a novel structural and functional analog or homolog thereof.

In one embodiment, the mammalian NMU receptor is a mammalian SNORF62 receptor. In another embodiment, the mammalian NMU receptor is a mammalian SNORF72 receptor. In a further embodiment, the mammalian SNORF62 receptor is a human SNORF62 receptor, a rat SNORF62a receptor or a rat SNORF62b receptor. In a further embodiment, the mammalian SNORF72 receptor is a human SNORF72 receptor or a rat SNORF72 receptor.

Thus, once the gene for a targeted receptor subtype is cloned, it is placed into a recipient cell which then expresses the targeted receptor subtype on its surface. This cell, which expresses a single population of the targeted human receptor subtype, is then propagated resulting in the establishment of a cell line. This cell line, which constitutes a drug discovery system, is used in two different types of assays: binding assays and functional assays. In binding assays, the affinity of a compound for both the receptor subtype that is the target of a particular drug discovery program and other receptor subtypes that could be associated with side effects are measured. These measurements enable one to predict the potency of a compound, as well as the degree of selectivity that the compound has for the targeted receptor subtype over other receptor subtypes. The data obtained from binding assays also enable chemists to design compounds toward or away from one or more of the relevant subtypes, as appropriate, for optimal therapeutic efficacy. In functional assays, the nature of the response of the receptor subtype to the compound is determined. Data from the functional assays show whether the compound is acting to inhibit or enhance the activity of the receptor subtype, thus enabling pharmacologists to evaluate compounds rapidly at their ultimate human receptor subtypes targets permitting chemists to rationally design drugs that will be more effective and have fewer or substantially less severe side effects than existing drugs.

Approaches to designing and synthesizing receptor subtype-selective compounds are well known and include traditional medicinal chemistry and the newer technology of combinatorial chemistry, both of which are supported by computer-assisted molecular modeling. With such approaches, chemists and pharmacologists use their knowledge of the structures of the targeted receptor subtype and compounds determined to bind and/or activate or inhibit activation of the receptor subtype to design and synthesize structures that will have activity at these receptor subtypes.

Combinatorial chemistry involves automated synthesis of a variety of novel compounds by assembling them using different combinations of chemical building blocks. The use of combinatorial chemistry greatly accelerates the process of generating compounds. The resulting arrays of compounds are called libraries and are used to screen for compounds ("lead compounds") that demonstrate a sufficient level of activity at receptors of interest. Using combinatorial chemistry it is possible to synthesize "focused" libraries of compounds anticipated to be highly biased toward the receptor target of interest.

Once lead compounds are identified, whether through the use of combinatorial chemistry or traditional medicinal chemistry or otherwise, a variety of homologs and analogs are prepared to facilitate an understanding of the relationship between chemical structure and biological or functional activity. These studies define structure activity relationships which are then used to design drugs with improved potency, selectivity and pharmacokinetic properties. Combinatorial chemistry is also used to rapidly generate a variety of structures for lead optimization. Traditional medicinal chemistry, which involves the synthesis of compounds one at a time, is also used for further refinement and to generate compounds not accessible by automated techniques. Once such drugs are defined the production is scaled up using standard chemical manufacturing methodologies utilized throughout the pharmaceutical and chemistry industry.

This invention will be better understood from the Experimental Details which follow. However, one skilled in the art will readily appreciate that the specific methods and results discussed are merely illustrative of the invention as described more fully in the claims which follow thereafter.

Experimental Details

Materials and Methods

Isolation of a Full-Length Human SNORF62 Receptor

The SwissPlus database was searched for G protein-coupled receptor sequences (GPCRs) using a select set of known GPCRs and the Wisconsin Package (GCG, Genetics Computer Group, Madison, Wis.). One sequence, O43664, was found which was most similar to the neurotensin receptor 1 (31% identity), as well as the recently identified motilin receptor, GPR38 (33% identity). O43664 was then chosen to be cloned for use in ligand-identification screens.

Before cloning the full-length receptor, the 5' and 3' ends of the coding sequence were verified by 5'/3' Rapid Amplification of cDNA Ends (RACE), using human hypothalamic Marathon-Ready cDNA (Clontech, Palo Alto, Calif.), the Marathon adaptor primers AP1 and AP2 (Clontech), and the primers JAB620, JAB621, JAB623, JAB624 and JAB622 set forth below.

A band of approximately 550 bp from the 5' RACE reaction was isolated from an agarose gel using the Qiaquick gel extraction kit (QIAGEN, Valencia, Calif.) and sequenced with JAB622. The sequence of this band indicated that the actual coding sequence of this receptor is longer than the sequence represented in the public database by 69 bp, coding for an additional potential initiating methionine 23 amino acids upstream from the methionine indicated by O43664. In addition, this 5' RACE sequence included some 5' untranslated sequence and an in-frame stop codon upstream from the new methionine. Sequencing of 3' RACE products revealed a sequence identical to the 3' end of O43664, in addition to some 3' untranslated sequence. The new (longer) coding sequence was named SNORF62.

From the new 5' untranslated sequence upstream from the new methionine and the 3' untranslated sequence, new primers were designed to amplify the entire SNORF62 sequence from human stomach cDNA using the Expand Long PCR system (Roche Biochemicals, Indianapolis, Ind.). The primers JAB648 and, JAB627 were designed to incorporate restriction sites for subcloning into the expression vector pEXJ.T3T7. The resulting PCR product of approximately 1330 bp was digested with HindIII and BamHI and subcloned into the HindIII/BamHI site of pEXJ.T3T7. This construct of SNORF62 with the additional methionine, subcloned into pEXJ.T3T7 was named pEXJ.T3T7-hS-NORF62-f.

Primers and probes used in the identification of SNORF62:

```
JAB620 = 5'-CCACGAAGATCAGCAGGTATGTGG-3'           (SEQ ID NO: 9)

JAB621 = 5'-GGCATGAACAGCTCTGTCTGCTGG-3'          (SEQ ID NO: 10)

JAB623 = 5'-CCAGCCGCTTCCGAGAGACCTTCC-3'          (SEQ ID NO: 11)

JAB624 = 5'-GCCTGCTGCCATCGCCTCAGACCC-3'          (SEQ ID NO: 12)

JAB622 = 5'-GCCCCAGGTACTTGAGTCTCAGTG-3'          (SEQ ID NO: 13)

JAB648 = 5'-ATCTATAAGCTTCGGAGGGTGGAAGCCGGGGTCTC-3'    (SEQ ID NO: 14)

JAB627 = 5'-ATCTATGGATCCTCAGGATGGATCGGTCTCTTGCTG-3'   (SEQ ID NO: 15)
```

Isolation of the Rat SNORF62a and Rat SNORF62b Receptors

To obtain a fragment of the rat homologue of SNORF62, 100 ng of rat genomic DNA (Clontech, Palo Alto, Calif.) and 1 μl of rat testes QUICK clone cDNA (Clontech) were amplified with forward PCR primers corresponding to TM1 (BB1611) or the 2nd intracellular loop (BB1614) and a reverse primer corresponding to TM6 (BB1612) of the mouse SNORF62 (GenEMBL Database Accession Number AF044602). PCR was performed with the Expand Long Template PCR System (Roche Molecular Biochemicals, Indianapolis, Ind.) under the following conditions: 30 seconds at 94° C., 45 seconds at 49° C. to 67.7° C., 2 minutes at 68° C. for 40 cycles; with a pre- and post-incubation of 5 minutes at 94° C. and 7 minutes at 68° C., respectively. Bands of 430 and 700 bp from 6 independent reactions were isolated from a TAE gel, purified using the GENECLEAN SPIN Kit (BIO101, Carlsbad, Calif.) and sequenced using the ABI BigDye cycle sequencing protocol and ABI 377 sequencers (ABI, Foster City, Calif.). Sequences were analyzed using the Wisconsin Package (GCG, Genetics Computer Group, Madison, Wis.). A consensus sequence was determined for these products.

5' and 3' RACE

The full length rat SNORF62 sequence was determined utilizing the Clonetch Marathon cDNA Amplification kit (Clontech, Palo Alto, Calif.) for 5'/3' Rapid Amplification of cDNA ends (RACE). Nested PCR were performed according to the Marathon cDNA Amplification protocol using Marathon-Ready rat spleen cDNA (Clontech). For 5' RACE, the initial PCR was performed with the supplier's Adaptor Primer 1 and BB1631, a reverse primer from TM3 of the consensus sequence described above. Two μl of the initial PCR reaction was re-amplified using the Adaptor Primer 2 and BB1630, a reverse primer from the 1st extracellular loop. PCR was performed with Advantage Klentaq Polymerase (Clontech, Palo Alto, Calif.) under the following conditions: 5 minutes at 94° C.; 5 cycles of 94° C. for 30 seconds and 72° C. for 3 minutes; 5 cycles of 94° C. for 30 seconds and 70° C. for 3 minutes; 25 cycles (initial PCR) or 18 cycles (nested PCR) of 94° C. for 30 seconds and 68° C. for 3 minutes; 68° C. hold for 7 minutes, and 4° C. hold until the products were ready for analysis. 400 and 800 bp fragments were isolated from a 1% agarose TAE gel using the GENECLEAN SPIN Kit and sequenced as above.

A second reaction was performed for 5' RACE using Marathon-Ready rat spleen and testes cDNA (Clontech). The initial PCR was performed with the supplier's Adaptor Primer 1 and BB1650, a reverse primer from TM1 of the RACE fragment described above. Two μls of the initial PCR reaction was re-amplified using the Adaptor Primer 2 and BB1649, a reverse primer from the amino terminus. PCR was performed as described above. 300 and 700 bp fragments were isolated from a 1% agarose TAE gel using the GENECLEAN SPIN Kit and sequenced as above.

For 3' RACE, initial PCR was performed using Marathon-Ready rat spleen with the supplier's Adapter Primer 1 and BB1632, a forward primer from TM5 of the consensus sequence described above. Two μls of this initial PCR reaction was re-amplified using Adaptor Primer 2 and BB1633, a forward primer from the 3rd intracellular loop. PCR was performed with Advantage Klentaq Polymerase (Clontech, Palo Alto, Calif.) under the following conditions: 5 minutes at 94° C.; 5 cycles of 94° C. for 30 seconds and 72° C. for 3 minutes; 5 cycles of 94° C. for 30 seconds and 70° C. for 3 minutes; 25 cycles (initial PCR) or 18 cycles (nested PCR) of 94° C. for 30 seconds and 68° C. for 3 minutes; 68° C. hold for 7 minutes, and 4° C. hold until the products were ready for analysis. A 1000 bp fragment was isolated from a 1% agarose TAE gel using the GENECLEAN SPIN Kit and sequenced as above.

Primers and probes used in the identification of rat SNORF62a and rat SNORF62b:

obtained from cDNA using standard molecular biology techniques. For example, a forward PCR primer designed in the 5'UT and a reverse PCR primer designed in the 3'UT may be used to amplify a full-length, intronless receptor from cDNA. Standard molecular biology techniques could be used to subclone this gene into a mammalian expression vector.

Approach #2: Standard molecular biology techniques may be used to screen commercial cDNA phage libraries of the species of interest by hybridization under reduced stringency with a $^{32}$P-labeled oligonucleotide probe corresponding to a fragment of the sequences shown in FIGS. 1A–1B. One may isolate a full-length SNORF62 receptor by obtaining a plaque purified clone from the lambda libraries and then subjecting the clone to direct DNA sequencing. Alternatively, standard molecular biology techniques could be used to screen cDNA plasmid libraries by PCR amplification of library pools using primers designed against a partial species homolog sequence. A full-length clone may be isolated by Southern hybridization of colony lifts of positive pools with a $^{32}$P-oligonucleotide probe.

Approach #3: 3' and 5' RACE may be utilized to generate PCR products from cDNA derived from the species of interest expressing SNORF62 which contain the additional sequence of SNORF62. These RACE PCR products may then be sequenced to determine the additional sequence. This new sequence is then used to design a forward PCR primer in the 5'UT and a reverse primer in the 3'UT. These primers are then used to amplify a full-length SNORF62 clone from cDNA.

Examples of other species include, but are not limited to, mouse, dog, monkey, hamster and guinea pig.

Isolation of a Full-Length Human SNORF72 Receptor

```
BB1611 = 5'-TAC CTG CTG ATC TTC GTG GTG GG-3'        (SEQ ID NO: 30)

BB1612 = 5'-CAG TGC AAA CAG CAT CTT GGT CAC-3'       (SEQ ID NO: 31)

BB1614 = 5'-TAT GTG GCC GTG GTG CGC CCA CTC C-3'     (SEQ ID NO: 32)

BB1630 = 5'-CCA CCT GCA CCC AGC TGG AAT GGG-3'       (SEQ ID NO: 33)

BB1631 = 5'-ACT GAA GCC AGG CAG ACA GTC TCC-3'       (SEQ ID NO: 34)

BB1632 = 5'-TGG TCA CCA TCA GTG TGC TGT ACC-3'       (SEQ ID NO: 35)

BB1633 = 5'-TGC GGA GGG AGA GGA TGT TGC TCC-3'       (SEQ ID NO: 36)

BB1649 = 5'-CCC AAG TAC TTC AGC CTC AGG TCC-3'       (SEQ ID NO: 37)

BB1650 = 5'-GGT CAA CCC GTT GCC CAG AGT GCC-3'       (SEQ ID NO: 38)
```

Isolation of Other Species Homologs of SNORF62 Receptor cDNA

A nucleic acid sequence encoding a SNORF62 receptor cDNA from other species may be isolated using standard molecular biology techniques and approaches such as those described below:

Approach #1: A genomic library (e.g., cosmid, phage, P1, BAC, YAC) generated from the species of interest may be screened with a $^{32}$P— labeled oligonucleotide probe corresponding to a fragment of the human SNORF62 receptor whose sequence is shown in FIGS. 1A–1B to isolate a genomic clone. The full-length sequence may be obtained by sequencing this genomic clone. If one or more introns are present in the gene, the full-length intronless gene may be A search of the public domain databases revealed an amino acid sequence that was 46% identical to the amino acid sequence of SNORF62. This sequence was given the name human SNORF72. Primers were designed against the 5'- and 3'-untranslated regions of SNORF72, with restriction sites incorporated for subcloning purposes. GSL42 is a forward primer in the 5' untranslated region with a NotI site incorprated into the 5' end of the primer, and GSL43 is a reverse primer in the 3' untranslated region with an XbaI site incorporated into the 5' end of the primer. These primers were used to amplify the full-length sequence from human whole-brain cDNA using the Expand Long Template PCR system (Roche Biochemicals, Indianapolis, Ind.). Sequencing of several clones from independent PCR reactions indicated that the acutal sequence of SNORF72 differed from the published sequence at five base positions, four of which changed the amino acid sequence of the receptor. This sequence-verified SNORF72 clone was subcloned into the 4:0 NotI/XbaI site of the mammalian expression vector pEXJ.T3T7 and named pEXJ.T3T7-hSNORF72-f.

Primers and probes used in the identification of SNORF72:

```
GSL42 = 5'-ATCTATGCGGCCGCTTGAAACAGAGCCTCGTACC-3'  (SEQ ID NO: 16)

GSL43 = 5'-ATCTATTCTAGAGTTGTAAGAGCCATTCTACCTC-3'  (SEQ ID NO: 17)
```

Isolation of a Full-Length Rat SNORF72 Receptor

A pair of oligo primers, BB1606 and BB1607 (set forth below), were synthesized based on sequence of the human SNORF72 gene. A PCR reaction was performed using this primer pair on rat brain cDNA from Clontech. The PCR condition used was 95° C. for 5 minutes for initial denaturation, 94° C. for 30 seconds followed by 50° C. for 30 seconds and 68° C. for 90 seconds for total of 40 cycles, finished with extension at 68° C. for 7 minutes. The PCR product was sequenced and another pair of oligo primers, BB1609 and BB1610 (set forth below), were synthesized based on the sequencing information obtained. An oligo(dT) primed cDNA library from rat hypothalamus was screened by PCR using BB1609 and BB1610 as primers, and three positive pools were found from the first 188 pools screened. The PCR condition used was: 94° C. for 4 minutes for initial denaturation, 94° C. for 30 seconds followed by 68° C. for 90 seconds for total of 40 cycles, finished with extension at 68° C. for 7 minutes. After two rounds of sib-selection, colonies were plated and positive clones were screened by hybridization with a radiolabeled oligonucleotide probe KS2008. A positive clone containing a 3.5 kb cDNA insert was isolated and found to contain the full coding region of rat SNORF72 by sequence analysis.

Primers and probes used in the identification of rat SNORF72:

techniques. For example, a forward PCR primer designed in the 5'UT and a reverse PCR primer designed in the 3'UT may be used to amplify a full-length, intronless receptor from cDNA. Standard molecular biology techniques could be used to subclone this gene into a mammalian expression vector.

Approach #2: Standard molecular biology techniques may be used to screen commercial cDNA phage libraries of the species of interest by hybridization under reduced stringency with a $^{32}$P-labeled oligonucleotide probe corresponding to a fragment of the sequences shown in FIGS. 3A–3B. One may isolate a full-length SNORF72 receptor by obtaining a plaque purified clone from the lambda libraries and then subjecting the clone to direct DNA sequencing. Alternatively, standard molecular biology techniques could be used to screen cDNA plasmid libraries by PCR amplification of library pools using primers designed against a partial species homolog sequence. A full-length clone may be isolated by Southern hybridization of colony lifts of positive pools with a $^{32}$P-oligonucleotide probe.

Approach #3: 3' and 5' RACE may be utilized to generate PCR products from cDNA derived from the species of interest expressing SNORF72 which contain the additional sequence of SNORF72. These RACE PCR products may then be sequenced to determine the additional sequence. This new sequence is then used to design a forward PCR primer in the 5'UT and a reverse primer in the 3'UT. These primers are then used to amplify a full-length SNORF72 clone from cDNA.

Examples of other species include, but are not limited to, mouse, dog, monkey, hamster and guinea pig.

Host Cells

```
BB1606 = 5'-TCTATGAGATGTGGCGCAACTACC-3'                              (SEQ ID NO: 39)

BB1607 = 5'-AACACTAAGACCAAGACAAACAGC-3'                              (SEQ ID NO: 40)

BB1609 = 5'-GTCACCACGGTTAGCGTAGAGCGC-3'                              (SEQ ID NO: 41)

BB1610 = 5'-GAGGGTCTGTGAATATTCACAGCC-3'                              (SEQ ID NO: 42)

KS2008 = 5'-CCCAACGGGTCCTCCGTACCTGGCTCAGCCACCTGCACAGTCACC-3'         (SEQ ID NO: 43)
```

Isolation of Other Species Homologs of SNORF72 Receptor cDNA

A nucleic acid sequence encoding a SNORF72 receptor cDNA from other species may be isolated using standard molecular biology techniques and approaches such as those described below:

Approach #1: A genomic library (e.g., cosmid, phage, P1, BAC, YAC) generated from the species of interest may be screened with a $^{32}$P— labeled oligonucleotide probe corresponding to a fragment of the human SNORF72 receptor whose sequence is shown in FIGS. 3A–3B to isolate a genomic clone. The full-length sequence may be obtained by sequencing this genomic clone. If one or more introns are present in the gene, the full-length intronless gene may be obtained from cDNA using standard molecular biology A broad variety of host cells can be used to study heterologously expressed proteins. These cells include but are not limited to mammalian cell lines such as; COS-7, CHO, LM(tk⁻), HEK293, etc.; insect cell lines such as; Sf9, Sf21, *Trichoplusia ni* 5B-4, etc.; amphibian cells such as *Xenopus* oocytes; assorted yeast strains; assorted bacterial cell strains; and others. Culture conditions for each of these cell types is specific and is known to those familiar with the art.

COS-7 cells are grown on 150 mm plates in DMEM with supplements (Dulbecco's Modified Eagle Medium with 10% bovine calf serum, 4 mM glutamine, 100 units/ml penicillin 100 μg/ml streptomycin) at 37° C., 5% $CO_2$. Stock plates of COS-7 cells are trypsinized and split 1:6 every 3–4 days.

Transient Expression

DNA encoding proteins to be studied can be transiently expressed in a variety of mammalian, insect, amphibian, yeast, bacterial and other cells lines by several transfection methods including but not limited to; calcium phosphate-mediated, DEAE-dextran mediated; liposomal-mediated, viral-mediated, electroporation-mediated, and microinjection delivery. Each of these methods may require optimization of assorted experimental parameters depending on the DNA, cell line, and the type of assay to be subsequently employed.

A typical protocol for the DEAE-dextran method as applied to COS-7 and HEK293 cells is described as follows. Cells to be used for transfection are split 24 hours prior to the transfection to provide flasks which are 70–80% confluent at the time of transfection. Briefly, 8 μg of receptor DNA plus 8 μg of any additional DNA needed (e.g. $G_\alpha$ protein expression vector, reporter construct, antibiotic resistance marker, mock vector, etc.) are added to 9 ml of complete DMEM plus DEAE-dextran mixture (10 mg/ml in PBS). Cells plated into a T225 flask (sub-confluent) are washed once with PBS and the DNA mixture is added to each flask. The cells are allowed to incubate for 30 minutes at 37° C., 5% $CO_2$. Following the incubation, 36 ml of complete DMEM with 80 μM chloroquine is added to each flask and allowed to incubate an additional 3 hours. The medium is then aspirated and 24 ml of complete medium containing 10% DMSO for exactly 2 minutes and then aspirated. The cells are then washed 2 times with PBS and 30 ml of complete DMEM added to each flask. The cells are then allowed to incubate over night. The next day the cells are harvested by trypsinization and reseeded into 96 well plates.

Stable Expression

Heterologous DNA can be stably incorporated into host cells, causing the cell to perpetually express a foreign protein. Methods for the delivery of the DNA into the cell are similar to those described above for transient expression but require the co-transfection of an ancillary gene to confer drug resistance on the targeted host cell. The ensuing drug resistance can be exploited to select and maintain cells that have taken up the DNA. An assortment of resistance genes are available including but not restricted to neomycin, kanamycin, and hygromycin. For purposes of studies concerning the receptor of this invention, stable expression of a heterologous receptor protein is typically carrier out in, mammalian cells including but not necessarily restricted to, CHO, HEK293, LM(tk−), etc. In addition native cell lines that naturally carry and express the nucleic acid sequences for the receptor may be used without the need to engineer the receptor complement.

Functional Assays

Cells expressing the receptor DNA of this invention may be used to screen for ligands to said receptor using functional assays. Once a ligand is identified the same assays may be used to identify agonists or antagonists of the receptor that may be employed for a variety of therapeutic purposes.

It is well known to those in the art that the over-expression of a G-protein coupled receptor can result in the constitutive activation of intracellular signaling pathways. In the same manner, over-expression of the receptors of the present invention in any cell line as described above, can result in the activation of the functional responses described below, and any of the assays herein described can be used to screen for agonist, partial agonist, inverse agonist and antagonist ligands of the SNORF62 and SNORF72 receptors.

A wide spectrum of assays can be employed to screen for the presence of receptor SNORF62 and SNORF72 ligands. These assays range from traditional measurements of total inositol phosphate accumulation, cAMP levels, intracellular calcium mobilization, and potassium currents, for example; to systems measuring these same second messengers but which have been modified or adapted to be of higher throughput, more generic and more sensitive; to cell based assays reporting more general cellular events resulting from receptor activation such as metabolic changes, differentiation, cell division/proliferation. Description of several such assays follow.

Cyclic AMP (cAMP) Assay

The receptor-mediated stimulation or inhibition of cyclic AMP (cAMP) formation may be assayed in cells expressing the receptors. COS-7 cells are transiently transfected with the receptor gene using the DEAE-dextran method and plated in 96-well plates. 48 hours after transfection, cells are washed twice with Dulbecco's phosphate buffered saline (PBS) supplemented with 10 mM HEPES, 10 mM glucose and 5 mM theophylline and are incubated in the same buffer for 20 min at 37° C., in 5% $CO_2$. Test compounds are added and cells are incubated for an additional 10 min at 37° C. The medium is then aspirated and the reaction stopped by the addition of 100 mM HCl. The plates are stored at −20° C. for 2–5 days. For cAMP measurement, plates are thawed and the cAMP content in each well is measured by cAMP Scintillation Proximity Assay (Amersham Pharmacia Biotech). Radioactivity is quantified using microbeta Trilux counter (Wallac).

Arachidonic Acid Release Assay

Cells expressing the receptor are seeded into 96 well plates or other vessels and grown for 3 days in medium with supplements. $^3$H-arachidonic acid (specific activity=0.75 μCi/ml) is delivered as a 100 μL aliquot to each well and samples are incubated at 37° C., 5% $CO_2$ for 18 hours. The labeled cells are washed three times with medium. The wells are then filled with medium and the assay is initiated with the addition of test compounds or buffer in a total volume of 250 μL. Cells are incubated for 30 min at 37° C., 5% $CO_2$.

Supernatants are transferred to a microtiter plate and evaporated to dryness at 75° C. in a vacuum oven. Samples are then dissolved and resuspended in 25 μL distilled water. Scintillant (300 μL) is added to each well and samples are counted for $^3$H in a Trilux plate reader. Data are analyzed using nonlinear regression and statistical techniques available in the GraphPAD Prism package (San Diego, Calif.).

Intracellular Calcium Mobilization Assays

The intracellular free calcium ($Ca^{2+}$) concentration may be measured by microspectrofluorimetry using the fluorescent indicator dye Fura-2/AM (Bush et al., 1991). Cells expressing the receptor are seeded onto a 35 mm culture dish containing a glass coverslip insert and allowed to adhere overnight. Cells are then washed with HBS and loaded with 100 μL of Fura-2/AM (10 μM) for 20 to 40 min. After washing with HBS to remove the Fura-2/AM solution, cells are equilibrated in HBS for 10 to 20 min. Cells are then visualized under the 40× objective of a Leitz Fluovert FS microscope and fluorescence emission is determined at 510 nM with excitation wavelengths alternating between 340 nM and 380 nM. Raw fluorescence data are converted to $Ca^{2+}$ concentrations using standard $Ca^{2+}$ concentration curves and software analysis techniques.

In another method, the measurement of intracellular $Ca^{2+}$ can also be performed on a 96-well (or higher) format and with alternative $Ca^{2+}$-sensitive indicators, preferred examples of these are: aequorin, Fluo-3, Fluo-4, Fluo-5, Calcium Green-1, Oregon Green, and 488 BAPTA. After activation of the receptors with agonist ligands the emission elicited by the change of intracellular $Ca^{2+}$ concentration can be measured by a luminometer, or a fluorescence imager; a preferred example of this is the fluorescence imager plate reader (FLIPR™, Molecular Devices).

Cells expressing the receptor of interest are plated into clear, flat-bottom, black-walled 96-well plates (Costar) at a density of 80,000–150,000 cells per well and allowed to incubate for 48 hr at 5% $CO_2$, 37° C. The growth medium is aspirated and 100 µL of loading medium containing Fluo-3 dye is added to each well. The loading medium contains: 20 mM HEPES (Sigma), 0.1% BSA (Sigma), dye/pluronic acid mixture (e.g. 1 mM Fluo-3/AM (Molecular Probes) and 10% pluronic acid (Molecular Probes) mixed immediately before use), and 2.5 mM probenecid (Sigma) (prepared fresh). The cells are allowed to incubate for about 1 hour at 5% $CO_2$, 37° C.

The compounds of interest are diluted in wash buffer (Hank's BSS (without phenol red), 20 mM HEPES, 2.5 mM probenecid) to a 4× final concentration and aliquoted into a clear v-bottom plate (Nunc). Following the dye incubation, the cells are washed 4 times to remove excess dye using a Denley plate washer. 100 µL final volume of wash buffer is then added to each cell well. Compounds are added to the cell plates and responses are measured using the FLIPR™ instrument. The data are then collected and analyzed using the FLIPR™ software and Graphpad Prism.

Antagonist ligands are identified by the inhibition of the signal elicited by agonist ligands.

GTPγS Functional Assay

Membranes from cells expressing the receptor are suspended in assay buffer (e.g., 50 mM Tris, 100 mM NaCl, 5 mM $MgCl_2$, 10 µM GDP, pH 7.4) with or without protease inhibitors (e.g., 0.1% bacitracin). Membranes are incubated on ice for 20 minutes, transferred to a 96-well Millipore microtiter GF/C filter plate and mixed with GTPγ$^{35}$S (e.g., 250,000 cpm/sample, specific activity ~1000 Ci/mmol) plus or minus unlabeled GTPγS (final concentration=100 µM). Final membrane protein concentration ≈90 µg/ml. Samples are incubated in the presence or absence of test compounds for 30 min. at room temperature, then filtered on a Millipore vacuum manifold and washed three times with cold (4° C.) assay buffer. Samples collected in the filter plate are treated with scintillant and counted for $^{35}$S in a Trilux (Wallac) liquid scintillation counter. It is expected that optimal results are obtained when the receptor membrane preparation is derived from an appropriately engineered heterologous expression system, i.e., an expression system resulting in high levels of expression of the receptor and/or expressing G-proteins having high turnover rates (for the exchange of GDP for GTP). GTPγS assays are well-known to those skilled in the art, and it is contemplated that variations on the method described above, such as are described by Tian et al. (1994) or Lazareno and Birdsall (1993), may be used.

Microphysiometric Assay

Because cellular metabolism is intricately involved in a broad range of cellular events (including receptor activation of multiple messenger pathways), the use of microphysiometric measurements of cell metabolism can in principle provide a generic assay of cellular activity arising from the activation of any orphan receptor regardless of the specifics of the receptor's signaling pathway.

General guidelines for transient receptor expression, cell preparation and microphysiometric recording are described elsewhere (Salon, J. A. and Owicki, J. A., 1996). Typically cells expressing receptors are harvested and seeded at 3×10$^5$ cells per microphysiometer capsule in complete media 24 hours prior to an experiment. The media is replaced with serum free media 16 hours prior to recording to minimize non-specific metabolic stimulation by assorted and ill-defined serum factors. On the day of the experiment the cell capsules are transferred to the microphysiometer and allowed to equilibrate in recording media (low buffer RPMI 1640, no bicarbonate, no serum (Molecular Devices Corporation, Sunnyvale, Calif.) containing 0.1% fatty acid free BSA), during which a baseline measurement of basal metabolic activity is established.

A standard recording protocol specifies a 100 µl/min flow rate, with a 2 min total pump cycle which includes a 30 sec flow interruption during which the acidification rate measurement is taken. Ligand challenges involve a 1 min 20 sec exposure to the sample just prior to the first post challenge rate measurement being taken, followed by two additional pump cycles for a total of 5 min 20 sec sample exposure. Typically, drugs in a primary screen are presented to the cells at 10 µM final concentration.

Follow up experiments to examine dose-dependency of active compounds are then done by sequentially challenging the cells with a drug concentration range that exceeds the amount needed to generate responses ranging from threshold to maximal levels. Ligand samples are then washed out and the acidification rates reported are expressed as a percentage increase of the peak response over the baseline rate observed just prior to challenge.

MAP Kinase Assay

MAP kinase (mitogen activated kinase) may be monitored to evaluate receptor activation. MAP kinase is activated by multiple pathways in the cell. A primary mode of activation involves the ras/raf/MEK/MAP kinase pathway. Growth factor (tyrosine kinase) receptors feed into this pathway via SHC/Grb-2/SOS/ras. Gi coupled receptors are also known to activate ras and subsequently produce an activation of MAP kinase. Receptors that activate phospholipase C (such as Gq/G11-coupled) produce diacylglycerol (DAG) as a consequence of phosphatidyl inositol hydrolysis. DAG activates protein kinase C which in turn phosphorylates MAP kinase.

MAP kinase activation can be detected by several approaches. One approach is based on an evaluation of the phosphorylation state, either unphosphorylated (inactive) or phosphorylated (active). The phosphorylated protein has a slower mobility in SDS-PAGE and can therefore be compared with the unstimulated protein using Western blotting. Alternatively, antibodies specific for the phosphorylated protein are available (New England Biolabs) which can be used to detect an increase in the phosphorylated kinase. In either method, cells are stimulated with the test compound and then extracted with Laemmli buffer. The soluble fraction is applied to an SDS-PAGE gel and proteins are transferred electrophoretically to nitrocellulose or Immobilon. Immunoreactive bands are detected by standard Western blotting technique. Visible or chemiluminescent signals are recorded on film and may be quantified by densitometry.

Another approach is based on evaluation of the MAP kinase activity via a phosphorylation assay. Cells are stimulated with the test compound and a soluble extract is prepared. The extract is incubated at 30° C. for 10 min with gamma-$^{32}$P-ATP, an ATP regenerating system, and a specific substrate for MAP kinase such as phosphorylated heat and acid stable protein regulated by insulin, or PHAS-I. The reaction is terminated by the addition of H$_3$PO$_4$ and samples are transferred to ice. An aliquot is spotted onto Whatman P81 chromatography paper, which retains the phosphorylated protein. The chromatography paper is washed and counted for $^{32}$P in a liquid scintillation counter. Alternatively, the cell extract is incubated with gamma-$^{32}$P-ATP, an ATP regenerating system, and biotinylated myelin basic protein bound by streptavidin to a filter support. The myelin basic protein is a substrate for activated MAP kinase. The phosphorylation reaction is carried out for 10 min at 30° C.

The extract can then by aspirated through the filter, which retains the phosphorylated myelin basic protein. The filter is washed and counted for $^{32}$P by liquid scintillation counting.

Cell Proliferation Assay

Receptor activation of the orphan receptor may lead to a mitogenic or proliferative response which can be monitored via $^3$H-thymidine uptake. When cultured cells are incubated with $^3$H-thymidine, the thymidine translocates into the nuclei where it is phosphorylated to thymidine triphosphate. The nucleotide triphosphate is then incorporated into the cellular DNA at a rate that is proportional to the rate of cell growth. Typically, cells are grown in culture for 1–3 days. Cells are forced into quiescence by the removal of serum for 24 hrs. A mitogenic agent is then added to the media. 24 hrs later, the cells are incubated with $^3$H-thymidine at specific activities ranging from 1 to 10 μCi/ml for 2–6 hrs. Harvesting procedures may involve trypsinization and trapping of cells by filtration over GF/C filters with or without a prior incubation in TCA to extract soluble thymidine. The filters are processed with scintillant and counted for $^3$H by liquid scintillation counting. Alternatively, adherent cells are fixed in MeOH or TCA, washed in water, and solubilized in 0.05% deoxycholate/0.1 N NaOH. The soluble extract is transferred to scintillation vials and counted for $^3$H by liquid scintillation counting.

Alternatively, cell proliferation can be assayed by measuring the expression of an endogenous or heterologous gene product, expressed by the cell line used to transfect the orphan receptor, which can be detected by methods such as, but not limited to, florescence intensity, enzymatic activity, immunoreactivity, DNA hybridization, polymerase chain reaction, etc.

Promiscuous Second Messenger Assays

It is not possible to predict, a priori and based solely upon the GPCR sequence, which of the cell's many different signaling pathways any given receptor will naturally use.

It is possible, however, to coax receptors of different functional classes to signal through a pre-selected pathway through the use of promiscuous $G_\alpha$ subunits. For example, by providing a cell based receptor assay system with an endogenously supplied promiscuous $G_\alpha$ subunit such as $G_{\alpha15}$ or $G_{\alpha16}$ or a chimeric $G_\alpha$ subunit such as $G_{\alpha qz}$, a GPCR, which might normally prefer to couple through a specific signaling pathway (e.g., $G_s$, $G_i$, $G_q$, $G_o$, etc.), can be made to couple through the pathway defined by the promiscuous $G_\alpha$ subunit and upon agonist activation produce the second messenger associated with that subunit's pathway. In the case of $G\alpha_{15}$, $G_{\alpha16}$ and/or $G_{\alpha qz}$ this would involve activation of the $G_q$ pathway and production of the second messenger IP$_3$. Through the use of similar strategies and tools, it is possible to bias receptor signaling through pathways producing other second messengers such as Ca$^{++}$, cAMP, and K$^+$ currents, for example (Milligan and Rees, 1999).

It follows that the promiscuous interaction of the exogenously supplied $G_\alpha$ subunit with the receptor alleviates the need to carry out a different assay for each possible signaling pathway and increases the chances of detecting a functional signal upon receptor activation.

Methods for recording currents in Xenopus oocytes Oocytes are harvested from Xenopus laevis and injected with mRNA transcripts as previously described (Quick and Lester, 1994; Smith et al., 1997). The test receptor of this invention and Ga subunit RNA transcripts are synthesized using the T7 polymerase ("Message Machine," Ambion) from linearized plasmids or PCR products containing the complete coding region of the genes. Oocytes are injected with 10 ng synthetic receptor RNA and incubated for 3–8 days at 17 degrees. Three to eight hours prior to recording, oocytes are injected with 500 pg promiscuous Ga subunits mRNA in order to observe coupling to Ca$^{++}$ activated Cl$^-$ currents.

Dual electrode voltage clamp (Axon Instruments Inc.) is performed using 3 M KCl-filled glass microelectrodes having resistances of 1–2 MOhm. Unless otherwise specified, oocytes are voltage clamped at a holding potential of −80 mV. During recordings, oocytes are bathed in continuously flowing (1–3 ml/min) medium containing 96 mM NaCl, 2 mM KCl, 1.8 mM CaCl$_2$, 1 mM MgCl$_2$, and 5 mM HEPES, pH 7.5 (ND96). Drugs are applied either by local perfusion from a 10 μl glass capillary tube fixed at a distance of 0.5 mm from the oocyte, or by switching from a series of gravity fed perfusion lines.

Other oocytes may be injected with a mixture of receptor mRNAs and synthetic mRNA encoding the genes for G-protein-activated inward rectifier channels (GIRK1 and GIRK4, U.S. Pat. Nos. 5,734,021 and 5,728,535 or GIRK1 and GIRK2) or any other appropriate combinations (see, e.g., Inanobe et al., 1999). Genes encoding G-protein inwardly rectifying K$^+$ (GIRK) channels 1,2 and 4 (GIRK1, GIRK2, and GIRK4) may be obtained by PCR using the published sequences (Kubo et al., 1993; Dascal et al., 1993; Krapivinsky et al., 1995 and 1995b) to derive appropriate 5' and 3' primers. Human heart or brain cDNA may be used as template together with appropriate primers.

Heterologous expression of GPCRs in Xenopus oocytes has been widely used to determine the identity of signaling pathways activated by agonist stimulation (Gundersen et al., 1983; Takahashi et al., 1987). Activation of the phospholipase C (PLC) pathway is assayed by applying a test compound in ND96 solution to oocytes previously injected with mRNA for the human SNORF62 and observing inward currents at a holding potential of approximately −80 mV. The appearance of currents that reverse at −25 mV and display other properties of the Ca$^{++}$-activated Cl$^-$ channel is indicative of receptor-acitivation of PLC and release of IP$_3$ and intracellular Ca$^{++}$. Such activation is exhibited by GPCRs that couple to $G_q$ or $G_{11}$.

Measurement of inwardly rectifying K+(potassium) channel (GIRK) activity may be monitored in oocytes that have been co-injected with mRNAs encoding the mammalian receptor plus GIRK subunits. GIRK gene products co-assemble to form a G-protein activated potassium channel known to be activated (i.e., stimulated) by a number of GPCRs that couple to $G_i$ or $G_o$ (Kubo et al., 1993; Dascal et al., 1993). Oocytes expressing the mammalian receptor plus the GIRK subunits are tested for test compound responsitivity by measuring K$^+$ currents in elevated K$^+$ solution containing 49 mM K$^+$.

In the present invention, oocytes were harvested from Xenopus laevis and injected with mRNA transcripts as previously described (Quick and Lester, 1994; Smith et al., 1997). SNORF62 mRNA transcript was synthesized using the T7 polymerase ("Message Machine", Ambion) from linearized plasmids or PCR products containing the complete coding region of the gene. Oocytes were injected with 1–50 ng synthetic receptor RNA and incubated for 3–8 days at 17° C. Currents were recorded under dual electrode voltage clamp (Axon Instruments Inc.) with 3 M KCl-filled glass microelectrodes having resistances of 1–2 Mohm. Unless otherwise specified, oocytes were voltage clamped at a holding potential of −80 mV. During recordings, oocytes were bathed in continuously flowing (1–3 mL/min) medium containing 96 mM NaCl, 2 mM KCl, 1.8 mM $CaCl_2$, 1 mM $MgCl_2$, and 5 mM HEPES, pH 7.5 (ND96). Drugs were applied either by local perfusion from a 10 µL glass capillary tube fixed at a distance of 0.5 mm from the oocyte, or by switching from a series of gravity fed perfusion lines.

Inositol Phosphate Assay

Human SNORF62 receptor-mediated activation and human SNORF72 receptor-mediated activation of the inositol phosphate (IP) second messenger pathways were assessed by radiometric measurement of IP products.

For example, in a 96 well microplate format assay, COS-7 cells expressing the receptor of interest were plated at a density of 70,000 cells per well and allowed to incubate for 24 hours. The cells were then labeled with 0.5 µCi [$^3$H] myo-inositol overnight at 37° C., 5% $CO_2$. Immediately before the assay, the medium was removed and replaced with 180 µL of Phosphate-Buffered Saline (PBS) containing 10 mM LiCl. The plates were then incubated for 20 min at 37° C., 5% $CO_2$. Following the incubation, the cells were challenged with agonist (20 µl/well; 10× concentration) for 30 min at 37° C. The challenge was terminated by the addition of 100 µL of 5% v/v trichloroacetic acid, followed by incubation at 4° C. for greater than 30 minutes. Total IPs were isolated from the lysate by ion exchange chromatography. Briefly, the lysed contents of the wells were transferred to a Multiscreen HV filter plate (Millipore) containing Dowex AG1-X8 (200–400 mesh, formate form). The filter plates were prepared adding 100 µL of Dowex AG1-X8 suspension (50% v/v, water: resin) to each well. The filter plates were placed on a vacuum manifold to wash or elute the resin bed. Each well was first washed 2 times with 200 µl of 5 mM myo-inositol. Total [$^3$H]inositol phosphates were eluted with 75 µl of 1.2M ammonium formate/0.1M formic acid solution into 96-well plates. 200 µL of scintillation cocktail was added to each well, and the radioactivity was determined by liquid scintillation counting.

Membrane Preparations

Cell membranes expressing the receptor protein of this invention are useful for certain types of assays including but not restricted to ligand binding assays, GTP-γ-S binding assays, and others. The specifics of preparing such cell membranes may in some cases be determined by the nature of the ensuing assay but typically involve harvesting whole cells and disrupting the cell pellet by sonication in ice cold buffer (e.g. 20 mM Tris HCl, mM EDTA, pH 7.4 at 4° C.). The resulting crude cell lysate is cleared of cell debris by low speed centrifugation at 200×g for 5 min at 4° C. The cleared supernatant is then centrifuged at 40,000×g for 20 min at 4° C., and the resulting membrane pellet is washed by suspending in ice cold buffer and repeating the high speed centrifugation step. The final washed membrane pellet is resuspended in assay buffer. Protein concentrations are determined by the method of Bradford (1976) using bovine serum albumin as a standard. The membranes may be used immediately or frozen for later use.

Generation of Baculovirus

The coding region of DNA encoding the human receptor disclosed herein may be subcloned into pBlueBacIII into existing restriction sites or sites engineered into sequences 5' and 3' to the coding region of the polypeptides. To generate baculovirus, 0.5 µg of viral DNA (BaculoGold) and 3 µg of DNA construct encoding a polypeptide may be co-transfected into 2×10$^6$ Spodoptera frugiperda insect Sf9 cells by the calcium phosphate co-precipitation method, as outlined by Pharmingen (in "Baculovirus Expression Vector System: Procedures and Methods Manual"). The cells then are incubated for 5 days at 27° C.

The supernatant of the co-transfection plate may be collected by centrifugation and the recombinant virus plaque purified. The procedure to infect cells with virus, to prepare stocks of virus and to titer the virus stocks are as described in Pharmingen's manual.

Radiolabeled Ligand Binding Assays

Cells expressing the receptors of this invention may be used to screen for ligands for said receptors, for example, by [$^{125}$I]rat NMU-23 and [$^{125}$I]NMU-8 binding assays. The same assays may be used to identify agonists or antagonists of the receptor that may be employed for a variety of therapeutic purposes.

Radioligand binding assays were performed by diluting membranes prepared from cells expressing the receptor in 50 mM Tris buffer (pH=7.4 at 0° C.) containing 0.1% bovine serum albumin (Sigma), aprotinin (0.005 mg/ml, Boehringer Mannheim) and bestatin (0.1 mM, Sigma) as protease inhibitors. The final protein concentration in the assay was 12–40 µg/ml. Membranes were then incubated with either [$^{125}$I]rat NMU-23 or [$^{125}$I]NMU-8 (NEN, specific activity 2200 Ci/mmole) in the presence or absence of competing ligands on ice for 60 min in a total volume of 250 µl in 96 well microtiter plates. The bound ligand was separated from free by filtration through GF/B filters presoaked in 0.5% polyethyleneimine (PEI), using a Tomtec (Wallac) vacuum filtration device. After addition of Ready Safe (Beckman) scintillation fluid, bound radioactivity was quantitated using a Trilux (Wallac) scintillation counter (approximately 40% counting efficiency of bound counts). Data was fit to non-linear curves using GraphPad Prism.

In this manner, agonist or antagonist compounds that bind to the receptor may be identified as they inhibit the binding of the labeled ligand to the membrane protein of cells expressing the said receptor. Non-specific binding was defined as the amount of radioactivity remaining after incubation of membrane protein in the presence of 100 nM of the unlabeled peptide corresponding to the radioligand used. In equilibrium saturation binding assays membrane preparations or intact cells transfected with the receptor are incubated in the presence of increasing concentrations of the labeled compound to determine the binding affinity of the labeled ligand. The binding affinities of unlabeled compounds may be determined in equilibrium competition binding assays, using a fixed concentration of labeled compound (0.05–0.1 nM for [$^{125}$I]rat NMU-23) in the presence of varying concentrations of the displacing ligands.

Localization of mRNA Coding for Human SNORF62 and Human SNORF72.

Quantitative PCR Using a Fluorogenic Probe with Real Time Detection

Quantitative PCR using fluorogenic probes used to characterize the distribution of SNORF62 and SNORF72 RNA. This assay utilizes two oligonucleotides for conventional PCR amplification and a third specific oligonucleotide probe that is labeled with a reporter at the 5' end and a quencher at the 3' end of the oligonucleotide. In the instant invention, FAM (6-carboxyfluorescein) was used as the reporter, and TAMRA (6-carboxy-4,7,2,7'-tetramethyl-rhodamine) was the quencher. As amplification progresses, the labeled oligonucleotide probe hybridizes to the gene sequence between the two oligonucleotides used for amplification. The nuclease activity of Taq thermostable DNA polymerase is utilized to cleave the labeled probe. This separates the quencher from the reporter and generates a fluorescent signal that is directly proportional to the amount of amplicon generated. This labeled probe confers a high degree of specificity. Non-specific amplification is not detected as the labeled probe does not hybridize and as a consequence is not cleaved. All experiments were conducted in a PE7700 Sequence Detection System (Perkin Elmer, Foster City Calif.).

Quantitative RT-PCR

Quantitative RT-PCR was used for the detection of SNORF62 and SNORF72 RNA. For use as a template in quantitative PCR reactions, cDNA was synthesized by reverse transcription from total human RNA. Reverse transcription by SuperScriptII RNAse H⁻ (GibcoBRL/life Technologies) was primed using random hexamers. Parallel reactions included $^{32}$P labeled dCTP to allow quantification of the cDNA.

Following reverse transcription, cDNA was phenol/chloroform extracted and precipitated. Incorporation of 32P dCTP was assessed after precipitation with trichloroacetic acid and the amount of cDNA synthesized was calculated.

For PCR reactions primers with the following oligonucleotide sequences were used:

Human SNORF62:
Forward primer
snorf62h.txt-115F
5'-CAATGGCAGTGCGGCC-3' (SEQ ID NO: 18)
Reverse primer
snorf62h.txt-239R
5'-GGTATGTGGCACAGATGGGC-3' (SEQ ID NO: 19)
Fluorogenic oligonucleotide probe:
snorf62h.txt-138T
5'(6-FAM)- ACTTTGACCCTGAGGACTTGAACCT-GACTG-(TAMRA)3' (SEQ ID NO: 20)

Human SNORF72:
Forward primer:
snorf 72h.txt-179F
5'-CCTCGGCGCAGCCAC-3' (SEQ ID NO: 21)
Reverse primer
snorf 72h.txt-275R
5'-GAATCACCAGGCACACCAGG-3' (SEQ ID NO: 22)
Fluorogenic oligonucleotide probe:
snorf 72h.txt-203T
5'(6-FAM)-CCCGTGTCTGTGGTGTATGTGCCAAT-(TAMRA)3' (SEQ ID NO: 23)

Using these primer pairs, amplicon length is 124 bp for SNORF62, and 96 bp for SNORF72. Each PCR reaction contained 3.0 ng cDNA. Oligonucleotide concentrations were: 500 nM of forward and reverse primers, and 200 nM of fluorogenic probe. PCR reactions were carried out in 50 µl volumes using TaqMan universal PCR master mix (PE Applied Biosystems). Buffer for RT-PCR reactions contained a fluor used as a passive reference (ROX: Perkin Elmer proprietary passive reference I). All reagents for PCR (except cDNA and oligonucleotide primers) were obtained from Perkin Elmer (Foster City, Calif.). Reactions were carried in a PE7700 sequence detection system (PE Applied Biosystems) using the following thermal cycler profile: 50° C. 2 min., 95° C. 10 min., followed by 40 cycles of: 95° C., 15 sec., 60° C. 1 min.

Positive controls for PCR reactions consisted of amplification of the target sequence from a plasmid construct when available. Standard curves for quantitation of human SNORF62 and SNORF72 were constructed using genomic DNA. Negative controls consisted of mRNA blanks, as well as primer and mRNA blanks. To confirm that the mRNA was not contaminated with genomic DNA, PCR reactions were carried out without reverse transcription using Taq DNA polymerase. Integrity of RNA was assessed by amplification of RNA coding for cyclophilin or glyceraldehyde 3-phosphate dehydrogenase (GAPDH). Following reverse transcription and PCR amplification, data was analyzed using Perkin Elmer sequence detection software. The fluorescent signal from each well was normalized using an internal passive reference, and data was fitted a standard curve to obtain relative quantities of SNORF62 and SNORF72 expression.

Chromosomal Localization of Human SNORF62 and SNORF72 Receptor Genes

Chromosomal localization for human SNORF62 and SNORF72 receptor genes was established using a panel of radiation hybrids prepared by the Stanford Human Genome Center (SHGC) and distributed by Research Genetics, Inc. The Stanford G3 panel of 83 radiation hybrids was analyzed by PCR using the same primers, probes and thermal cycler profiles as used for localization. 20 ng of DNA was used in each PCR reaction. Data was submitted to the RH Server (SHGC) which linked the SNORF62 and SNORF72 gene sequences to specific markers. NCBI LocusLink and NCBI GeneMap '99 were used to further analyze the data.

RT-PCR

For the detection of RNA encoding rat SNORF72, RT-PCR was carried out on mRNA extracted from tissue. Reverse transcription and PCR reactions were carried out in a 50 µl volumes using rTth DNA polymerase (Perkin Elmer). Primers with the following sequences were used:

rat SNORF72:
Forward primer:
snorf72rseq.txt-392F
5'-GCCTGTGGGATGCTACTTCAAG-3' (SEQ ID NO: 44)
Reverse primer
snorf72rseq.txt-471R
5'-CGCTAACCGTGGTGACACTG-3' (SEQ ID NO: 45)
Fluorogenic oligonucleotide probe:
snorf72rseq.txt-422T
5' (6-FAM)-CTTCGAGACTGTGTGCTTTGCCTC-CATTC— (TAMRA) 3' (SEQ ID NO: 46)

Using these primer pairs, amplicon length is 79 bp for rat SNORF72. Each RT-PCR reaction contained 100 ng total RNA. Oligonuceotide concentrations were: 500 nM of forward and reverse primers, and 200 nM of fluorogenic probe. Concentrations of reagents in each reaction were: 300 µM each of dGTP; dATP; dCTP; 600 µM UTP; 3.0 mM Mn(OAc)2; 50 mM Bicine; 115 mM potassium acetate, 8% glycerol, 5 units rTth DNA polymerase, and 0.5 units of uracil N-glycosylase. Buffer for RT-PCR reactions also contained a fluor used as a passive reference (ROX: Perkin Elmer proprietary passive reference I). All reagents for RT-PCR (except mRNA and oligonucleotide primers) were obtained from Perkin Elmer (Foster City, Calif.) Reactions were carried using the following thermal cycler profile: 50° C. 2 min., 60° C. 30 min., 95° C. 5 min., followed by 40 cycles of: 94° C., 20 sec., 62° C. 1 min.

Standard curves for quantitation of rat SNORF72 were constructed using genomic DNA. Negative controls consisted of mRNA blanks. To confirm that the mRNA was not contaminated with genomic DNA, PCR reactions were carried out without reverse transcription using Taq polymerase. Integrity of RNA was assessed by amplification of mRNA coding for cyclophilin or glyceraldehyde 3-phosphate dehydrogenase (GAPDH). Following reverse transcription and PCR amplification, data was analyzed using Perkin Elmer sequence detection software. The fluorescent signal from each well was normalized using an internal passive reference, and data was fitted to a standard curve to obtain relative quantities of SNORF72 RNA expression.

Results and Discussion

Isolation of a Full-Length Human SNORF62 Receptor

A search of the SwissPlus database with a search set of known GPCRs yielded several orphan GPCR sequences. One sequence, O43664, was found to be most similar to the neurotensin receptor 1 (31% identity), as well as the recently identified motilin receptor, GPR38 (33% identity). O43664 was then chosen to be cloned for use in ligand-identification screens. In the process of verifying the 5' and 3' ends of the coding sequence for O43664 by RACE, an additional methionine was found upstream from the initiating methionine of O43664, which was in-frame with the rest of the sequence. This new receptor sequence would be 69 bp longer, potentially coding for a protein 23 amino acids longer than O43664. This new sequence was named SNORF62, and is represented in FIGS. 1A–1B and FIGS. 2A–2B. The SNORF62 cDNA codes for a protein of 426 amino acids (FIGS. 2A–2B). There are three potential N-linked glycosylation sites in the extracellular N-terminal domain at amino acid positions 7, 27, and 41. The C-terminal tail contains two potential casein kinase II phosphorylation sites at threonines 366 and 397, and one potential protein kinase C phosphorylation site at serine 360.

Isolation of the rat SNORF62a and rat SNORF62b receptors A fragment of the rat homologue of SNORF62 was amplified from rat genomic DNA and rat testes cDNA by low stringency PCR using oligonucleotide primers designed against the mouse SNORF62 (GenEMBL Accession Number AF044602). This fragment contains 667 nucleotides of rat SNORF62, from the end of TM1 to the beginning of TM6.

To obtain the full-length rat SNORF62, 5' RACE was performed on rat spleen and rat testes, and 3' RACE was performed on rat spleen. The 5' RACE reaction yielded 400 and 800 bp bands that contained sequence information through the first transmembrane domain to the amino terminus, but had no putative in-frame initiating methionine-coding sequence. A second 5' RACE reaction yielded 300 bp band from rat testes cDNA that contained sequence information through the first transmembrane domain and a putative in-frame initiating methionine-coding sequence. Another band of 700 bp from rat spleen cDNA yielded a different sequence containing sequence information through the first transmembrane domain and a putative in-frame initiating methionine-coding sequence. The 3' RACE reaction yielded a 1000 bp band that contained sequence for an in-frame stop codon downstream from the region coding for the seventh transmembrane domain.

Two full-length receptor sequences were identified and named SNORF62a (from rat testes) and SNORF62b (from rat spleen). These sequences are identical except for the first two amino acids of SNORF62a and the first 28 amino acids of SNORF62b. The largest open reading frame is 1239 and 1317 nucleotides (FIGS. 17A–B and 19A–B), and predicts a protein of 413 and 439 amino acids (FIGS. 18A–B and 20A–B) for rat SNORF62a and rat SNORF62b, respectively. A comparison of the rat SNORF62a and rat SNORF62b sequences with the human SNORF62 sequence reveals 76.5% and 75% nucleotide identities and 71% and 69.5% amino acid identities, respectively. An amino acid alignment of the sequences of SNORF62 is shown in FIGS. 21A–21C.

Hydrophobicity (Kyte-Doolittle) analysis of the amino acid sequence of the full length clones indicates the presence of seven hydrophobic regions, which is consistent with the seven transmembrane domains of a G protein coupled receptor (FIGS. 18A–B and 20A–B).

Isolation of a Full-Length Human SNORF72 Receptor

A receptor sequence that was 46% identical to SNORF62 was found in the public domain, and subsequently named SNORF72. After cloning the full-length receptor from human whole-brain cDNA by PCR, the actual sequence of SNORF72 was found to be slightly different from the published clone. Five nucleotide differences were discovered between this new SNORF72 sequence and the corresponding published sequence, four of which changed the amino acid sequence of the receptor. The new clone in the pEXJ.T3T7 expression vector was named pEXJ.T3T7-hS-NORF72-f. The nucleotide sequence of SNORF72 is shown in FIGS. 3A–3B, and the predicted amino acid sequence of the receptor encoded by SNORF72 is shown in FIGS. 4A–4B. A GAP comparison of the amino acid sequences (Wisconsin Package version 10.0, Genetics Computer Group, Madison, Wis.) of SNORF72 with SNORF62 indicates that there is a 47% amino acid identity between the two receptors (FIG. 5), suggesting that they are likely to be members of the same receptor subfamily.

Isolation of a Full-Length Rat SNORF72 Receptor

Sequencing of the cDNA insert shows a long open reading frame containing the full 1185 base pair coding region, corresponding to a predicted protein of 395 amino acids. Hydrophobicity analysis reveals the seven predicted transmembrane domains typical of G protein-coupled receptors. Sequence comparison with the predicted human SNORF72 coding region reveals 81% identity at the nucleotide level and 79% identity at the amino acid level. The rat SNORF72 N-terminus has a 5 amino acid deletion compared with human SNORF72 and contains an additional downstream methionine not present in human SNORF72 (FIGS. 16A–16B). Conversely, the human SNORF72 N-terminus contains an additional upstream methionine (FIGS. 16A–16B) not found in rat SNORF72. The C-terminus of rat SNORF72 also differs from human SNORF72 in that it is shorter by 12 amino acids (FIGS. 16A–16B). Rat and human SNORF72 were also compared with human SNORF62 (FIGS. 16A–16B). Rat and human SNORF72 show 47–49% amino acid identity with human SNORF62, a typical level of homology for receptor subtypes activated by the same ligand. This construct of rat SNORF72 was named pEXJ.BS-rSNORF72-f.

Increase in Intracellular $Ca^{2+}$ Release

Figure 6:
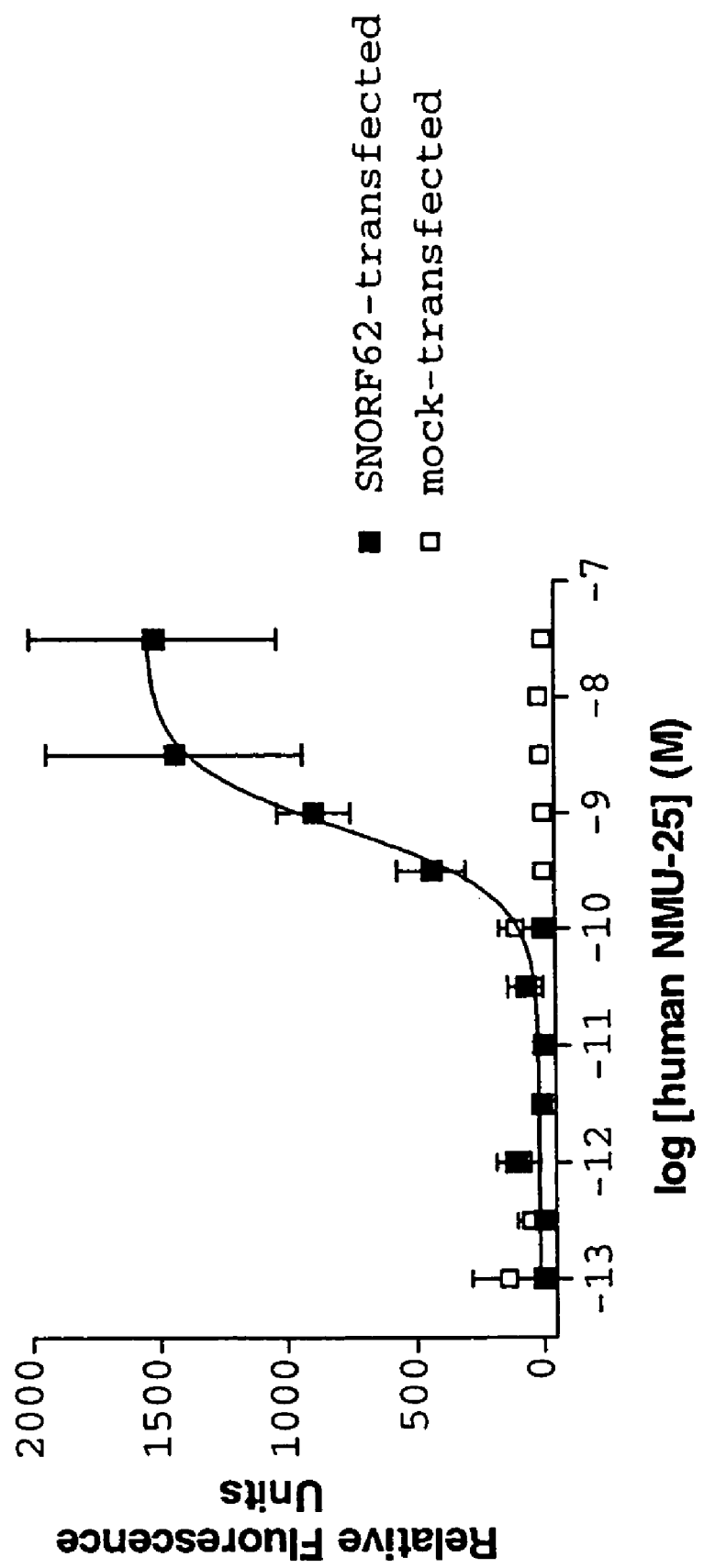
Figure 7:
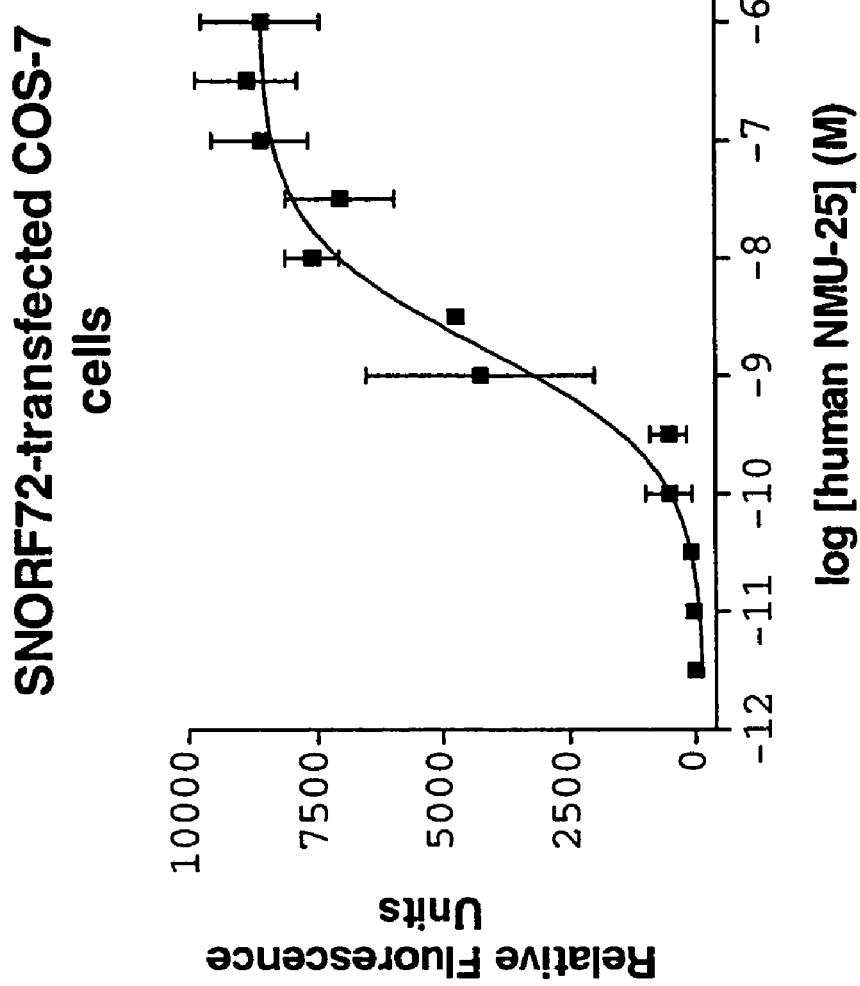

COS-7 cells were transiently transfected with SNORF62, SNORF72 or vector DNA (mock) as described in Materials and Methods. Application of human NMU-25 resulted in concentration-dependent release of intracellular $Ca^{2+}$ (as measured by FLIPR™) in COS-7 cells transfected with SNORF62 or SNORF72 (FIGS. 6 and 7). In contrast, human NMU-25 had no significant effect on intracellular $Ca^{2+}$ release in vector-transfected cells (FIG. 6). The EC50 values obtained for the stimulation of SNORF62 and SNORF72 by NMU and related peptides are listed in Table 1 and Table 1A.

Figure 8:
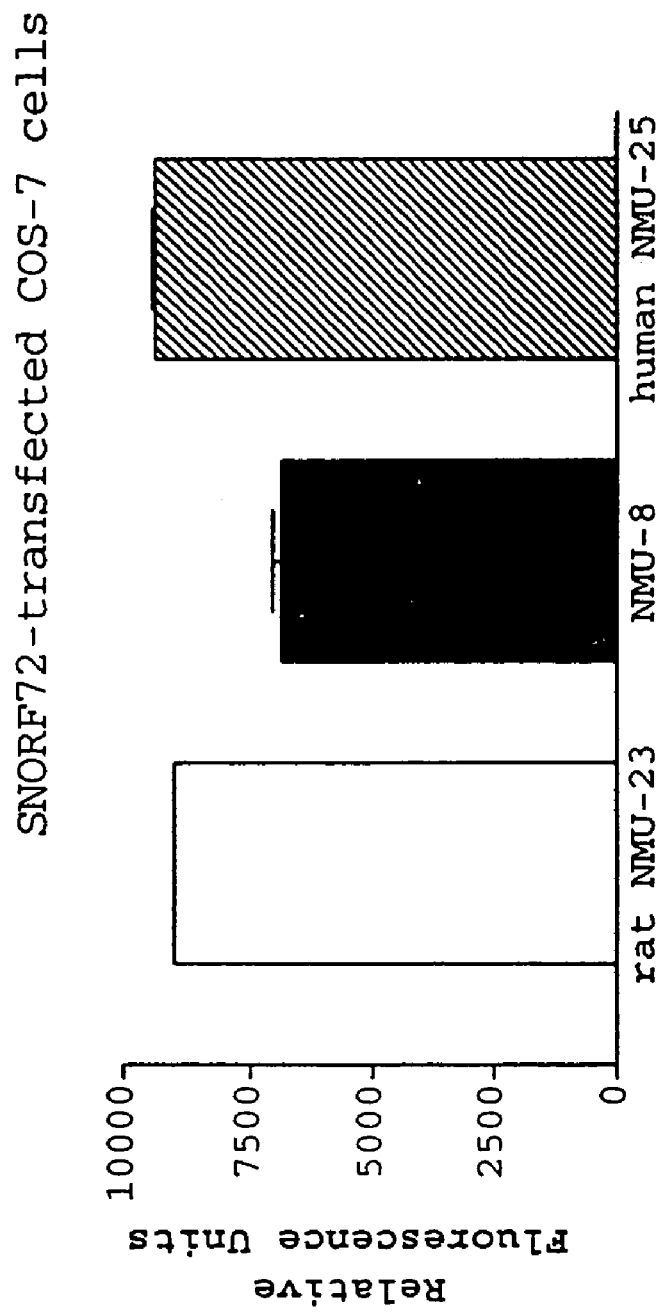

SNORF72-transfected COS-7 cells were also stimulated by rat NMU-23, NMU-8 and human NMU-25 (FIG. 8). All of the peptides that activated SNORF62 and SNORF72 produced similar maximum responses and were therefore full agonists (data not shown).

The high potency of NMU-induced stimulation of SNORF62 and SNORF72 provides support for classifying these receptors as NMU receptors. For comparison, in isolated rat uterus preparations the EC50 concentration for contraction by rat NMU-23 is 0.2 nM (Domin et al. 1989). The slightly lower potency of rat NMU-23 observed in the SNORF62— and SNORF72— transfected COS-7 cells (average EC50=2.1 nM for SNORF62 and 1.7, 5.1 nM; n=2, for SNORF72) may be due to species differences in the peptides and/or receptors as well as the artificial cell hosts.

Figure 22:
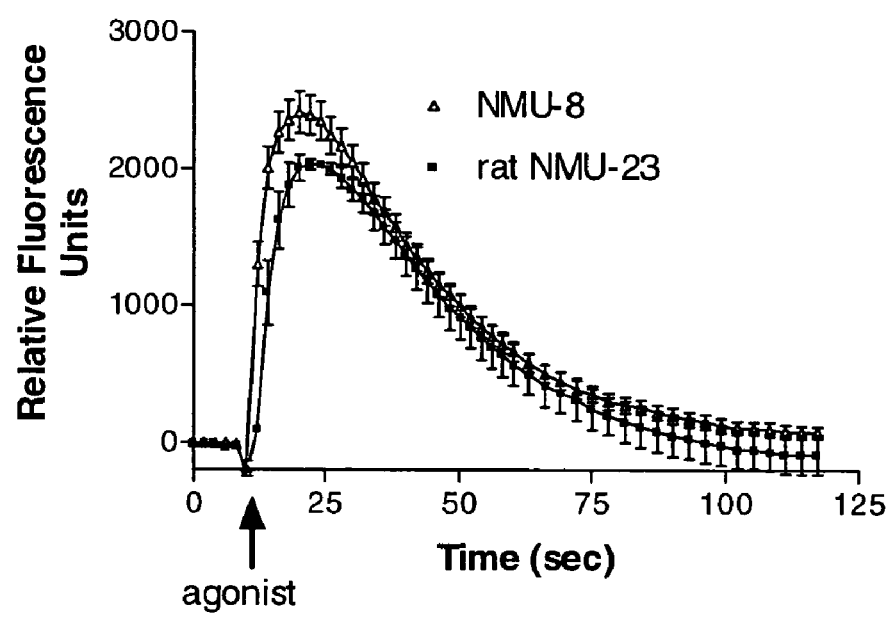

NMU-8 and rat NMU-23 produced robust increases in intracellular $Ca^{2+}$ (as measured by FLIPR™) in COS-7 cells transiently transfected with rat SNORF72 (FIG. 22). The responses were dose dependent reaching maximal stimulation at concentrations below 100 nM. Thus, rat SNORF72 is a functional receptor for NMU.

TABLE 1

Potency of NMU and related peptides for stimulation of $Ca^{++}$ release in SNORF62-transfected COS-7 cells.

| peptide | AVG EC50 (nM) | n | sem |
|---|---|---|---|
| human NMU-25 | 4.0 | 7 | 1.3 |
| porcine NMU-25 | 5.2 | 4 | 0.8 |
| rat NMU-23 | 2.1 | 3 | 0.5 |
| porcine NMU-8 | 1.1 | 4 | 0.4 |

TABLE 1A

Potency of NMU and related peptides for stimulation of $Ca^{2+}$ release and binding affinities were determined in SNORF62 and SNORF72-transfected COS-7 cells (n = 2–7). "N.D." = not determined.

|  | SNORF62 | | SNORF72 | |
|---|---|---|---|---|
|  | Avg EC50 (nM) | Avg Ki (nM) | Avg EC50 (nM) | Avg Ki (nM) |
| human NMU-25 | 4.0 ± 1.3 | 2.0 ± 0.4 | 2.4 ± 0.6 | 3.0 ± 0 |
| porcine NMU-25 | 5.2 ± 0.8 | 1.1 ± 0.2 | 3.0 ± 0.7 | 1.8 ± 0.6 |
| rat NMU-23 | 2.1 ± 0.5 | 0.5 ± 0.2 | 5.0 ± 1.7 | 0.5 ± 0.6 |
| porcine NMU-8 | 1.1 ± 0.4 | 3.0 ± 1.3 | 1.2 ± 0.3 | 1.2 ± 0.3 |
| frog PP* | N.D. | >10 μM | N.D. | >10 μM |
| rat PP | N.D. | >10 μM | N.D. | >10 μM |
| VIP+ | N.D. | >10 μM | N.D. | >10 μM |

*pancreatic polypeptide
+vasoactive intestinal peptide

Radioligand Binding

Receptor binding was performed on SNORF62-, SNORF72- and mock-transfected COS-7 membranes using $[^{125}I]$rat NMU-23 and $[^{125}I]$NMU-8 as radioligands as described in the Methods.

Binding of $[^{125}I]$rat NMU-23 and $[^{125}I]$NMU-8 to the SNORF62 and SNORF72 membranes was time dependent (reaching equilibrium by 30 min, data not shown) and saturable (FIGS. 9A–9B and 11A–11B). No saturable, specific binding sites for either radioligand were present in the mock-transfected COS-7 cell membranes (data not shown).

In membranes from SNORF62-transfected COS-7 cells $[^{125}I]$rat NMU-23 and $[^{125}I]$NMU-8 bound with high affinity (Kd=0.61, 0.72 nM and Kd=1.2, 2.8 nM, respectively; n=2). See FIGS. 9A and 9B, respectively. $[^{125}I]$NMU-8 identified 3-fold fewer sites than did $[^{125}I]$rat NMU-23 (Bmax=3.8, 3.4 pmol/mg protein and Bmax=16.5, 9.9 pmol/mg protein, respectively; n=2) even though NMU-8 and rat NMU-23 are both full agonists in the functional assay (data not shown). This may be due to technical limitations in reaching high enough concentrations of $[^{125}I]$NMU-8 to fully saturate the binding sites, since it demonstrates somewhat lower affinity than $[^{125}I]$rat NMU-23 (See Table 1). Non-specific binding represented approximately 6% and 30% of total binding for $[^{125}I]$rat NMU-23 and $[^{125}I]$NMU-8, respectively.

In SNORF72-transfected COS-7 membranes, Kd values determined from saturation binding were 0.81, 0.96 nM (n=2) for $[^{125}I]$rat NMU-23 and Kd=0.83, 0.82 (n=2) for $[^{125}I]$NMU-8. See FIGS. 11A and 11B, respectively. Non-specific binding represented approximately 15% and approximately 35% of total binding for $[^{125}I]$rat NMU-23 and $[^{125}I]$NMU-8, respectively. Both radioligands identified similar numbers of sites in SNORF72-transfected membranes (Bmax=8.0, 8.2 pmol/mg protein for $[^{125}I]$rat NMU-23 and Bmax=6.9, 5.5 pmol/mg protein for $[^{125}I]$NMU-8; n=2). Interestingly, although the maximum $Ca^{2+}$ signal generated by human NMU-25 was higher in SNORF72-transfected cells than in SNORF62-transfected cells (FIGS. 7 and 8 vs FIG. 6), the levels of receptor expression were similar (based on Bmax values discussed above). This observation suggests more efficient coupling of SNORF72 to $Ca^{2+}$ releasing signal transduction mechanisms in the COS-7 cells.

Figure 10:
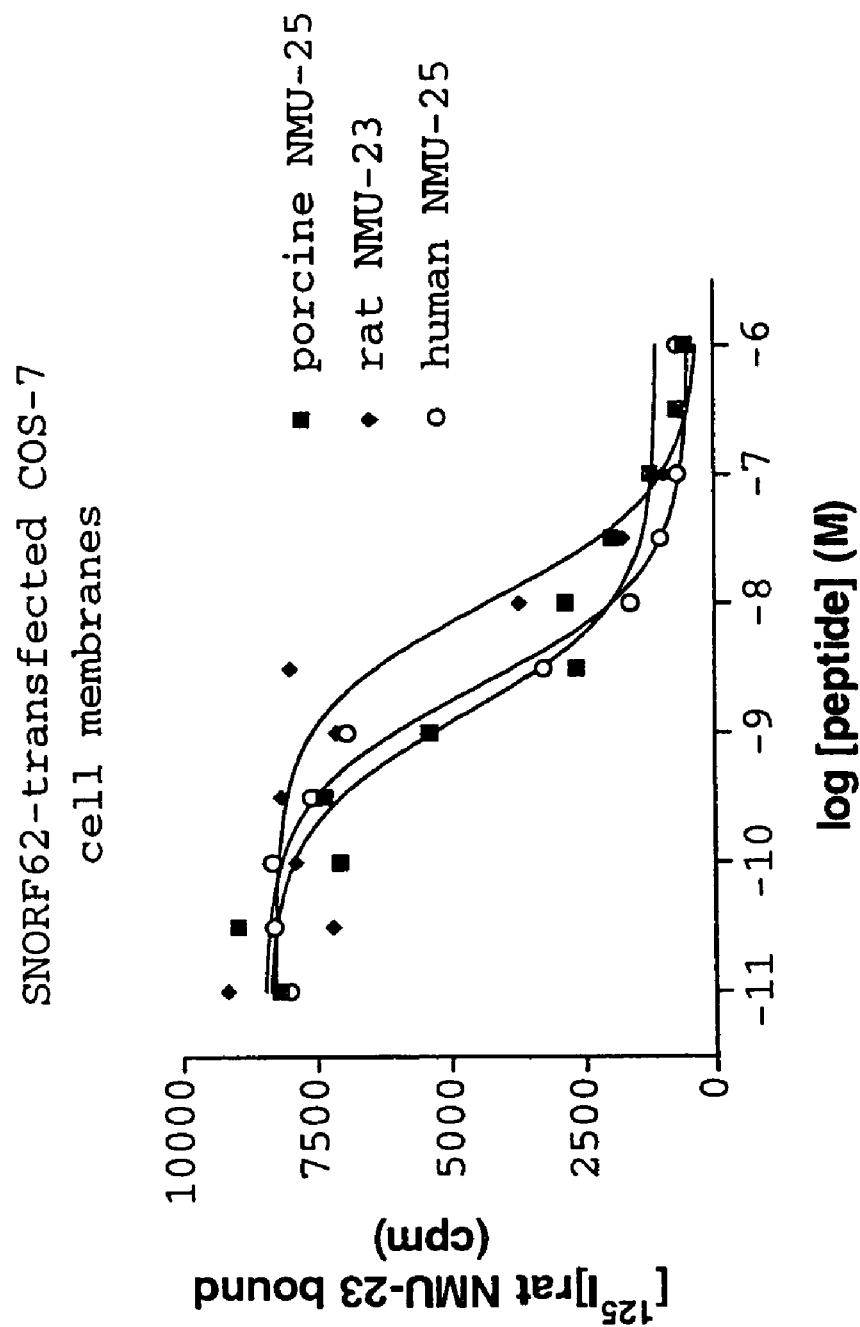
Figure 12:
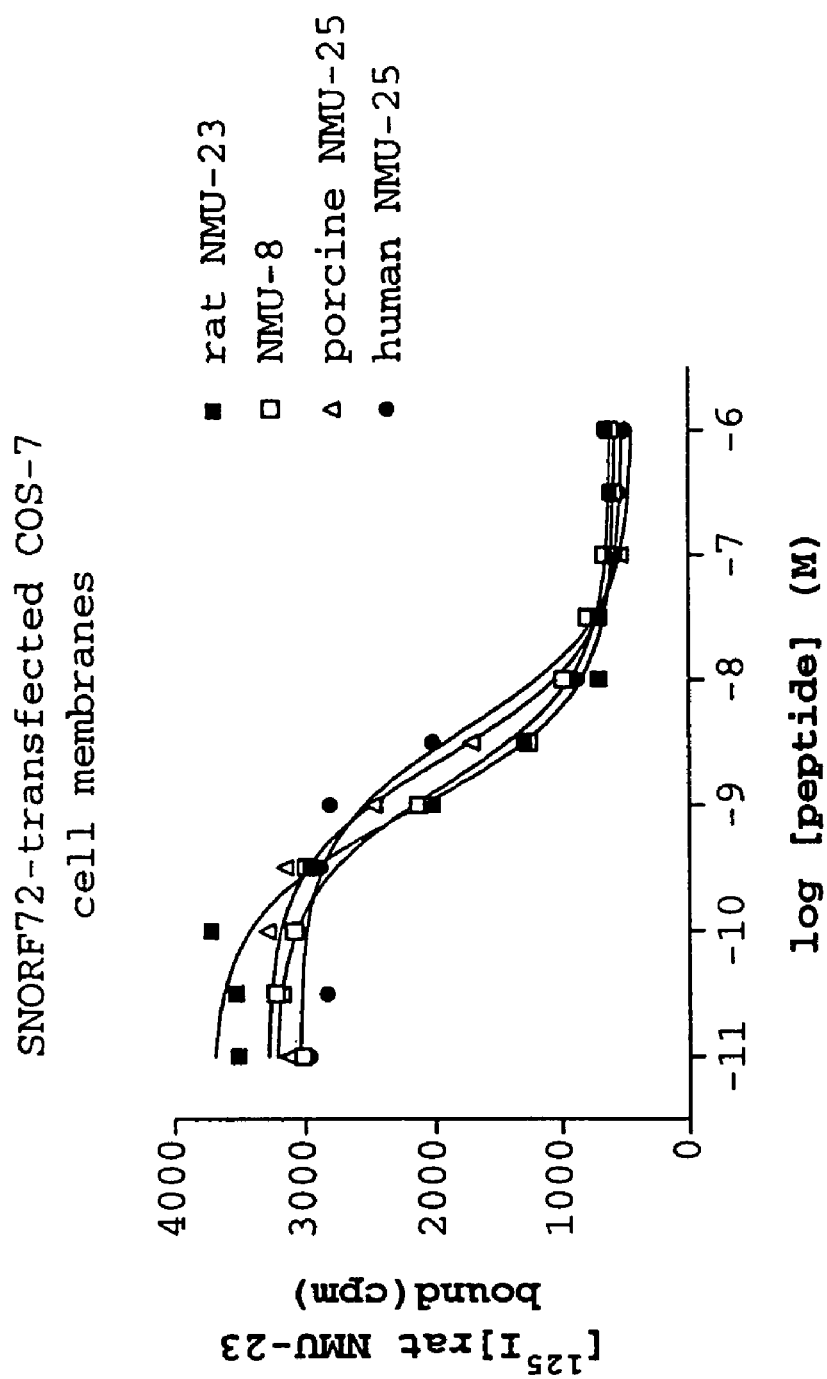

Displacement of $[^{125}I]$rat NMU-23 binding allowed the estimation of binding affinity of a number of peptides (FIGS. 10, 12 and Table 2). The binding affinity of rat NMU-23 (average pKi=9.4) in SNORF62 membranes was somewhat greater than NMU-8 (average pKi=8.5), consistent with the binding affinities determined for the radioiodinated peptides. However, in SNORF72 membranes the apparent binding affinities of rat NMU-23 and NMU-8 were similar (average pKi=9.0 and 8.9, respectively).

The high affinity binding of $[^{125}I]$rat NMU-23 at SNORF62 and SNORF72 in COS-7 cell membranes is similar to the Kd determined for this radioligand in isolated rat uterus (Kd=0.35 nM, Nandha et al. 1993). This affinity corresponds to the EC50 of contractile activity in this tissue, 0.2 nM, similar to the involvement of the binding site in NMU-induced uterine contraction. The binding site in this tissue demonstrated lower affinity for NMU-8 than for rat NMU-23 with average IC50 values of 60 nM and 1 nM, respectively.

Although rat PP, frog PP and vasoactive intestinal peptide (VIP) share minor homology with NMU (see Background), these peptides did not displace binding of $[^{125}I]$rat NMU-23 bound in either SNORF62 or SNORF72 membranes (Table 2) or activate the receptors in transfected COS-7 cells (data not shown).

TABLE 2

Binding pKi values determined from displacement of [$^{125}$I] rat NMU-23 (0.05–0.1 nM) binding in membranes prepared from SNORF62- or SNORF72- transfected COS-7 cells. n = 2, N.D. = not determined.

| Compound | SNORF62 | | SNORF72 | |
| --- | --- | --- | --- | --- |
| | Avg pKi | STDev pKi | Avg pKi | STDev pKi |
| human NMU-25 | 8.7 | 0.1 | 8.5 | 0.1 |
| porcine NMU-25 | 9.0 | 0.1 | 8.7 | 0.1 |
| rat NMU-23 | 9.4 | 0.2 | 9.0 | 0.6 |
| NMU-8 | 8.5 | 0.2 | 8.9 | 0.1 |
| frog PP | <5 | <5 | <5 | <5 |
| rat PP | <5 | <5 | <5 | <5 |
| VIP | <5 | <5 | <5 | <5 |

Inositol Phosphate (IP) Release

Figure 23:
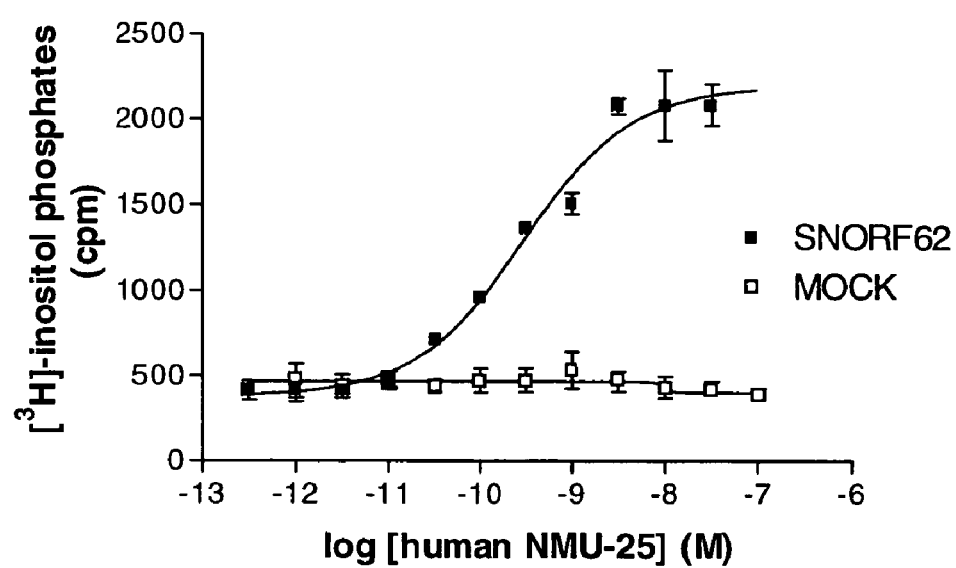

Exposure of SNORF62-transfected COS-7 cells (but not mock-transfected cells) to human NMU-25 caused the dose-dependent release of IP second messengers (approximately 2-fold above basal) with an EC50 of 0.25±0.09 nM (FIG. 23). Rat NMU-23 and porcine NMU-8 were also full agonists in this assay with an EC50=0.23±0.10 nM and 0.23±0.06 nM, respectively (n=3). The EC50 values measured for IP release are lower than the EC50 values measured for increases in intracellular $Ca^{2+}$ (see Table 1 and Table 1A). This may be due to differences in experimental conditions between the two types of assays including the non-equilibrium nature of $Ca^{2+}$ measurements.

In addition, the $Ca^{2+}$ release response to human NMU-25 was present in SNORF62-transfected cells following pre-treatment with pertussis toxin (100 ng/ml for 18–20 hours, n=2) indicating that the $Ca^{2+}$ signal is not predominantly generated by G-proteins of the Gi/Go family (data not shown). Taken together these results indicate that SNORF62 couples to phospholipase C stimulation via a Gq-type G-protein in COS-7 cells.

Figure 13:
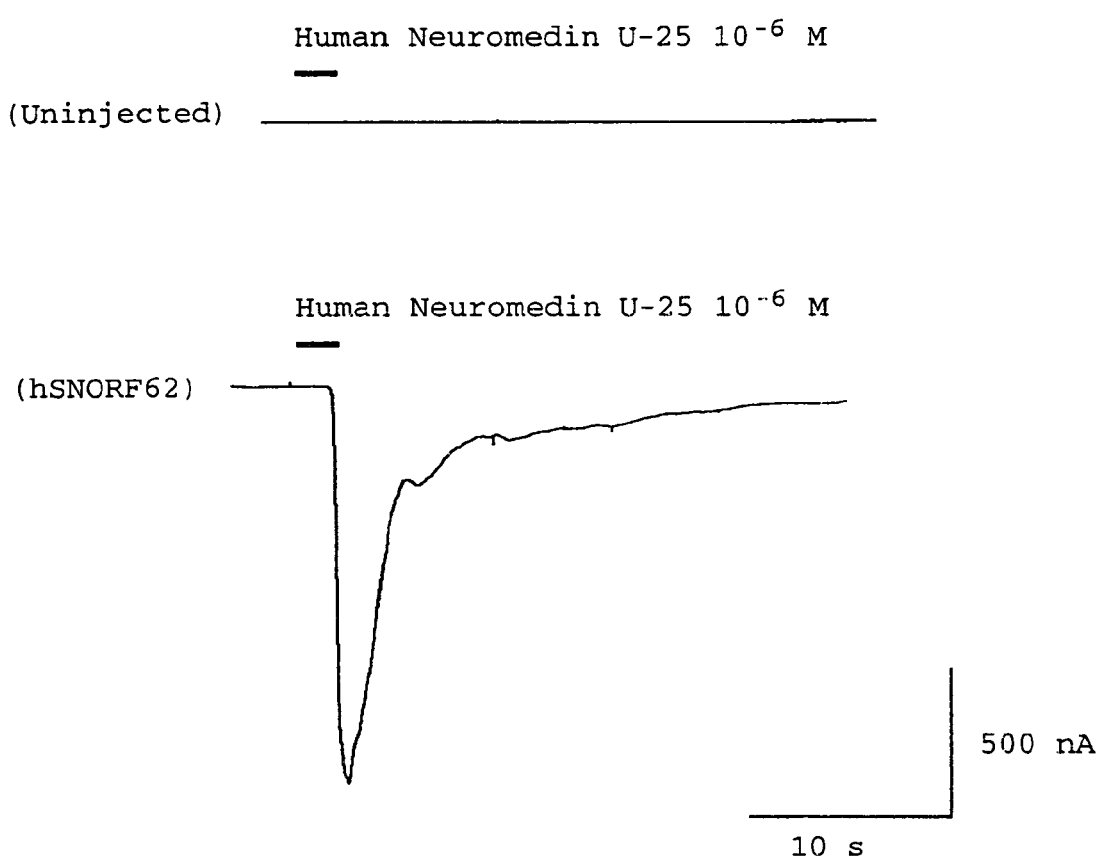

Activation of Calcium-Activated Cl$^-$ Currents in Human SNORF62-Expressing *Xenopus* Oocytes In *Xenopus laevis* oocytes injected with SNORF62 mRNA human NMU-25 elicited oscillatory Cl$^-$ currents through G protein-coupled stimulation of the phosphoinositide/$Ca^{2+}$ second messenger system, which in turn leads to the activation of a $Ca^{2+}$-dependent Cl$^-$ current. As shown in FIG. 13, control oocytes, lacking injection of foreign mRNA, typically showed no response to human NMU-25 (n=5). However, in oocytes injected with SNORF62 mRNA, the current amplitude averaged 1065±211 nA (n=3) in response to 1 µM human NMU-25. Porcine NMU-25 (1 µM) also elicited a strong response (2150±330 nA (n=3)) from oocytes injected with SNORF62 mRNA, but not in control oocytes (data not shown).

Detection of RNA Coding for Human SNORF62

RNA was isolated from multiple tissues (listed in Table 3) and assayed as described. Quantitative RT-PCR using a fluorgenic probe demonstrated RNA encoding human SNORF62 to be localized in highest abundance in peripheral organs, particularly in elements of the urogenital and gastrointestinal systems.

The highest levels are found in the testes. The uterus, prostate and kidney (both cortex and medulla) express SNORF62 RNA. This is consistent with functional studies and localization of NMU that are found in uterus and prostate (see Background). However, NMU has not been localized to the kidney and its function there is not known. However, the presence in the kidney may be associated with NMU's efffects at increasing arterial blood pressure (in rats, Minamino et al., 1985b).

The gastrointestinal system also has considerable amounts of SNORF62 RNA. The stomach, small intestine (pooled) as well as the duodenum express SNORF62 RNA. This is consistent with the high levels of NMU in the GI tract found by radioimmuunoassay (RIA) (Domin et al. 1987) in both myenteric and submucosal plexuses of the gut (Ballesta et al. 1988) and the postulated role of NMU as a potent constrictor of smooth muscle. SNORF62 RNA is also present in the pancreas at levels equivalent to that seen in other regions of the GI tract, but the role of the receptor in this tissue in not clear. It is not known if the SNORF62 receptors are found on the pancreatic islets, acinar cells or are present on vasculature within the gland. Sumi et al. (1987) demonstrated an increase in blood flow in the pancreas after adminstration of NMU suggesting a vascular localization or function.

Other tissues expressing SNORF62 RNA include the lung, trachea, adrenal gland, and mammary gland, with lower levels in skeletal muscle, and heart. This broad distribution implies a broad regulatory or modulatory activity, perhaps at the level of smooth muscle contraction or secretagogue actions within these tissues. As discussed in the Background, NMU directly affects cells of the adrenal gland to alter secretion and may therefore act as a secretagogue in other tissues as well.

CNS structures express SNORF62 RNA but at levels much lower than those seen in peripheral organs. Within the CNS, SNORF62 RNA has been detected in highest abundance in the cerebellum, dorsal root ganglia, hippocampus and spinal cord. NMU-like immunoreactivity was identified in each of these regions (Domin et al. 1987). Within the CNS, it is found in levels that are 5 to 25-fold less than that found in peripheral organs. The role of SNORF62 RNA in the CNS is not clear, however its broad distribution is consistent with the broad distribution of NMU found in the brain (Domin et al. 1987). The presence of NMU as well as SNORF62 RNA in the spinal cord, dorsal root ganglia, and medulla oblongata implies a role in sensory transmission or modulation.

In summary, SNORF62 RNA is broadly distributed, with highest concentrations in gastrointestinal and urogenital systems. Levels within the CNS are fairly low. This distribution implies regulation/modulation of multiple systems. Some of the effects of the peripheral actions of SNORF62 may be mediated by the actions of NMU on smooth muscle, and its CNS distribution suggests a role in the modulation of sensory transmission.

Detection of RNA Coding for Human SNORF72

RNA was isolated from multiple tissues (listed in Table 3) and assayed as described. Quantitative RT-PCR using a fluorgenic probe demonstrated RNA encoding human SNORF72 to be localized in highest abundance in the CNS. The CNS regions expressing the highest levels of SNORF72 RNA include the medulla oblongata, pontine reticular formation, spinal cord, and thalamus (Table 3). This distribution is highly suggestive of a role in sensory transmission or modulation and is in sharp contrast to the pattern seen with SNORF62, which has a distribution primarily in peripheral organs. The exception to this CNS/peripheral organ pattern are the testes, which express high levels of both SNORF62 and SNORF72 RNA.

The hippocampus, hypothalamus and cerebral cortex all express moderate-high levels of SNORF72 RNA. Other CNS structures expressing SNORF72 RNA include the amygdala and cerebellum. Dorsal root ganglia also express SNORF72 RNA albeit at substantially lower levels than those found in the spinal cord, but comparable to those found in the amygdala and cerebellum.

The expression pattern of SNORF72 RNA in the CNS is consistent with the hypothesis that its ligand, NMU, is a sensory transmitter/modulator. NMU is found in the spinal cord, dorsal root ganglia, and medulla oblongata using radioimmunoassay (Domin et al. 1987) and immunohistochemistry (Ballesta et al. 1988). Its presence in other regions including hippocampus, hypothalamus and cerebral cortex implies a modulatory role in multiple systems within the CNS.

Peripheral organs expressing SNORF72 RNA include the kidney (medulla), lung and trachea. The function of SNORF72 in the kidney may be different from SNORF62 despite the fact that NMU is possibly an endogenous ligand for both. SNORF62 RNA is found in equivalent amounts in both the cortex and medulla of the kidney. SNORF72 RNA is found primarily in the medulla, suggesting different physiological functions for these two receptors in the kidney. It is not known at this time which cells in the kidney express SNORF62 and/or SNORF72 RNA. The broad distribution in multiple peripheral organs (Table 3) implies a broad regulatory or modulatory activity, perhaps at the level of smooth muscle contraction within these tissues. It is interesting to note that SNORF72 RNA is expressed in low levels in gastrointestinal tract, regions with high levels of SNORF62 RNA and high levels of NMU.

In summary, SNORF72 RNA is expressed in highest abundance in the CNS, particularly in structures associated with sensory transmission/or modulation. This localization suggests a role for SNORF72 in the central actions of NMU whereas the localization of SNORF62 RNA suggest a role for SNORF62 in the peripheral actions of this peptide.

TABLE 3

Summary of distribution of mRNA coding for human SNORF62 and human SNORF72.
Data is expressed as % of the highest expressing tissue.

| Region | snorf62 % of maximum | snorf72 % of maximum | Potential applications |
|---|---|---|---|
| adipose tissue | <1 | not detected | Obesity and metabolic disorders |
| adrenal gland | 31.65 | <1 | Regulation of metabolic steroids, disorders of the adrenal gland, regulation of epinephrine release |
| amygdala | 5.90 | 9.58 | Depression, phobias, anxiety, mood disorders |
| cerebellum | 21.52 | 6.25 | Motor coordination disorders |
| cerebral cortex | 8.42 | 20.28 | Cognition, sensory and motor integration disorders |
| dorsal root ganglia | 14.68 | 9.33 | Sensory transmission disorders, pain |
| duodenum | 26.96 | trace | Gastrointestinal disorders |
| heart | 12.66 | 2.63 | Cardiovascular disorders |
| hippocampus | 13.92 | 43.61 | Cognition/memory disorders |
| hypothalamus | 10.13 | 40.58 | Appetite/obesity, neuroendocrine regulation disorders |
| kidney, cortex | 47.00 | 1.03 | Hypertension, electrolyte balance disorders |
| kidney, medulla | 33.33 | 16.42 | Hypertension, electrolyte balance disorders |
| liver | not detected | not detected | Metabolic disorders |
| lung | 48.86 | 17.08 | Respiratory disorders, asthma |
| mammary gland | 20.25 | 1.46 | Lactation disorders |
| medulla oblongata | 7.27 | 100 | Sensory transmission/integration disorders, pain, cardiovascular disorders, respiratory disorders, |
| pancreas | 45.70 | trace | Endocrine disorders, diabetes, pancreatitis |
| pituitary | 3.44 | <1 | Endocrine/neuroendocrine disorders |
| pontine reticular formation | 3.61 | 92.50 | Sleep disorders, sensory modulation and transmission disorders |
| prostate gland | 27.09 | 1.79 | Benign prostatic hyperplasia and male sexual dysfunction |
| salivary gland | 2.84 | not detected | Digestive disorders |
| skeletal muscle | 13.67 | <1 | Musculoskeletal disorders |
| small intestine | 73.80 | 1.74 | Gastrointestinal disorders |
| spinal cord | 13.16 | 80.00 | Analgesia, sensory modulation and transmission disorders, pain |
| spleen | 1.25 | not detected | Immune disorders |
| stomach | 39.62 | 5.58 | Gastrointestinal disorders |
| testes | 100.00 | 85.00 | Male reproductive disorders, regulation of steroid hormones |
| thalamus | 7.48 | 47.83 | Sensory integration disorders, pain |
| trachea | 27.85 | 8.92 | Respiratory disorders, asthma |
| uterus | 34.43 | 4.20 | Gestational disorders, dysmenorrhea, female sexual dysfunction |

The identificaiton of SNORF62 and SNORF72 as members of the family of NMU receptors is supported by a variety of experimental results. Both receptors are activated by full length NMU (rat, porcine and human) as well as NMU-8. In membranes prepared from SNORF62— or SNORF72-transfected cells, [$^{125}$I]rat NMU-23 and [$^{125}$I] NMU-8 bind with high affinity. Human NMU-25 also demonstrates activation of SNORF62 expressed in Xenopus oocytes. Taken together these results indicate that SNORF62 and SNORF72 are functional NMU receptors. Differential localization of SNORF62 RNA predominantly to the periphery and SNORF72 RNA predominantly to the CNS suggest different roles for these receptors in vivo.

Chromosomal Localization of Human SNORF62 and SNORF72 Receptor Genes

The human SNORF62 gene maps to SHGC-33253 which is localized to chromosome 2q34–q37. SNORF 72 maps to SHGC-8848, which is localized to chromosome 5q31.1-q31.3.

Detection of RNA coding for rat SNORF 72: mRNA was isolated from multiple tissues and assayed as described (See Table 4).

Quantitative RT-PCR using a fluorgenic probe demonstrated mRNA coding for rat SNORF72 to be localized in highest abundance in the ovary and uterus. This is consistent with functional studies and localization of neuromedin U. Neuromedin U has been localized to the uterus (Domin, et al., 1987) and it has been shown to potently contract uterine smooth muscle (Minamino, et al.,. 1985a and 1985b).

The stomach and the duodenum also express SNORF72 RNA. As described previously, this is consistent with the high levels of NMU in the GI tract found by radioimmuunoassay (RIA) (Domin, et al., 1987). SNORF72 RNA is also expressed in substantial amounts in the urinary bladder. Taken together, this localization is consistent with the postulated role of NMU as a potent constrictor of smooth muscle. This distribution contrasts sharply with the distribution of human SNORF72 which is expressed in highest abundance in the CNS.

In the rat CNS highest levels of SNORF72 are expressed in the spinal cord and medulla oblongata. In the human, these also express high levels of SNORF72. The presence of SNORF72 RNA in the medulla and spinal cord is suggestive of a role in sensory transmission of modulation.

The rat hippocampus, hypothalamus and cerebral cortex all express SNORF72. Its presence in multiple, diverse structures implies broad modulatory role in multiple systems within the CNS.

In summary, rat SNORF72 is expressed in the uterus and the ovaries. This receptor may be responsible for modulating uterine contraction by NMU. Within the CNS, it has a broad distribution and may be responsible for modulating many of the central actions of NMU.

TABLE 4

Summary of distribution of mRNA coding for rat SNORF72 receptors
RNA encoding SNORF72r is expressed as % of highest expressing tissue: uterus

| Tissue | qRT-PCR % of max | Potential applications |
|---|---|---|
| adipose | 1.26 | metabolic disorders |
| adrenal cortex | trace | regulation of steroid hormones |
| adrenal medulla | trace | regulation of epinephrine release |
| cerebellum | 0.81 | motor coordination |
| cerebral cortex | 3.39 | Sensory and motor integration, cognition |
| dorsal root ganglia | 2.72 | sensory transmission |
| duodenum | 4.33 | gastrointestinal disorders |
| heart | 0.14 | cardiovascular indications |
| hippocampus | 4.27 | cognition/memory |
| hypothalamus | 13.14 | appetite/obesity, neuroendocrine regulation |
| kidney | 0.07 | electrolyte balance, hypertension |
| liver | 0.08 | diabetes |
| lung | 4.84 | respiratory disorders, asthma |
| medulla oblongata | 5.07 | analgesia, motor coordination |
| ovary | 78.50 | reproductive function |
| pancreas | 1.44 | diabetes, endocrine disorders |
| pituitary | trace | endocrine/neuroendocrine regulation |
| skeletal muscle | 0.28 | musculoskeletal disorders |
| spinal cord | 20.70 | analgesia, sensory modulation and transmission |
| spleen | trace | immune disorders |
| stomach | 3.86 | gastrointestinal disorders |
| testes | 2.64 | reproductive function |
| urinary bladder | 5.96 | urinary incontinence |
| uterus | 100.00 | gestational and reproductive disorders |
| vas deferens | 0.79 | reproductive function |

REFERENCES

Austin, C., et al., "Cloning and characterization of the cDNA encoding the human neuromedin U (NmU) precursor: NmU expression in the human gastrointestinal tract" *J Molecular Endocrinology* 14: 157–169 (1995).

Ballesta J., et al., "Occurence and developmental pattern of neuromedin U-immunoreactive nerves in the gastrointestinal tract and brain of the rat" *Neuroscience* 25: 797–816 (1988).

Benito-Orfila, M. A., et al., "The motor effects of neuromedin U on rat stomach in vitro" *Eur J Pharmacol* 193: 329–333 (1991).

Bradford, M. M., "A rapid and sensitive method for the quantitation of microgram quantities of protein utilizing the principle of protein-dye binding", *Anal. Biochem.* 72: 248–254 (1976).

Brown D. R. and F. L. Quito, "Neuromedin U octapeptide alters ion transport in porcine jejunum" *Eur J Pharmacol* 155:159–162 (1988).

Bush, et al., "Nerve growth factor potentiates bradykinin-induced calcium influx and release in PC12 cells" *J. Neurochem.* 57: 562–574(1991).

Chu, Y. Y., et al., "Characterization of the rat A2a adenosine receptor gene", *DNA Cell Biol.* 15(4): 329–337 (1996).

Cimini V., et al., "Modulation of galanin nad neuromedin U-like immunoreactivity in rat corticotrophes after alteration of endocrine status" *Cell Tissue Res* 272: 137–146 (1993).

Dascal, N., et al., "Atrial G protein-activated K$^+$ channel: expression cloning and molecular properties" *Proc. Natl. Acad. Sci. USA* 90: 10235–10239 (1993).

Domin J., et al., "Neuromedin U—A study of its distribution in the rat" *Peptides* 8:779–784 (1987).

Domin J., et al., "The distribution, purification, and pharmacological action of an amphibian neuromedin U" *J Biol Chem* 264: 20881–20885 (1989).

Domin J., et al., "Neuromedin U-like immunoreactivity in the thyroid gland of the rat" *Cell Tissue Res* 260:131–135 (1990).

Fong, T. M., et al., "Mutational analysis of neurokinin receptor function" *Can. J. Physio. Pharmacol.* 73(7): 860–865 (1995).

Gardiner S. M., et al., "Regional hemodynamic effects of neuromedin U in conscious rats" *Am J Physiol* 258: R32–38 (1990).

Graziano, M. P. et al., "The amino terminal domain of the glucagon-like peptide-1 receptor is a critical determinant of subtype specificity" *Receptors Channels* 4(1): 9–17 (1996).

Guan, X. M., et al., "Determination of Structural Domains for G Protein Coupling and Ligand Binding in β3—Adrenergic Receptor" *Mol. Pharmacol.* 48(3): 492–498 (1995).

Gundersen, C. B., et al., "Serotonin receptors induced by exogenous messenger RNA in *Xenopus* oocytes" *Proc. R. Soc. Lond. B. Biol. Sci.* 219(1214): 103–109 (1983).

Hashimoto T., et al., "Agonistic and antagonistic activities of neuromedin U-8 analogs substituted with glycine or D-amino acid on contractile activity of chicken crop smooth muscle preparations" *Chem Pharm Bull (Tokyo)* 39(9): 2319–2322 (1991).

Honzawa M., et al., "Topographic Localization of neuromedin U-like structures in the rat brain: an immunohistochemical study" *Neuroscience* 23:1103–1122 (1987).

Inanobe, A., et al., "Characterization of G-protein-gated K+ channels composed of Kir3.2 subunits in dopaminergic neurons of the substantia nigra" *J. of Neuroscience* 19(3): 1006–1017 (1999).

Krapivinsky, G., et al., "The cardiac inward rectifier K+ channel subunit, CIR, does not comprise the ATP-sensitive K+ channel, IKATP" *J. Biol. Chem.* 270: 28777–28779 (1995b).

Krapivinsky, G., et al., "The G-protein-gated atrial K+ channel IKACh is a heteromultimer of two inwardly rectifying K(+)-channel proteins" *Nature* 374: 135–141 (1995).

Kubo, Y., et al., "Primary structure and functional expression of a rat G-protein-coupled muscarinic potassium channel" *Nature* 364: 802–806 (1993).

Lazareno, S. and Birdsall, N. J. M. "Pharmacological characterization of acetylcholine stimulated [$^{35}$S]-GTPgS binding mediated by human muscarinic m1–m4 receptors: antagonist studies", *Br. J. Pharmacology* 109: 1120–1127 (1993).

Lo, G., et al., "Characterization of complementary DNA encoding the rat neuromedin U precursor" *Molecular Endocrinology* 6:1538–1544 (1992).

Maggi, C. A., et al., "Motor response of the human isolated small intestine and urinary bladder to porcine neuromedin U-8" *Br J Pharmacol* 99: 186–188 (1990).

Malendowicz, L. K. and G. G. Nussdorfer "Neuromedin U (NMU)-23, but not NMU-8, inhibits basal corticosterone secretion by isolated zona fasciculata-reticularis cells of the rat adrenal cortex" *Biomedical Letters* 48:291–294 (1993).

Malendowicz, L. K., et al., "Effects of neuromedin U-8 on the rat pituitary-adrenocortical axis" *In Vivo* 7:419–422 (1993).

Malendowicz, L. K and A. Markowska, "Neuromedins and their involvement in the regulation of growth, structure and function of the adrenal cortex" *Histol Histopath* 9:591–601 (1994).

Malendowicz, L. K., et al., "Effects of Neuromedin U (NMU)-8 on the rat hypothalamo-pituitary-adrenal axis. Evidence of a direct effect of NMU-8 on the adrenal gland" *Neuropeptides* 26:47–53 (1994a).

Malendowicz, L. K., et al., "Effects of neuromedin U-8 on the secretory activity of the rat adtenal cortex: Evidence for an indirect action requiring the presence of the zona medullaris" *Res Exp Med* 194:69–79 (1994b).

Milligan, G. and S. Rees, "Chimaeric G alpha proteins: their potential use in drug discovery" *Trends Pharmacol. Sci.* 20: 118–124 (1999).

Minamino, N., et al., "Neuromedins: Novel smooth muscle stimulation peptides identified in porcine spinal cord" *Peptides* 6:245–248 (1985a).

Minamino, N., et al., "Neuromedin U-8 and U-25: Novel uterus stimulating and hypertensive peptide identified in porcine spinal cord" *Biochem Biophys Res Commun* 130: 1078–1085 (1985b).

Nandha, K. A., et al. "Autoradiographic analysis of specific neuromedin U binding sites in the rat uterus and brain" *J. of Endocrinology* 140(Suppl.): Abstract No. P177 (1994).

Nandha K. A. and S. R. Bloom, "Neuromedin U—An overview" *Biomedical Research* 14(Supl.3):71–76 (1993).

Nandha, K. A., et al., "Characterization of the rat uterine neuromedin U receptor." *Endocrinology* 133:482–486 (1993).

O'Harte, F., et al., "Isolation, structural characterization and pharmacological activity of dog neuromedin U" *Peptides* 12:11–15 (1991).

Quick, M. W. and Lester, H. A., "Methods for expression of excitability proteins in *Xenopus* oocytes", *Meth. Neurosci.* 19: 261–279 (1994).

Sakura, N., et al., "Structure-activity relationships of rat neuromedin U for smooth muscle contraction" *Chem Pharm Bull (Tokyo)* 39: 2016–2020 (1991).

Salon, J. A. and Owicki, J. A., "Real-time measurements of receptor activity: Application of microphysiometic techniques to receptor biology" *Methods in Neuroscience* 25: 201–224, Academic Press (1996).

Smith, K. E., et al., "Expression cloning of a rat hypothalamic galanin receptor coupled to phosphoinositide turnover." *J. Biol. Chem.* 272: 24612–24616 (1997).

Spurney, R. F., et al., "The C-terminus of the thromboxane receptor contributes to coupling and desensitization in a mouse mesangial cell line", *J. Pharmacol. Exp. Ther.* 283(1): 207–215 (1997).

Steel, J. H., et al., "Localization of 7B2, Neuromedin B, and neuromedin U in specific cell types of rat, mouse, and human pituitary, in rat hypothalamus, and in 30 human pituitary and extrapituitary tumors" *Endocrinology* 122: 270–282 (1988).

Sumi, S., et al., "Effect of synthetic neuromedin U-8 and U-25, novel peptides identified in porcine spinal cord, on splanchnic circulation in dogs" *Life Sci* 41:1585–1590 (1987).

Takahashi, T., et al., "Rat brain serotonin receptors in *Xenopus* oocytes are coupled by intracellular calcium to endogenous channels." *Proc. Natl. Acad. Sci. USA* 84(14): 5063–5067 (1987).

Tian, W., et al., "Determinants of alpha-Adrenergic Receptor Activation of G protein: Evidence for a Precoupled Receptor/G protein State." *Molecular Pharmacology* 45: 524–553 (1994).

Underwood, D. J. et al., "Structural model of antagonist and agonist binding to the angiotensin II, AT1 subtype, G protein coupled receptor", *Chem. Biol.* 1(4): 211–221 (1994).

What is claimed is:

1. A process involving competitive binding for identifying a chemical compound which specifically binds to a mammalian SNORF72 receptor which comprises separately contacting cells, or a membrane preparation from such cells, expressing on their cell surface the mammalian SNORF72 receptor, wherein such cells do not normally express the mammalian SNORF72 receptor, with both the chemical compound and a second chemical compound known to bind to the receptor, and with only the second chemical compound, under conditions suitable for binding of such compounds to the receptor, and detecting specific binding of the chemical compound to the mammalian SNORF72 receptor, a decrease in the binding of the second chemical compound to the mammalian SNORF72 receptor in the presence of the chemical compound being tested indicating that such chemical compound binds to the mammalian SNORF72 receptor; wherein the mammalian SNORF72 receptor is a human SNORF72 receptor which has an amino acid sequence identical to (1) that encoded by the plasmid pEXJ.T3T7-hSNORF72-f (ATCC amino acid sequence shown in SEQ ID NO: 4; or a rat SNORF72 receptor which has an amino acid sequence identical to (1) that encoded by the plasmid pEXJ.BS-rSNORF72-f (ATCC Patent Deposit Designation No. PTA-1927) or (2) the amino acid sequence shown in SEQ ID NO: 25.

2. The process of claim 1, wherein the cell is an insect cell.

3. The process of claim 1, wherein the cell is a mammalian cell.

4. The process of claim 3, wherein the cell is normeuronal in origin.

5. The process of claim 4, wherein the normeuronal cell is a COS-7 cell, 293 human embryonic kidney cell, a CHO cell, a NIH-3T3 cell, a mouse Y1 cell, or a LM(tk–) cell.

6. The process of claim 5, wherein the compound is not previously known to bind to a mammalian SNORF72 receptor.

7. A method of screening a plurality of chemical compounds not known to bind to a mammalian SNORF72 receptor to identify a compound which specifically binds to the mammalian SNORF72 receptor, which comprises (a) contacting cells, or a membrane preparation from such cells, transfected with, and expressing, DNA encoding the mammalian SNORF72 receptor with a compound known to bind specifically to the mammalian SNORF72 receptor;

(b) contacting the cells of step (a) with the plurality of compounds not known to bind specifically to the mammalian SNORF72 receptor, under conditions permitting binding of compounds known to bind to the mammalian SNORF72 receptor;

(c) determining whether the binding of the compound known to bind to the mammalian SNORF72 receptor is reduced in the presence of the plurality of compounds, relative to the binding of the compound in the absence of the plurality of compounds; and if so (d) separately determining the binding to the mammalian SNORF72 receptor of each compound included in the plurality of compounds, so as to thereby identify any compound included therein which specifically binds to the mammalian SNORF72 receptor; wherein the mammalian SNORF72 receptor is a human SNORF72 receptor which has an amino acid sequence identical to (1) that encoded by the plasmid pEXJ.T3T7-hSNORF72-f (ATCC Patent Deposit Designation No. PTA-1446) or (2) the amino acid sequence shown in SEQ ID NO: 4; or a rat SNORF72 receptor which has an amino acid sequence identical to (1) that encoded by the plasmid pEXJ.BS-rSNORF72-f (ATCC Patent Deposit Designation No. PTA-1927) or (2) the amino acid sequence shown in SEQ ID NO: 25.

8. The method of claim 7, wherein the cell is a mammalian cell.

9. The method of claim 8, wherein the mammalian cell is non-neuronal in origin.

10. The method of claim 9, wherein the non-neuronal cell is a COS-7 cell, a 293 human embryonic kidney cell, a LM(tk–) cell, a CHO cell, a mouse Y1 cell, or an NIH-3T3 cell.

11. A process for determining whether a chemical compound is a mammalian SNORF72 receptor antagonist which comprises contacting cells transfected with and expressing DNA encoding the mammalian SNORF72 receptor with the compound in the presence of a known mammalian SNORF72 receptor agonist, under conditions permitting the activation of the mammalian SNORF72 receptor, and detecting any decrease in mammalian SNORF72 receptor activity, so as to thereby determine whether the compound is a mammalian SNORF72 receptor antagonist; wherein the mammalian SNORF72 receptor is a human SNORF72 receptor which has an amino acid sequence identical to (1) that encoded by the plasmid pEXJ.T3T7-hSNORF72-f (ATCC Patent Deposit Designation No. PTA-1446) or (2) the amino acid sequence shown in SEQ ID NO: 4; or a rat SNORF72 receptor which has an amino acid sequence identical to (1) that encoded by the plasmid PEXJ.BS-rSNORF72-f (ATCC Patent Deposit Designation No. PTA-1927) or (2) the amino acid sequence shown in SEQ ID NO: 25.

12. A process for determining whether a chemical compound specifically binds to and inhibits activation of a mammalian SNORF72 receptor, which comprises separately contacting cells producing a second messenger response and expressing on their cell surface the mammalian SNORF72 receptor, wherein such cells do not normally express the mammalian SNORF72 receptor, with both the chemical compound and a second chemical compound known to activate the mammalian SNORF72 receptor, and with only the second chemical compound, under conditions suitable for activation of the mammalian SNORF72 receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the mammalian SNORF72 receptor; wherein the mammalian SNORF72 receptor is a human SNORF72 receptor which has an amino acid sequence identical to (1) that encoded by the plasmid pEXJ.T3T7-hSNORF72-f (ATCC Patent Deposit Designation No. PTA-1446) or (2) the amino acid sequence shown in SEQ ID NO: 4; or a rat SNORF72 receptor which has an amino acid sequence identical to (1) that encoded by the plasmid pEXJ.BS-rSNORF72-f (ATCC Patent Deposit Designation No. PTA-1927) or (2) the amino acid sequence shown in SEQ ID NO: 25.

13. The process of claim 12, wherein the second messenger response comprises chloride channel activation and the change in second messenger response is a smaller increase in the level of chloride current in the presence of both the chemical compound and the second chemical compound than in the presence of only the second chemical compound.

14. The process of claim 12, wherein the second messenger response comprises change in intracellular calcium levels and the change in second messenger response is a smaller increase in the measure of intracellular calcium in the presence of both the chemical compound and the second chemical compound than in the presence of only the second chemical compound.

15. The process of claim 12, wherein the second messenger response comprises release of inositol phosphate and the change in second messenger response is a smaller increase in the level of inositol phosphate in the presence of both the chemical compound and the second chemical compound than in the presence of only the second chemical compound.

16. The process of claim 12, wherein the cell is an insect cell.

17. The process of claim 12, wherein the cell is a mammalian cell.

18. The process of claim 17, wherein the mammalian cell is nonneuronal in origin.

19. The process of claim 18, wherein the normeuronal cell is a COS-7 cell, CHO cell, 293 human embryonic kidney cell, NIH-3T3 cell or LM(tk−) cell.

20. A method of screening a plurality of chemical compounds not known to inhibit the activation of a mammalian SNORF72 receptor to identify a compound which inhibits the activation of the mammalian SNORF72 receptor, which comprises:

(a) contacting cells transfected with and expressing the mammalian SNORF72 receptor with the plurality of compounds in the presence of a known mammalian SNORF72 receptor agonist, under conditions permitting activation of the mammalian SNORF72 receptor;

(b) determining whether the extent or amount of activation of the mammalian SNORF72 receptor is reduced in the presence of one or more of the compounds, relative to the extent or amount of activation of the mammalian SNORF72 receptor in the absence of such one or more compounds; and if so (c) separately determining whether each such compound inhibits activation of the mammalian SNORF72 receptor for each compound included in the plurality of compounds, so as to thereby identify any compound included in such plurality of compounds which inhibits the activation of the mammalian SNORF72 receptor; wherein the mammalian SNORF72 receptor is a human SNORF72 receptor which has an amino acid sequence identical to (1) that encoded by the plasmid pEXJ.T3T7-hSNORF72-f (ATCC Patent Deposit Designation No. PTA-1446) or (2) the amino acid sequence shown in SEQ ID NO: 4; or a rat SNORF72 receptor which has an amino acid sequence identical to (1) that encoded by the plasmid pEXJ.BS-rSNORF72-f (ATCC Patent Deposit Designation No. PTA-1927) or (2) the amino acid sequence shown in SEQ ID NO: 25.

21. The method of claim 20, wherein the cell is a mammalian cell.

22. The method of claim 21, wherein the mammalian cell is non-neuronal in origin.

23. The method of claim 22, wherein the non-neuronal cell is a COS-7 cell, a 293 human embryonic kidney cell, a LM(tk−) cell or an NIH-3T3 cell.

24. A process for preparing a composition which comprises a chemical compound identified by the process of any of claim 1 or 7, recovering the compound free of any receptor, and admixing with a pharmaceutically acceptable carrier.

25. A process for preparing a composition which comprises a chemical compound identified by the process of any of claims 11, 12 or 20, recovering the compound free of any receptor, and admixing with a pharmaceutically acceptable carrier.

* * * * *

SEQUENCE LISTING

<160> NUMBER OF SEQ ID NOS: 46

<210> SEQ ID NO 1
<211> LENGTH: 1318
<212> TYPE: DNA

<210> ORGANISM: Artificial Sequence
<220> FEATURE:
<223> OTHER INFORMATION: Description of Artificial Sequence:
       primer/probe

<400> SEQUENCE: 1

```
gagggtggaa gccgggtct cgcgggccgc gggccgcatg actcctctct gcctcaattg      60
ctctgtcctc cctggagacc tgtacccagg gggtgcaagg aacccatgg cttgcaatgg     120
cagtgcggcc aggggcact ttgaccctga ggacttgaac ctgactgacg aggcactgag     180
actcaagtac ctggggcccc agcagacaga gctgttcatg cccatctgtg ccacatacct     240
gctgatcttc gtggtgggcg ctgtgggcaa tgggctgacc tgtctggtca tcctgcgcca     300
caaggccatg cgcacgccta ccaactacta cctcttcagc ctggccgtgt cggacctgct     360
ggtgctgctg gtgggcctgc ccctggagct ctatgagatg tggcacaact ccccttcct     420
gctgggcgtt ggtggctgct atttccgcac gctactgttt gagatggtct gcctggcctc     480
agtgctcaac gtcactgccc tgagcgtgga acgctatgtg gccgtggtgc acccactcca     540
ggccaggtcc atggtgacgc gggcccatgt gcgccgagtg cttggggccg tctggggtct     600
tgccatgctc tgctccctgc ccaacaccag cctgcacggc atccggcagc tgcacgtgcc     660
ctgccggggc ccagtgccag actcagctgt ttgcatgctg gtccgcccac gggccctcta     720
caacatggta gtgcagacca ccgcgctgct cttcttctgc ctgcccatgg ccatcatgag     780
cgtgctctac ctgctcattg ggctgcgact gcggcgggag aggctgctgc tcatgcagga     840
ggccaagggc aggggctctg cagcagccag gtccagatac acctgcaggc tccagcagca     900
cgatcgggc cggagacaag tgaccaagat gctgtttgtc ctggtcgtgg tgtttggcat     960
ctgctggccc ccgttccacg ccgaccgcgt catgtggagc gtcgtgtcac agtggacaga    1020
tggcctgcac ctggccttcc agcacgtgca cgtcatctcc ggcatcttct ctacctggg    1080
ctcggcggcc aacccgtgc tctatagcct catgtccagc cgcttccgag agaccttcca    1140
ggaggccctg tgcctcgggg cctgctgcca tcgcctcaga ccccgccaca gctcccacag    1200
cctcagcagg atgaccacag gcagcaccct gtgtgatgtg ggctccctgg gcagctgggt    1260
ccacccctg gctgggaacg atggcccaga ggcgcagcaa gagaccgatc catcctga      1318
```

<210> SEQ ID NO 2
<211> LENGTH: 426
<212> TYPE: PRT
<213> ORGANISM: Artificial Sequence
<220> FEATURE:
<223> OTHER INFORMATION: Description of Artificial Sequence:
       primer/probe

<400> SEQUENCE: 2

```
Met Thr Pro Leu Cys Leu Asn Cys Ser Val Leu Pro Gly Asp Leu Tyr
  1               5                  10                  15

Pro Gly Gly Ala Arg Asn Pro Met Ala Cys Asn Gly Ser Ala Ala Arg
                 20                  25                  30

Gly His Phe Asp Pro Glu Asp Leu Asn Leu Thr Asp Glu Ala Leu Arg
             35                  40                  45

Leu Lys Tyr Leu Gly Pro Gln Gln Thr Glu Leu Phe Met Pro Ile Cys
         50                  55                  60

Ala Thr Tyr Leu Leu Ile Phe Val Val Gly Ala Val Gly Asn Gly Leu
 65                  70                  75                  80

Thr Cys Leu Val Ile Leu Arg His Lys Ala Met Arg Thr Pro Thr Asn
                 85                  90                  95
```

```
Tyr Tyr Leu Phe Ser Leu Ala Val Ser Asp Leu Val Leu Leu Val
            100                 105                 110
Gly Leu Pro Leu Glu Leu Tyr Glu Met Trp His Asn Tyr Pro Phe Leu
            115                 120                 125
Leu Gly Val Gly Gly Cys Tyr Phe Arg Thr Leu Leu Phe Glu Met Val
130                 135                 140
Cys Leu Ala Ser Val Leu Asn Val Thr Ala Leu Ser Val Glu Arg Tyr
145                 150                 155                 160
Val Ala Val Val His Pro Leu Gln Ala Arg Ser Met Val Thr Arg Ala
            165                 170                 175
His Val Arg Arg Val Leu Gly Ala Val Trp Gly Leu Ala Met Leu Cys
            180                 185                 190
Ser Leu Pro Asn Thr Ser Leu His Gly Ile Arg Gln Leu His Val Pro
            195                 200                 205
Cys Arg Gly Pro Val Pro Asp Ser Ala Val Cys Met Leu Val Arg Pro
210                 215                 220
Arg Ala Leu Tyr Asn Met Val Val Gln Thr Thr Ala Leu Leu Phe Phe
225                 230                 235                 240
Cys Leu Pro Met Ala Ile Met Ser Val Leu Tyr Leu Leu Ile Gly Leu
            245                 250                 255
Arg Leu Arg Arg Glu Arg Leu Leu Leu Met Gln Glu Ala Lys Gly Arg
            260                 265                 270
Gly Ser Ala Ala Ala Arg Ser Arg Tyr Thr Cys Arg Leu Gln Gln His
            275                 280                 285
Asp Arg Gly Arg Arg Gln Val Thr Lys Met Leu Phe Val Leu Val Val
290                 295                 300
Val Phe Gly Ile Cys Trp Ala Pro Phe His Ala Asp Arg Val Met Trp
305                 310                 315                 320
Ser Val Val Ser Gln Trp Thr Asp Gly Leu His Leu Ala Phe Gln His
            325                 330                 335
Val His Val Ile Ser Gly Ile Phe Phe Tyr Leu Gly Ser Ala Ala Asn
            340                 345                 350
Pro Val Leu Tyr Ser Leu Met Ser Ser Arg Phe Arg Glu Thr Phe Gln
            355                 360                 365
Glu Ala Leu Cys Leu Gly Ala Cys Cys His Arg Leu Arg Pro Arg His
            370                 375                 380
Ser Ser His Ser Leu Ser Arg Met Thr Thr Gly Ser Thr Leu Cys Asp
385                 390                 395                 400
Val Gly Ser Leu Gly Ser Trp Val His Pro Leu Ala Gly Asn Asp Gly
            405                 410                 415
Pro Glu Ala Gln Gln Glu Thr Asp Pro Ser
            420                 425

<210> SEQ ID NO 3
<211> LENGTH: 1298
<212> TYPE: DNA
<213> ORGANISM: Artificial Sequence
<220> FEATURE:
<223> OTHER INFORMATION: Description of Artificial Sequence:
      primer/probe

<400> SEQUENCE: 3
aggggaggct caggccttgg attttaatgt cagggatgga aaaacttcag aatgcttcct      60
ggatctacca gcagaaacta gaagatccat tccagaaaca cctgaacagc accgaggagt     120
```

-continued

```
atctggcctt cctctgcgga cctcggcgca gccacttctt cctccccgtg tctgtggtgt    180
atgtgccaat ttttgtggtg ggggtcattg gcaatgtcct ggtgtgcctg gtgattctgc    240
agcaccaggc tatgaagacg cccaccaact actacctctt cagcctggcg gtctctgacc    300
tcctggtcct gctccttgga atgccctgg aggtctatga gatgtggcgc aactacccctt    360
tcttgttcgg gcccgtgggc tgctacttca agacggccct ctttgagacc gtgtgcttcg    420
cctccatcct cagcatcacc accgtcagcg tggagcgcta cgtggccatc ctacacccgt    480
tccgcgccaa actgcagagc acccggcgcc gggccctcag gatcctcggc atcgtctggg    540
gcttctccgt gctcttctcc ctgcccaaca ccagcatcca tggcatcaag ttccactact    600
tccccaatgg gtccctggtc ccaggttcgg ccacctgtac ggtcatcaag cccatgtgga    660
tctacaattt catcatccag gtcacctcct tcctattcta cctcctcccc atgactgtca    720
tcagtgtcct ctactacctc atggcactca gactaaagaa agacaaatct cttgaggcag    780
atgaagggaa tgcaaatatt caagaccct gcagaaaatc agtcaacaag atgctgtttg    840
tcttggtctt agtgtttgct atctgttggg ccccgttcca cattgaccga ctcttcttca    900
gctttgtgga ggagtggagt gaatccctgg ctgctgtgtt caacctcgtc catgtggtgt    960
caggtgtctt cttctacctg agctcagctg tcaaccccat tatctataac ctactgtctc   1020
gccgcttcca ggcagcattc cagaatgtga tctcttcttt ccacaaacag tggcactccc   1080
agcatgaccc acagttgcca cctgcccagc ggaacatctt cctgacagaa tgccactttg   1140
tggagctgac cgaagatata ggtccccaat tcccatgtca gtcatccatg cacaactctc   1200
acctcccaac agccctctct agtgaacaga tgtcaagaac aaactatcaa agcttccact   1260
taacaaaac ctgaattctt tcagagctga ctctcctc                            1298
```

<210> SEQ ID NO 4
<211> LENGTH: 415
<212> TYPE: PRT
<213> ORGANISM: Artificial Sequence
<220> FEATURE:
<223> OTHER INFORMATION: Description of Artificial Sequence:
      primer/probe

<400> SEQUENCE: 4

```
Met Ser Gly Met Glu Lys Leu Gln Asn Ala Ser Trp Ile Tyr Gln Gln
 1               5                  10                  15

Lys Leu Glu Asp Pro Phe Gln Lys His Leu Asn Ser Thr Glu Glu Tyr
            20                  25                  30

Leu Ala Phe Leu Cys Gly Pro Arg Arg Ser His Phe Leu Pro Val
        35                  40                  45

Ser Val Val Tyr Val Pro Ile Phe Val Val Gly Val Ile Gly Asn Val
    50                  55                  60

Leu Val Cys Leu Val Ile Leu Gln His Gln Ala Met Lys Thr Pro Thr
65                  70                  75                  80

Asn Tyr Tyr Leu Phe Ser Leu Ala Val Ser Asp Leu Leu Val Leu Leu
                85                  90                  95

Leu Gly Met Pro Leu Glu Val Tyr Glu Met Trp Arg Asn Tyr Pro Phe
            100                 105                 110

Leu Phe Gly Pro Val Gly Cys Tyr Phe Lys Thr Ala Leu Phe Glu Thr
        115                 120                 125

Val Cys Phe Ala Ser Ile Leu Ser Ile Thr Thr Val Ser Val Glu Arg
    130                 135                 140

Tyr Val Ala Ile Leu His Pro Phe Arg Ala Lys Leu Gln Ser Thr Arg
```

```
            145                 150                 155                 160
Arg Arg Ala Leu Arg Ile Leu Gly Ile Val Trp Gly Phe Ser Val Leu
                    165                 170                 175
Phe Ser Leu Pro Asn Thr Ser Ile His Gly Ile Lys Phe His Tyr Phe
                180                 185                 190
Pro Asn Gly Ser Leu Val Pro Gly Ser Ala Thr Cys Thr Val Ile Lys
            195                 200                 205
Pro Met Trp Ile Tyr Asn Phe Ile Ile Gln Val Thr Ser Phe Leu Phe
    210                 215                 220
Tyr Leu Leu Pro Met Thr Val Ile Ser Val Leu Tyr Tyr Leu Met Ala
225                 230                 235                 240
Leu Arg Leu Lys Lys Asp Lys Ser Leu Glu Ala Asp Glu Gly Asn Ala
                245                 250                 255
Asn Ile Gln Arg Pro Cys Arg Lys Ser Val Asn Lys Met Leu Phe Val
                260                 265                 270
Leu Val Leu Val Phe Ala Ile Cys Trp Ala Pro Phe His Ile Asp Arg
            275                 280                 285
Leu Phe Phe Ser Phe Val Glu Glu Trp Ser Glu Ser Leu Ala Ala Val
    290                 295                 300
Phe Asn Leu Val His Val Val Ser Gly Val Phe Phe Tyr Leu Ser Ser
305                 310                 315                 320
Ala Val Asn Pro Ile Ile Tyr Asn Leu Leu Ser Arg Arg Phe Gln Ala
                325                 330                 335
Ala Phe Gln Asn Val Ile Ser Ser Phe His Lys Gln Trp His Ser Gln
                340                 345                 350
His Asp Pro Gln Leu Pro Pro Ala Gln Arg Asn Ile Phe Leu Thr Glu
                355                 360                 365
Cys His Phe Val Glu Leu Thr Glu Asp Ile Gly Pro Gln Phe Pro Cys
    370                 375                 380
Gln Ser Ser Met His Asn Ser His Leu Pro Thr Ala Leu Ser Ser Glu
385                 390                 395                 400
Gln Met Ser Arg Thr Asn Tyr Gln Ser Phe His Phe Asn Lys Thr
                405                 410                 415

<210> SEQ ID NO 5
<211> LENGTH: 25
<212> TYPE: PRT
<213> ORGANISM: Artificial Sequence
<220> FEATURE:
<223> OTHER INFORMATION: Description of Artificial Sequence:
      primer/probe

<400> SEQUENCE: 5

Phe Arg Val Asp Glu Glu Phe Gln Ser Pro Phe Ala Ser Gln Ser Arg
  1               5                  10                  15
Gly Tyr Phe Leu Phe Arg Pro Arg Asn
                20                  25

<210> SEQ ID NO 6
<211> LENGTH: 25
<212> TYPE: PRT
<213> ORGANISM: Artificial Sequence
<220> FEATURE:
<223> OTHER INFORMATION: Description of Artificial Sequence:
      primer/probe

<400> SEQUENCE: 6

Phe Lys Val Asp Glu Glu Phe Gln Gly Pro Ile Val Ser Gln Asn Arg
```

```
            1               5                  10                 15
Arg Tyr Phe Leu Phe Arg Pro Arg Asn
                    20                  25

<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence:
      primer/probe

<400> SEQUENCE: 7

Tyr Lys Val Asn Glu Tyr Gln Gly Pro Val Ala Pro Ser Gly Gly Phe
  1               5                  10                  15

Phe Leu Phe Arg Pro Arg Asn
             20

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence:
      primer/probe

<400> SEQUENCE: 8

Tyr Phe Leu Phe Arg Pro Arg Asn
  1               5

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 9
ccacgaagat cagcaggtat gtgg                                          24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 10
ggcatgaaca gctctgtctg ctgg                                          24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 11
ccagccgctt ccgagagacc ttcc                                          24

<210> SEQ ID NO 12
<211> LENGTH: 24
<212> TYPE: DNA
```

```
<213> ORGANISM: Artificial Sequence
<220> FEATURE:
<223> OTHER INFORMATION: Description of Artificial Sequence:
      primer/probe

<400> SEQUENCE: 12
gcctgctgcc atcgcctcag accc                                          24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 13
gccccaggta cttgagtctc agtg                                          24

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence:
      primer/probe

<400> SEQUENCE: 14
atctataagc ttcggagggt ggaagccggg gtctc                              35

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence:
      primer/probe

<400> SEQUENCE: 15
atctatggat cctcaggatg gatcggtctc ttgctg                             36

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence:
      primer/probe

<400> SEQUENCE: 16
atctatgcgg ccgcttgaaa cagagcctcg tacc                               34

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence:
      primer/probe

<400> SEQUENCE: 17
atctattcta gagttgtaag agccattcta cctc                               34

<210> SEQ ID NO 18
<211> LENGTH: 16
<212> TYPE: DNA
<213> ORGANISM: Artificial Sequence
```

```
<220> FEATURE:
<223> OTHER INFORMATION: Description of Artificial Sequence:
      primer/probe

<400> SEQUENCE: 18
caatggcagt gcggcc                                                      16

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:
      primer/probe

<400> SEQUENCE: 19
ggtatgtggc acagatgggc                                                  20

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:
      primer/probe

<400> SEQUENCE: 20
actttgaccc tgaggacttg aacctgactg                                       30

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence:
      primer/probe

<400> SEQUENCE: 21
cctcggcgca gccac                                                       15

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:
      primer/probe

<400> SEQUENCE: 22
gaatcaccag gcacaccagg                                                  20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:
      primer/probe

<400> SEQUENCE: 23
gaatcaccag gcacaccagg                                                  20

<210> SEQ ID NO 24
<211> LENGTH: 1231
<212> TYPE: DNA
<213> ORGANISM: Artificial Sequence
<220> FEATURE:
```

<223> OTHER INFORMATION: Description of Artificial Sequence:
      primer/probe

<400> SEQUENCE: 24

| | | | | | |
|---|---|---|---|---|---|
| gttgtggatt | ttaagctcag | taatgggaaa | acttgaaaat | gcttcctgga | tccacgatcc | 60 |
| tctcatgaag | tacttgaaca | gcacagagga | gtacttggcc | cacctgtgtg | acccaagcg | 120 |
| cagtgaccta | tccctccgg | tgtctgtggc | ctatgcgctg | atcttcctgg | tgggggtaat | 180 |
| gggcaatctt | ctggtgtgca | tggtgattgt | ccgacatcag | actttgaaga | cacccaccaa | 240 |
| ctactatctc | ttcagcttgg | cagtctcaga | tctgctggtc | ctgctcttgg | ggatgcctct | 300 |
| ggaaatctac | gagatgtggc | acaattaccc | tttcctgttc | gggcctgtgg | gatgctactt | 360 |
| caagacagcc | ctcttcgaga | ctgtgtgctt | gcctccatt | ctcagtgtca | ccacggttag | 420 |
| cgtagagcgc | tatgtggcca | ttgtccaccc | tttccgagcc | aagctggaga | gcacgcggcg | 480 |
| acgggccctc | aggatcctca | gcctagtctg | gagcttctct | gtggtctttt | ctttgcccaa | 540 |
| taccagcatc | catggcatca | gttccagca | ctttcccaac | gggtcctccg | tacctggctc | 600 |
| agccaccctgc | acagtcacca | aacccatgtg | gtgtataac | ttgatcatcc | aagctaccag | 660 |
| cttcctcttc | tacatcctcc | caatgaccct | catcagcgtc | ctctactacc | tcatggggct | 720 |
| caggctgaag | agagatgaat | cccttgaggc | gaacaaagtg | gctgtgaata | ttcacagacc | 780 |
| ctctagaaag | tcagtcacca | agatgctgtt | tgtcttggtc | ctcgtgtttg | ccatctgctg | 840 |
| gaccccttc | catgtggacc | ggctcttctt | cagctttgtg | gaagagtgga | cagagtccct | 900 |
| ggctgctgtg | ttcaacctca | tccatgtggt | atcaggtgtc | ttcttttatc | tgagctccgc | 960 |
| ggtcaacccc | attatctata | acctcctgtc | tcggcgcttc | cgggcggcct | ttcgaaatgt | 1020 |
| tgtctcccct | acctgcaaat | ggtgccatcc | ccggcatcgg | ccacagggac | ctccagccca | 1080 |
| gaagatcatc | ttcttgacag | aatgtcacct | cgtggagctg | acagaggatg | caggccccca | 1140 |
| gttccctggt | cagtcatcca | tccacaacac | caaccttacc | acggccccct | gtgcaggaga | 1200 |
| ggtaccataa | aaggagtggt | cagaaggcct | c | | | 1231 |

<210> SEQ ID NO 25
<211> LENGTH: 395
<212> TYPE: PRT
<213> ORGANISM: Artificial Sequence
<220> FEATURE:
<223> OTHER INFORMATION: Description of Artificial Sequence:
      primer/probe

<400> SEQUENCE: 25

Met Gly Lys Leu Glu Asn Ala Ser Trp Ile His Asp Pro Leu Met Lys
1               5                   10                  15

Tyr Leu Asn Ser Thr Glu Glu Tyr Leu Ala His Leu Cys Gly Pro Lys
            20                  25                  30

Arg Ser Asp Leu Ser Leu Pro Val Ser Val Ala Tyr Ala Leu Ile Phe
        35                  40                  45

Leu Val Gly Val Met Gly Asn Leu Leu Val Cys Met Val Ile Val Arg
    50                  55                  60

His Gln Thr Leu Lys Thr Pro Thr Asn Tyr Tyr Leu Phe Ser Leu Ala
65                  70                  75                  80

Val Ser Asp Leu Leu Val Leu Leu Leu Gly Met Pro Leu Glu Ile Tyr
                85                  90                  95

Glu Met Trp His Asn Tyr Pro Phe Leu Phe Gly Pro Val Gly Cys Tyr
            100                 105                 110

```
Phe Lys Thr Ala Leu Phe Glu Thr Val Cys Phe Ala Ser Ile Leu Ser
        115                 120                 125
Val Thr Thr Val Ser Val Glu Arg Tyr Val Ala Ile Val His Pro Phe
        130                 135                 140
Arg Ala Lys Leu Glu Ser Thr Arg Arg Ala Leu Arg Ile Leu Ser
145                 150                 155                 160
Leu Val Trp Ser Phe Ser Val Val Phe Ser Leu Pro Asn Thr Ser Ile
                165                 170                 175
His Gly Ile Lys Phe Gln His Phe Pro Asn Gly Ser Ser Val Pro Gly
            180                 185                 190
Ser Ala Thr Cys Thr Val Thr Lys Pro Met Trp Val Tyr Asn Leu Ile
        195                 200                 205
Ile Gln Ala Thr Ser Phe Leu Phe Tyr Ile Leu Pro Met Thr Leu Ile
    210                 215                 220
Ser Val Leu Tyr Tyr Leu Met Gly Leu Arg Leu Lys Arg Asp Glu Ser
225                 230                 235                 240
Leu Glu Ala Asn Lys Val Ala Val Asn Ile His Arg Pro Ser Arg Lys
                245                 250                 255
Ser Val Thr Lys Met Leu Phe Val Leu Val Leu Val Phe Ala Ile Cys
            260                 265                 270
Trp Thr Pro Phe His Val Asp Arg Leu Phe Phe Ser Phe Val Glu Glu
        275                 280                 285
Trp Thr Glu Ser Leu Ala Ala Val Phe Asn Leu Ile His Val Val Ser
        290                 295                 300
Gly Val Phe Phe Tyr Leu Ser Ser Ala Val Asn Pro Ile Ile Tyr Asn
305                 310                 315                 320
Leu Leu Ser Arg Arg Phe Arg Ala Ala Phe Arg Asn Val Ser Pro
                325                 330                 335
Thr Cys Lys Trp Cys His Pro Arg His Arg Pro Gln Gly Pro Pro Ala
            340                 345                 350
Gln Lys Ile Ile Phe Leu Thr Glu Cys His Leu Val Glu Leu Thr Glu
        355                 360                 365
Asp Ala Gly Pro Gln Phe Pro Gly Gln Ser Ser Ile His Asn Thr Asn
    370                 375                 380
Leu Thr Thr Ala Pro Cys Ala Gly Glu Val Pro
385                 390                 395

<210> SEQ ID NO 26
<211> LENGTH: 1292
<212> TYPE: DNA
<213> ORGANISM: Artificial Sequence
<220> FEATURE:
<223> OTHER INFORMATION: Description of Artificial Sequence:
      primer/probe

<400> SEQUENCE: 26
caccatctcg gtttaagata aagatatgga gctctcccca aatgcttcaa cgggcctctt      60
gtcctgcaat gacagtgagt tcaaggagca ctttgacctt gaggacctga accttactca     120
tgaggacctg aggctgaagt acttggggcc acagcaggta aaacaatttt tgcccatctg     180
tgtcacgtac ctgttgatct tcgtagtggg cactctgggc aacgggttga cctgcaccgt     240
catcctgcgc cagaaggcaa tgcacacgcc caccaacttc tacctcttca gtctcgcggt     300
gtccgatttg ctggtgctcc tggtgggctt gccccctggaa ctttatgaga tgcagcacaa     360
ttacccattc cagctgggtg caggtggctg ttacttccgg atactgcttt tggagactgt     420
```

-continued

```
ctgcctggct tcagtgctca atgtcacagc cctaagtgtg gagcgttatg tggccgtggt    480
gcacccactc caagccaagt ctgtgatgac acggaccat  gtgcgccgca tgttgggagc    540
catctgggtc ttcgctattc tcttctctct gcccaacacc agcttacatg gcctcagtcc    600
actctatgta ccctgccggg ggccggtgcc cgattcagtt acgtgtacgc tggtgcgtcc    660
ccagttcttc tacaagttgg taatacagac gaccatactg ctcttcttct gtctgcccat    720
ggtcaccatc agtgtgctgt acctgctcat tgggctgagg ctgcggaggg agaggatgtt    780
gctccaagag gaggtcaagg gcaggatatc tgcagcagcc aggcaggcct cccacagaag    840
tattcagctt cgagataggg aacgcagaca ggtgaccaag atgctaattg ctctggttat    900
agtatttggc acctgctggg ttccattcca tgctgaccgt ctcatgtgga gtatggtgtc    960
ccattggact gacggcctgc gcctggcctt ccagtctgtg caccttgctt ctggtgtctt   1020
cttgtacctc ggctcagcgg ctaacccgga gctctacaac ctcatgtcca ctcgcttccg   1080
agagtccttc cgggaaaccc tgggccttgg gacacggtgc tgtcatcgcc accaaccgcg   1140
tcacgactcc catagccacc ttaggttgac cacagtcagc accctgtgtg acaggaacag   1200
cagggatgta cccctggctg agaacaggga tccagggtgt gagcaagaga cagaccctcc   1260
tgaataaaat cctgtggcct cacccacagg gc                                 1292
```

<210> SEQ ID NO 27
<211> LENGTH: 413
<212> TYPE: PRT
<213> ORGANISM: Artificial Sequence
<220> FEATURE:
<223> OTHER INFORMATION: Description of Artificial Sequence: primer/probe

<400> SEQUENCE: 27

```
Met Glu Leu Ser Pro Asn Ala Ser Thr Gly Leu Leu Ser Cys Asn Asp
  1               5                  10                  15

Ser Glu Phe Lys Glu His Phe Asp Leu Glu Asp Leu Asn Leu Thr His
             20                  25                  30

Glu Asp Leu Arg Leu Lys Tyr Leu Gly Pro Gln Gln Val Lys Gln Phe
         35                  40                  45

Leu Pro Ile Cys Val Thr Tyr Leu Leu Ile Phe Val Val Gly Thr Leu
     50                  55                  60

Gly Asn Gly Leu Thr Cys Thr Val Ile Leu Arg Gln Lys Ala Met His
 65                  70                  75                  80

Thr Pro Thr Asn Phe Tyr Leu Phe Ser Leu Ala Val Ser Asp Leu Leu
                 85                  90                  95

Val Leu Leu Val Gly Leu Pro Leu Glu Leu Tyr Glu Met Gln His Asn
            100                 105                 110

Tyr Pro Phe Gln Leu Gly Ala Gly Gly Cys Tyr Phe Arg Ile Leu Leu
        115                 120                 125

Leu Glu Thr Val Cys Leu Ala Ser Val Leu Asn Val Thr Ala Leu Ser
    130                 135                 140

Val Glu Arg Tyr Val Ala Val His Pro Leu Gln Ala Lys Ser Val
145                 150                 155                 160

Met Thr Arg Thr His Val Arg Arg Met Leu Gly Ala Ile Trp Val Phe
                165                 170                 175

Ala Ile Leu Phe Ser Leu Pro Asn Thr Ser Leu His Gly Leu Ser Pro
            180                 185                 190

Leu Tyr Val Pro Cys Arg Gly Pro Val Pro Asp Ser Val Thr Cys Thr
        195                 200                 205
```

```
Leu Val Arg Pro Gln Phe Phe Tyr Lys Leu Val Ile Gln Thr Thr Ile
    210                 215                 220
Leu Leu Phe Phe Cys Leu Pro Met Val Thr Ile Ser Val Leu Tyr Leu
225                 230                 235                 240
Leu Ile Gly Leu Arg Leu Arg Arg Glu Arg Met Leu Leu Gln Glu Glu
                245                 250                 255
Val Lys Gly Arg Ile Ser Ala Ala Ala Arg Gln Ala Ser His Arg Ser
                260                 265                 270
Ile Gln Leu Arg Asp Arg Glu Arg Arg Gln Val Thr Lys Met Leu Ile
            275                 280                 285
Ala Leu Val Ile Val Phe Gly Thr Cys Trp Val Pro Phe His Ala Asp
    290                 295                 300
Arg Leu Met Trp Ser Met Val Ser His Trp Thr Asp Gly Leu Arg Leu
305                 310                 315                 320
Ala Phe Gln Ser Val His Leu Ala Ser Gly Val Phe Leu Tyr Leu Gly
                325                 330                 335
Ser Ala Ala Asn Pro Glu Leu Tyr Asn Leu Met Ser Thr Arg Phe Arg
                340                 345                 350
Glu Ser Phe Arg Glu Thr Leu Gly Leu Gly Thr Arg Cys Cys His Arg
        355                 360                 365
His Gln Pro Arg His Asp Ser His Ser His Leu Arg Leu Thr Thr Val
    370                 375                 380
Ser Thr Leu Cys Asp Arg Asn Ser Arg Asp Val Pro Leu Ala Glu Asn
385                 390                 395                 400
Arg Asp Pro Gly Cys Glu Gln Glu Thr Asp Pro Pro Glu
                405                 410

<210> SEQ ID NO 28
<211> LENGTH: 1371
<212> TYPE: DNA
<213> ORGANISM: Artificial Sequence
<220> FEATURE:
<223> OTHER INFORMATION: Description of Artificial Sequence:
      primer/probe

<400> SEQUENCE: 28
gggacagcac gttagaccca agtctcatgg acttcctctc tcagtgtcat ttttttctca    60
tctgtaaaat gggattgttg tccagaaaaa ggagacattc tcagcttcgg ctctccccaa   120
atgcttcaac gggcctcttg tcctgcaatg acagtgagtt caaggagcac tttgaccttg   180
aggacctgaa ccttactcat gaggacctga ggctgaagta cttggggcca cagcaggtaa   240
aacaattttt gcccatctgt gtcacgtacc tgttgatctt cgtagtgggc actctgggca   300
acggggttga ctgcaccgtc atcctgcgcc agaaggcaat gcacacgccc accaacttct   360
acctcttcag tctcgcggtg tccgatttgc tggtgctcct ggtgggcttg ccctggaac    420
tttatgagat gcagcacaat tacccattcc agctgggtgc aggtggctgt tacttccgga   480
tactgctttt ggagactgtc tgcctggctt cagtgctcaa tgtcacagcc ctaagtgtgg   540
agcgttatgt ggccgtggtg cacccactcc aagccaagtc tgtgatgaca cggacccatg   600
tgcgccgcat gttgggagcc atctgggtct tcgctattct cttctctctg cccaacacca   660
gcttacatgg cctcagtcca ctctatgtac cctgccgggg gccggtgccc gattcagtta   720
cgtgtacgct ggtgcgtccc cagttcttct acaagttggt aatacagacg accatactgc   780
tcttcttctg tctgcccatg gtcaccatca gtgtgctgta cctgctcatt gggctgaggc   840
```

```
tgcggaggga gaggatgttg ctccaagagg aggtcaaggg caggatatct gcagcagcca    900
ggcaggcctc ccacagaagt attcagcttc gagatagggA acgcagacag gtgaccaaga    960
tgctaattgc tctggttata gtatttggca cctgctgggt tccattccat gctgaccgtc   1020
tcatgtggag tatggtgtcc cattggactg acggcctgcg cctggccttc cagtctgtgc   1080
accttgcttc tggtgtcttc ttgtacctcg gctcagcggc taacccggag ctctacaacc   1140
tcatgtccac tcgcttccga gagtccttcc gggaaaccct gggccttggg acacggtgct   1200
gtcatcgcca ccaaccgcgt cacgactccc atagccacct taggttgacc acagtcagca   1260
ccctgtgtga caggaacagc agggatgtac ccctggctga acagggat ccagggtgtg   1320
agcaagagac agaccctcct gaataaaatc ctgtggcctc acccacaggg c           1371
```

<210> SEQ ID NO 29
<211> LENGTH: 439
<212> TYPE: PRT
<213> ORGANISM: Artificial Sequence
<220> FEATURE:
<223> OTHER INFORMATION: Description of Artificial Sequence:
      primer/probe

<400> SEQUENCE: 29

```
Met Asp Phe Leu Ser Gln Cys His Phe Phe Leu Ile Cys Lys Met Gly
  1               5                  10                  15

Leu Leu Ser Arg Lys Arg Arg His Ser Gln Leu Arg Leu Ser Pro Asn
             20                  25                  30

Ala Ser Thr Gly Leu Leu Ser Cys Asn Asp Ser Glu Phe Lys Glu His
         35                  40                  45

Phe Asp Leu Glu Asp Leu Asn Leu Thr His Glu Asp Leu Arg Leu Lys
     50                  55                  60

Tyr Leu Gly Pro Gln Gln Val Lys Gln Phe Leu Pro Ile Cys Val Thr
 65                  70                  75                  80

Tyr Leu Leu Ile Phe Val Val Gly Thr Leu Gly Asn Gly Leu Thr Cys
                 85                  90                  95

Thr Val Ile Leu Arg Gln Lys Ala Met His Thr Pro Thr Asn Phe Tyr
            100                 105                 110

Leu Phe Ser Leu Ala Val Ser Asp Leu Leu Val Leu Leu Val Gly Leu
        115                 120                 125

Pro Leu Glu Leu Tyr Glu Met Gln His Asn Tyr Pro Phe Gln Leu Gly
    130                 135                 140

Ala Gly Gly Cys Tyr Phe Arg Ile Leu Leu Leu Glu Thr Val Cys Leu
145                 150                 155                 160

Ala Ser Val Leu Asn Val Thr Ala Leu Ser Val Glu Arg Tyr Val Ala
                165                 170                 175

Val Val His Pro Leu Gln Ala Lys Ser Val Met Thr Arg Thr His Val
            180                 185                 190

Arg Arg Met Leu Gly Ala Ile Trp Val Phe Ala Ile Leu Phe Ser Leu
        195                 200                 205

Pro Asn Thr Ser Leu His Gly Leu Ser Pro Leu Tyr Val Pro Cys Arg
    210                 215                 220

Gly Pro Val Pro Asp Ser Val Thr Cys Thr Leu Val Arg Pro Gln Phe
225                 230                 235                 240

Phe Tyr Lys Leu Val Ile Gln Thr Thr Ile Leu Phe Phe Cys Leu
                245                 250                 255

Pro Met Val Thr Ile Ser Val Leu Tyr Leu Leu Ile Gly Leu Arg Leu
            260                 265                 270
```

```
Arg Arg Glu Arg Met Leu Leu Gln Glu Glu Val Lys Gly Arg Ile Ser
        275                 280                 285

Ala Ala Ala Arg Gln Ala Ser His Arg Ser Ile Gln Leu Arg Asp Arg
    290                 295                 300

Glu Arg Arg Gln Val Thr Lys Met Leu Ile Ala Leu Val Ile Val Phe
305                 310                 315                 320

Gly Thr Cys Trp Val Pro Phe His Ala Asp Arg Leu Met Trp Ser Met
                325                 330                 335

Val Ser His Trp Thr Asp Gly Leu Arg Leu Ala Phe Gln Ser Val His
            340                 345                 350

Leu Ala Ser Gly Val Phe Leu Tyr Leu Gly Ser Ala Ala Asn Pro Glu
        355                 360                 365

Leu Tyr Asn Leu Met Ser Thr Arg Phe Arg Glu Ser Phe Arg Glu Thr
    370                 375                 380

Leu Gly Leu Gly Thr Arg Cys Cys His Arg His Gln Pro Arg His Asp
385                 390                 395                 400

Ser His Ser His Leu Arg Leu Thr Thr Val Ser Thr Leu Cys Asp Arg
                405                 410                 415

Asn Ser Arg Asp Val Pro Leu Ala Glu Asn Arg Asp Pro Gly Cys Glu
            420                 425                 430

Gln Glu Thr Asp Pro Pro Glu
        435

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence:
      primer/probe

<400> SEQUENCE: 30
tacctgctga tcttcgtggt ggg                                             23

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 31
cagtgcaaac agcatcttgg tcac                                            24

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence:
      primer/probe

<400> SEQUENCE: 32
tatgtggccg tggtgcgccc actcc                                           25

<210> SEQ ID NO 33
<211> LENGTH: 27
<212> TYPE: DNA
<213> ORGANISM: Artificial Sequence
<220> FEATURE:
```

<223> OTHER INFORMATION: Description of Artificial Sequence:
      primer/probe

<400> SEQUENCE: 33
ccacctgctg cacccagctg gaatggg                                              27

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 34
actgaagcca ggcagacagt ctcc                                                 24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 35
tggtcaccat cagtgtgctg tacc                                                 24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 36
tgcggaggga gaggatgttg ctcc                                                 24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 37
cccaagtact tcagcctcag gtcc                                                 24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 38
ggtcaacccg ttgcccagag tgcc                                                 24

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence:

primer/probe

<400> SEQUENCE: 39
tctatgagat gtggcgcaac tacc                                    24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 40
aacactaaga ccaagacaaa cagc                                    24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 41
gtcaccacgg ttagcgtaga gcgc                                    24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 42
gagggtctgt gaatattcac agcc                                    24

<210> SEQ ID NO 43
<211> LENGTH: 45
<212> TYPE: DNA
<213> ORGANISM: Artificial Sequence
<220> FEATURE:
<223> OTHER INFORMATION: Description of Artificial Sequence:
      primer/probe

<400> SEQUENCE: 43
cccaacgggt cctccgtacc tggctcagcc acctgcacag tcacc             45

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence:
      primer/probe

<400> SEQUENCE: 44
gcctgtggga tgctacttca ag                                      22

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence:
      primer/probe -continued

```
<400> SEQUENCE: 45
cgctaaccgt ggtgacactg                                              20

<210> SEQ ID NO 46
<211> LENGTH: 29
<212> TYPE: DNA
<213> ORGANISM: Artificial Sequence
<220> FEATURE:
<223> OTHER INFORMATION: Description of Artificial Sequence:
      primer/probe

<400> SEQUENCE: 46
cttcgagact gtgtgctttg cctccattc                                    29
```